US009499459B2

(12) United States Patent
Parham et al.

(10) Patent No.: US 9,499,459 B2
(45) Date of Patent: Nov. 22, 2016

(54) MATERIALS FOR ORGANIC ELECTROLUMINESCENT DEVICES

(75) Inventors: Amir Hossain Parham, Frankfurt (DE); Arne Buesing, Frankfurt (DE); Holger Heil, Frankfurt am Main (DE); Philipp Stoessel, Frankfurt (DE); Michael Holbach, Oberursel (DE)

(73) Assignee: Merck Patent GmbH, Darmstadt (DE)

( * ) Notice: Subject to any disclaimer, the term of this patent is extended or adjusted under 35 U.S.C. 154(b) by 601 days.

(21) Appl. No.: 13/387,429

(22) PCT Filed: Jul. 5, 2010

(86) PCT No.: PCT/EP2010/004054
§ 371 (c)(1),
(2), (4) Date: Jan. 27, 2012

(87) PCT Pub. No.: WO2011/012212
PCT Pub. Date: Feb. 3, 2011

(65) Prior Publication Data
US 2012/0126180 A1    May 24, 2012

(30) Foreign Application Priority Data
Jul. 27, 2009    (DE) .................. 10 2009 034 625

(51) Int. Cl.
| | | |
|---|---|---|
| H01B 1/12 | (2006.01) |
| C07C 17/266 | (2006.01) |
| C07F 5/02 | (2006.01) |
| C07D 235/18 | (2006.01) |
| C07C 15/20 | (2006.01) |
| C07C 209/60 | (2006.01) |
| C07C 49/697 | (2006.01) |
| C07C 45/45 | (2006.01) |
| C09K 11/06 | (2006.01) |
| C09K 3/00 | (2006.01) |
| C07C 25/22 | (2006.01) |
| C07C 211/61 | (2006.01) |
| C07C 15/28 | (2006.01) |
| C07C 15/62 | (2006.01) |
| C07C 211/60 | (2006.01) |
| H01L 51/00 | (2006.01) |
| H05B 33/14 | (2006.01) |
| C09B 6/00 | (2006.01) |
| C09B 57/00 | (2006.01) |
| C09B 1/00 | (2006.01) |
| C09B 3/78 | (2006.01) |
| H01L 51/50 | (2006.01) |

(52) U.S. Cl.
CPC .............. *C07C 15/28* (2013.01); *C07C 15/62* (2013.01); *C07C 211/60* (2013.01); *C07C 211/61* (2013.01); *C09B 1/00* (2013.01); *C09B 3/78* (2013.01); *C09B 6/00* (2013.01); *C09B 57/00* (2013.01); *C09B 57/008* (2013.01); *C09K 11/06* (2013.01); *H01L 51/0054* (2013.01); *H01L 51/0058* (2013.01); *H01L 51/0067* (2013.01); *H05B 33/14* (2013.01); *C07C 2103/40* (2013.01); *C09K 2211/1011* (2013.01); *H01L 51/5012* (2013.01); *H01L 51/5048* (2013.01); *Y02E 10/549* (2013.01)

(58) Field of Classification Search
CPC ... C07C 15/28; C07C 211/60; C07C 211/61; C07C 15/62; C07C 2103/40; C09K 11/06; C09K 2211/1011; H01L 51/0054; H01L 51/0058; H01L 51/0067; H01L 51/5012; H01L 51/5048; H05B 33/14; C09B 6/00; C09B 57/00; C09B 57/008; C09B 1/00; C09B 3/78; Y02E 10/549
See application file for complete search history.

(56) References Cited

U.S. PATENT DOCUMENTS

| | | | | |
|---|---|---|---|---|
| 5,281,489 A | * | 1/1994 | Mori et al. ............... | 428/690 |
| 2004/0076853 A1 | * | 4/2004 | Jarikov .................... | 428/690 |
| 2008/0241592 A1 | * | 10/2008 | Fujita ..................... | 428/691 |
| 2008/0284322 A1 | * | 11/2008 | Hosokawa ........... C07D 215/24 313/504 |
| 2010/0181560 A1 | * | 7/2010 | Kambe ............. H01L 51/0083 257/40 |
| 2010/0187505 A1 | | 7/2010 | Stoessel et al. | |
| 2011/0012092 A1 | * | 1/2011 | Yamamoto .......... C07D 235/08 257/40 |
| 2011/0297923 A1 | * | 12/2011 | Mizuki ................ C07C 211/54 257/40 |

FOREIGN PATENT DOCUMENTS

| | | | |
|---|---|---|---|
| EP | 0728828 A2 | | 8/1996 |
| JP | H02242879 A | | 9/1990 |
| KR | 10-2007-0021043 | * | 2/2007 |
| WO | WO-2008145239 A2 | | 12/2008 |
| WO | WO 2009/084543 | * | 7/2009 |

OTHER PUBLICATIONS

Translation for Publication No. KR 10-2007-0021043 (publication date Feb. 2007).*
Translation for WO 2009/084543 (publication date: Jul. 2009).*
International Search Report for PCT/EP2010/004054 mailed Sep. 29, 2010.
Yang et al., "Synthesis and separation of the atropisomers of 2-(5-benzo[b]fluorenyl)-2'-hydroxy-1,1'-binaphthyl and related compounds", Tetrahedron, vol. 62, No. 34, pp. 8133-8141 (2006).

* cited by examiner

*Primary Examiner* — Dawn Garrett
(74) *Attorney, Agent, or Firm* — Drinker Biddle & Reath LLP

(57) ABSTRACT

The present invention relates to substituted benz[a]anthracene derivatives, to the preparation and use thereof in organic electroluminescent devices, and to organic electroluminescent devices, in particular blue-emitting devices, in which these compounds are used as matrix material or dopant in the emitting layer and/or as hole-transport material and/or as electron-transport material.

10 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2010/004054, filed Jul. 5, 2010, which claims benefit of German application 10 2009 034 625.2, filed Jul. 27, 2009.

The present invention relates to substituted benz[a]anthracene derivatives, to the preparation and use thereof in electronic devices, and to electronic devices, in particular blue-emitting organic electroluminescent devices, in which these compounds are used as matrix material or dopant in the emitting layer and/or as hole-transport material and/or as electron-transport material.

Organic semiconductors are being developed for a number of electronic applications of different types. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further improvements are still necessary before these devices can be used for high-quality and long-lived displays. Thus, in particular, the inadequate lifetime and the inadequate efficiency of blue-emitting organic electroluminescent devices currently still represent a problem which has not yet been satisfactorily solved. Furthermore, it is necessary for the compounds to have high thermal stability and a high glass-transition temperature and to be sublimable without decomposition. In particular for use at elevated temperature, a high glass-transition temperature is essential in order to achieve long lifetimes.

For fluorescent OLEDs, principally condensed aromatic compounds, in particular anthracene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in WO 01/076323, in WO 01/021729, in WO 04/013073, in WO 04/018588, in WO 03/087023, in WO 04/01858, in WO 07/021117, WO 08/145239 and in WO 07/114358. Matrix materials based on aryl-substituted pyrenes and chrysenes are disclosed in WO 04/016575. For high-quality applications, it is necessary to provide improved matrix materials.

Prior art which may be mentioned in the case of blue-emitting compounds (emitters, dopants) is the use of arylvinylamines (for example WO 04/013073, WO 04/016575, WO 04/018587). However, these compounds are thermally unstable and cannot be evaporated without decomposition, which requires high technical complexity for OLED production and thus represents a technical disadvantage. For high-quality applications, it is therefore necessary to provide improved emitting materials, particularly with respect to device and sublimation stability and emission colour.

There thus continues to be a demand for improved materials, in particular matrix materials for fluorescent emitters, especially for blue-fluorescent emitters, and fluorescent materials which are thermally stable, result in good efficiencies and at the same time in long lifetimes in organic electronic devices, give reproducible results during the production and operation of the device and are readily accessible synthetically. Further improvements are also necessary in the case of hole- and electron-transport materials.

Surprisingly, it has been found that benz[a]anthracene derivatives which are substituted in at least one of positions 8, 9 or 11, in particular 8 or 11, by an aromatic or heteroaromatic group, by a diarylamino group or by one of the other groups defined below are very highly suitable for use in organic electroluminescent devices. These compounds enable an increase in the efficiency and especially the lifetime of the device compared with materials in accordance with the prior art. This applies, in particular, to blue-fluorescent devices. Furthermore, these compounds have high thermal stability. In general, these materials are very highly suitable for use in in electronic devices, in particular in organic electroluminescent devices, since they have a high glass-transition temperature. The present invention therefore relates to these materials and to the use thereof in electronic devices.

Benz[a]anthracene derivatives which are substituted in these positions by aromatic substituents have already been described sporadically in the literature (for example K. Maruyama et al., Chem. Lett. 1975, (1), 87-88; C. L. L. Chai et al., Austr. J. Chem. 1995, 48(3), 577-591, M. C. Kloetzel et al., J. Org. Chem. 1961, 26, 1748-1754 etc.). However, only the synthesis and reactivity of these compounds have been investigated. The use of these compounds in organic electronic devices has not been proposed. Furthermore, WO 05/090365 has disclosed a multiplicity of organosilane compounds containing polycyclic aromatic groups, inter alia also for use in organic electroluminescent devices, also including, besides numerous other compounds, a compound which is an aryl-substituted benzanthracene. The particular effect of these compounds is attributed here to the presence of the organosilyl group and not to the substituted benzanthracene skeleton.

For reasons of clarity, the structure and numbering of benz[a]anthracene are shown below:

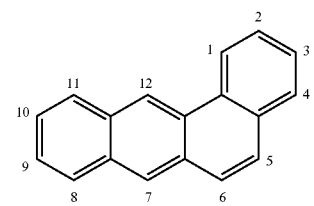

SUMMARY OF THE INVENTION

The invention relates to compounds of the following formula (1) or formula (2):

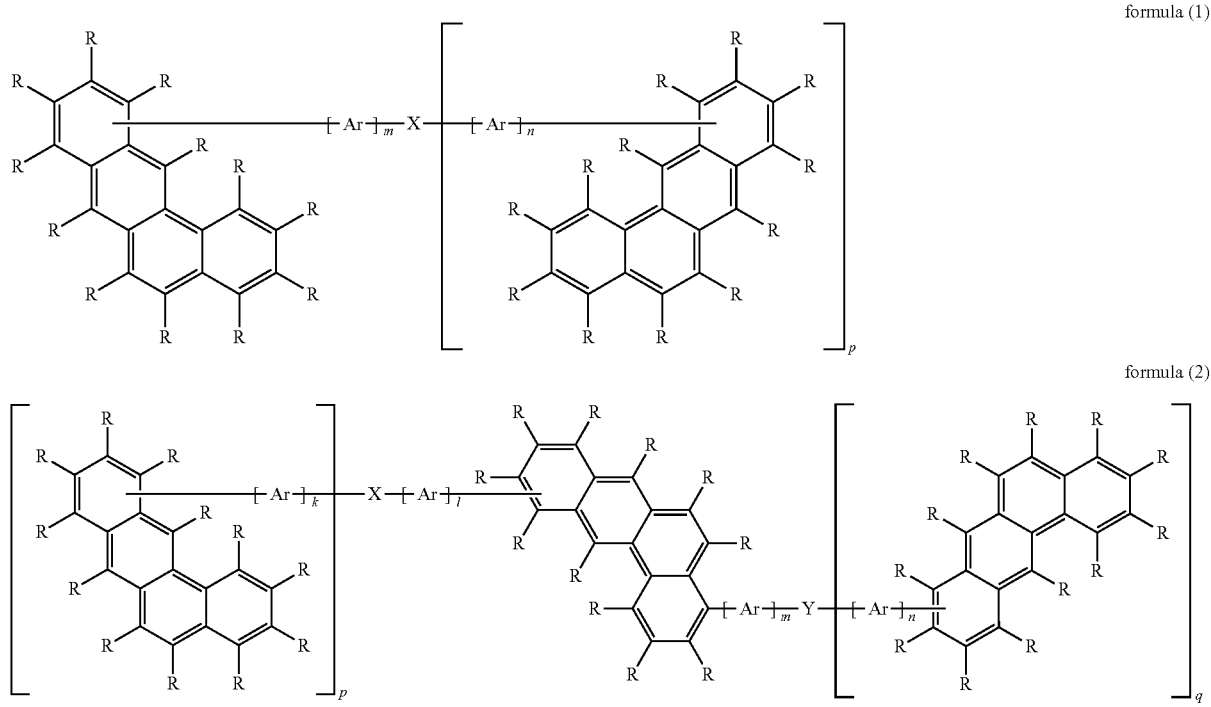

formula (1)

formula (2)

where the dashes drawn as nonspecific bonds are intended to denote that the group Ar, X or Y is bonded, in each case independently of one another, via one of positions 8, 9 or 11 of the respective benz[a]anthracene and correspondingly no radical R is bonded at this position, where the following applies to the symbols and indices:

Ar is on each occurrence, identically or differently, a divalent mono- or polycyclic aromatic or heteroaromatic ring system having 5 to 60 aromatic ring atoms, which may be substituted by one or more radicals R;

X, Y are on each occurrence, identically or differently, depending on the indices p and q, a mono-, di-, tri-, tetra-, penta- or hexavalent mono- or polycyclic aromatic or heteroaromatic ring system having 5 to 60 aromatic ring atoms, which may be substituted by one or more radicals R; or X and/or Y is, if p=0 and/or q=0, an $N(Ar^1)_2$, group; or X and/or Y is, if p=1 and/or q=1, a single bond, C=O, O, S, SO, $SO_2$, $NR^1$, $NAr^1$, $P(=O)Ar^1$, O—$B(Ar^1)$—O, O—$BR^1$—O or an alkylene group having 1 to 20 C atoms, which may in each case also be substituted by one or more radicals $R^1$, where one or more non-adjacent $CH_2$ groups may be replaced by $R^1C=CR^1$, C=C, $Si(R^1)_2$, $Ge(R^1)_2$, $Sn(R^1)_2$, C=O, C=S, C=Se, C=$NR^1$, $P(=O)(R^1)$, SO, $SO_2$, $NR^1$, O, S or $CONR^1$ and where one or more H atoms may be replaced by D, F, Cl, Br, I, CN or $NO_2$; or X and/or Y is, if p=2 and/or q=2, equal to N or P=O;

R is, identically or differently on each occurrence, H, D, F, Cl, Br, I, CHO, $N(R^1)_2$, $N(Ar^1)_2$, $C(=O)Ar^1$, $P(=O)$ $(Ar^1)_2$, $S(=O)Ar^1$, $S(=O)_2Ar^1$, $CR^1=CR^1Ar^1$, CN, $NO_2$, $Si(R^1)_3$, $B(OAr^1)_2$, $B(OR^1)_2$, $OSO_2R^1$, OH, a straight-chain alkyl, alkoxy or thioalkyl group having 1 to 40 C atoms or a branched or cyclic alkyl, alkoxy or thioalkyl group having 3 to 40 C atoms or an alkenyl group having 2 to 40 C atoms, each of which may be substituted by one or more radicals $R^1$, where one or more non-adjacent $CH_2$ groups may be replaced by $R^1C=CR^1$, C=C, $Si(R^1)_2$, $Ge(R^1)_2$, $Sn(R^1)_2$, C=O, C=S, C=Se, C=$NR^1$, $P(=O)(R^1)$, SO, $SO_2$, $NR^1$, O, S or $CONR^1$ and where one or more H atoms may be replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals R, or an aryloxy or heteroaryloxy group having 5 to 60 aromatic ring atoms, which may be substituted by one or more non-aromatic radicals R, or a combination of these systems; two or more adjacent substituents R here may also be linked to one another and form a mono- or polycyclic aliphatic ring system;

$Ar^1$ is on each occurrence, identically or differently, a mono- or polycyclic aromatic or heteroaromatic ring system having 5 to 30 aromatic ring atoms, which may be substituted by one or more non-aromatic radicals R; two radicals $Ar^1$ which are bonded to the same nitrogen or phosphorus atom may also be linked to one another here by a single bond or by a bridge selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$ and $P(=O)R^1$;

$R^1$ is on each occurrence, identically or differently, H, D or an aliphatic, aromatic and/or heteroaromatic hydrocarbon radical having 1 to 20 C atoms, in which, in addition, one or more H atoms may be replaced by F; two or more adjacent substituents $R^1$ here may also form a mono- or polycyclic aliphatic or aromatic ring system with one another;

k, l, m, n are on each occurrence, identically or differently, 0 or 1;

p, q are on each occurrence, identically or differently, 0, 1, 2, 3 or 4;

with the proviso that the following compounds of formula (1) or (2) are excluded:

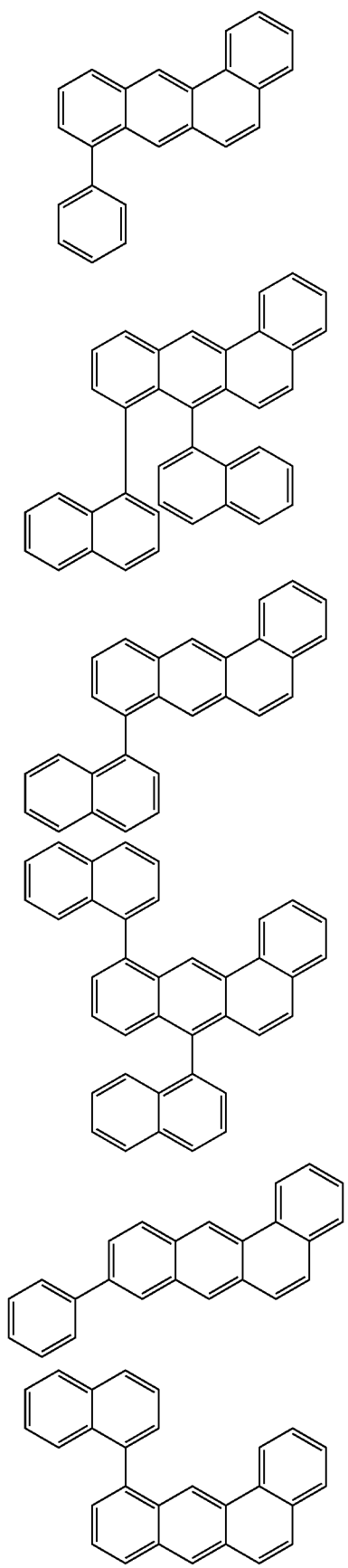

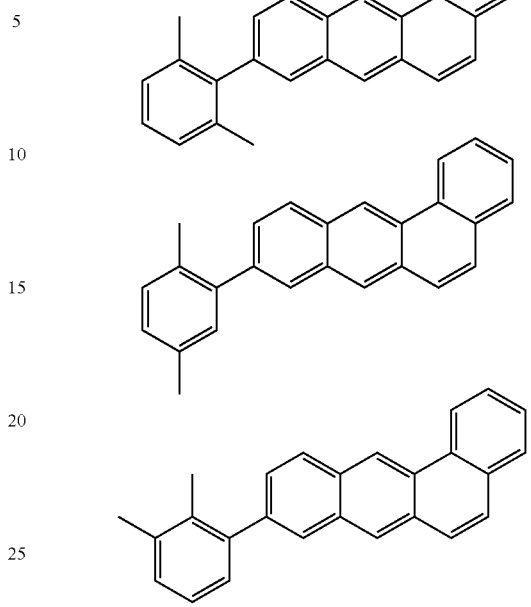

A DETAILED DESCRIPTION OF THE INVENTION

In a preferred embodiment of the invention, the compounds of the formulae (1) and (2) are uncharged.

The compounds of the formula (1) or formula (2) preferably have a glass-transition temperature $T_g$ of greater than 70° C., particularly preferably greater than 100° C., very particularly preferably greater than 130° C.

A mono-, bi-, tri-, tetra- or pentavalent mono- or polycyclic aromatic or heteroaromatic ring system preferably contains 5 to 60, particularly preferably 5 to 40, more preferably 5 to 30, even more preferably 5 to 20, even more preferably 6 to 14 and most preferably 6 to 10 aromatic ring atoms. An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. Likewise, an aromatic or heteroaromatic ring system is taken to mean systems in which a plurality of aryl or heteroaryl groups are linked to one another by single bonds, for example biphenyl, terphenyl or bipyridine. However, the aromatic or heteroaromatic ring systems are most preferably fully condensed systems.

Examples of the aromatic or heteroaromatic ring systems according to the invention, which may in each case also be substituted by the above-mentioned radicals R, preferably the non-aromatic representatives of the radical R, and which may be linked via any desired positions on the aromatic or heteroaromatic ring system, include the following: benzene, naphthalene, anthracene, phenanthrene, pyrene, chrysene, perylene, fluoranthene, naphthacene, pentacene, benzanthracene, benzophenanthrene, dibenzanthracene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthroimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, a straight-chain, branched or cyclic alkyl group is taken to mean an alkyl, alkenyl or alkynyl group, preferably having 1 to 40 C atoms, more preferably 1 to 20 C atoms, or 3 to 40 C atoms, more preferably 3 to 20 C atoms, respectively. Cyclic alkyl groups can be mono-, bi- or polycyclic alkyl groups. Individual —CH— or —CH$_2$— groups may be replaced by N, NH, O or S. Preference is given to the radicals methyl, ethyl, n-propyl, i-propyl, n-butyl, i-butyl, s-butyl, t-butyl, 2-methylbutyl, n-pentyl, s-pentyl, t-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl.

A straight-chain, branched or cyclic alkoxy or thioalkoxy group is taken to mean an alkyl group as defined above which is bonded to the remainder of the compound via an O or S atom.

Preferred alkoxy groups are methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy.

Preferred thioalkoxy groups are methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio and octynylthio.

An aryloxy or heteroaryloxy group having 5 to 60, preferably 5 to 40, particularly preferably 5 to 20, most preferably 6 to 14, aromatic ring atoms is taken to mean a group which carries a mono- or polycyclic aromatic or heteroaromatic group as defined above via an O atom.

An alkylene group is taken to mean a saturated or unsaturated aliphatic hydrocarbon, which may be linear, branched or cyclic and preferably contains 1 to 20 or 3 to 20 carbon atoms, more preferably 1 to 6 or 3 to 6 carbon atoms respectively, where, in addition, one or more CH$_2$ groups may be replaced by NH, NR$^1$, O or S, and, in addition, one or more H atoms may be replaced by F. Greater preference is given here to linear saturated hydrocarbons having 1 to 6 carbon atoms. Examples of aliphatic hydrocarbons having 1 to 10 carbon atoms include the following: methylene, ethylene, n-propylene, isopropylene, n-butylene, isobutylene, sec-butylene (1-methylpropylene), tert-butylene, isopentylene, n-pentylene, tert-pentylene (1,1-dimethylpropyl), 1,2-dimethylpropylene, 2,2-dimethylpropylene (neopentyl), 1-ethylpropylene, 2-methylbutylene, n-hexylene, isohexylene, 1,2-dimethylbutylene, 1-ethyl-1-methylpropylene, 1-ethyl-2-methylpropylene, 1,1,2-trimethylpropylene, 1,2,2-trimethylpropylene, 1-ethylbutylene, 1-methylbutylene, 1,1-dimethylbutylene, 2,2-dimethylbutylene, 1,3-dimethylbutylene, 2,3-dimethylbutylene, 3,3-dimethylbutylene, 2-ethylbutylene, 1-methylpentylene, 2-methylpentylene, 3-methylpentylene, cyclopentylene, cyclohexylene, cycloheptylene, cyclooctylene, 2-ethylhexylene, trifluoromethylene, pentafluoroethylene, 2,2,2-trifluoroethylene, ethenylene, propenylene, butenylene, pentenylene, cyclopentenylene, hexenylene, cyclohexenylene, heptenylene, cycloheptenylene, octenylene and cyclooctenylene.

Aliphatic hydrocarbons having 1 to 20 carbon atoms according to the invention are preferably linear, branched or cyclic alkyl groups, alkenyl groups or alkynyl groups, in which one or more carbon atoms may be replaced by O, N or S. In addition, one or more hydrogen atoms may be replaced by fluorine. Examples of aliphatic hydrocarbons having 1 to 20 carbon atoms include the following: methyl, ethyl, n-propyl, isopropyl, n-butyl, isobutyl, sec-butyl (1-methylpropyl), tert-butyl, isopentyl, n-pentyl, tert-pentyl (1,1-dimethylpropyl), 1,2-dimethylpropyl, 2,2-dimethylpropyl (neopentyl), 1-ethylpropyl, 2-methylbutyl, n-hexyl, isohexyl, 1,2-dimethylbutyl, 1-ethyl-1-methylpropyl, 1-ethyl-2-methylpropyl, 1,1,2-trimethylpropyl, 1,2,2-trimethylpropyl, 1-ethylbutyl, 1-methylbutyl, 1,1-dimethylbutyl, 2,2-dimethylbutyl, 1,3-dimethylbutyl, 2,3-dimethylbutyl, 3,3-dimethylbutyl, 2-ethylbutyl, 1-methylpentyl, 2-methylpentyl, 3-methylpentyl, cyclopentyl, cyclohexyl, cycloheptyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl.

An aromatic or heteroaromatic hydrocarbon preferably contains 5 to 20, more preferably 5 to 10 and most preferably 5 or 6, aromatic ring atoms. If the unit is an aromatic unit, it preferably contains 6 to 20, more preferably 6 to 10 and most preferably 6, carbon atoms as ring atoms. If the unit is a heteroaromatic unit, it contains 5 to 20, more preferably 5 to 10 and most preferably 5 or 6, aromatic ring atoms, at least one of which is a heteroatom. The heteroatoms are preferably selected from N, O and/or S. An aromatic or heteroaromatic unit here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran and indole, etc.

Examples according to the invention of the aromatic or heteroaromatic unit are accordingly: benzene, naphthalene, anthracene, phenanthrene, pyrene, chrysene, benzanthracene, benzophenanthrene, perylene, naphthacene, pentacene, benzopyrene, furan, benzofuran, isobenzofuran, dibenzofuran, thiophene, benzothiophene, isobenzothiophene, dibenzothiophene, pyrrole, indole, isoindole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A divalent or polyvalent aliphatic unit is preferably a —CH$_2$—(CH$_2$)$_h$—CH$_2$— group, where h is equal to 0, 1, 2 or 3, in the case of the divalent unit and an aliphatic group having 4 to 10 carbon atoms in the case of the polyvalent, preferably trivalent or tetravalent, unit. One or more, preferably one, CH$_2$ groups in these units may be replaced by NH, O or S, and one or more, preferably one, CH groups may be replaced by N. Furthermore, one or more H atoms may be substituted by R$^1$.

As described above, the group Ar or X or Y is bonded to the benz[a]anthracene via position 8, 9 or 11. If the compound of the formula (1) or (2) contains a plurality of benz[a]anthracene units, i.e. if the indices p and/or q are equal to or greater than 1, each of these units may be bonded via the same position of the benz[a]anthracene or via different positions of the benz[a]anthracene. Bonding via the same position of the benz[a]anthracene has the advantage that the compounds are more readily accessible synthetically. Bonding via different positions of the benz[a]anthracene results in asymmetrical compounds, which generally have the advantage of having higher solubility and a higher glass-transition temperature. In a further embodiment of the present invention, the group Ar, X or Y in formula (1) or formula (2) is preferably in each case bonded, independently of one another, via one of positions 8 and 11 of the benz[a]anthracene and correspondingly no radical R is bonded in this position. In these cases—in contrast to bonding in position 9—the formation of atropisomers around the benz[a]anthracene-Ar or benz[a]anthracene-Y bond is possible in the case of bulky groups Ar, X or Y, such as, for example, anthracene.

In still a further embodiment of the present invention, the compound of the formula (2) is preferably a compound in which, in the case where q=0, Y is a N(Ar$^1$)$_2$ group.

In a further embodiment of the invention, the respective radicals R in positions 1, 2, 3, 4, 5 and 6 of the benz[a]anthracene in the compounds of the formula (1) or (2) are preferably equal to H. In this connection, it is possible that this is only the case in one of a plurality of benzanthracene groups present. However, it is also possible for two or more or all benzanthracene groups occurring to have such a substitution.

In a further embodiment of the invention, the compound of the formula (1) or (2) preferably contains a radical R other than hydrogen in precisely one of positions 2, 3, 4, 5 or 6, preferably in position 4 or 5. This radical R is preferably an aromatic or heteroaromatic ring system, as defined above.

In a further embodiment of the present invention, the respective two radicals R in positions 7 and 12 of a benz[a]anthracene or, where appropriate, a plurality of or all benz[a]anthracenes in the compounds of the formula (1) or (2) are preferably either both equal to H or not equal to H. If the radical in positions 7 and 12 are not equal to H, they are preferably identical radicals, in particular methyl, phenyl, naphthyl or biphenyl, each of which may be substituted by one or more non-aromatic radicals R.

In still a further embodiment of the present invention, the compounds of the formula (1) or (2) are selected from the following formulae (3) to (8):

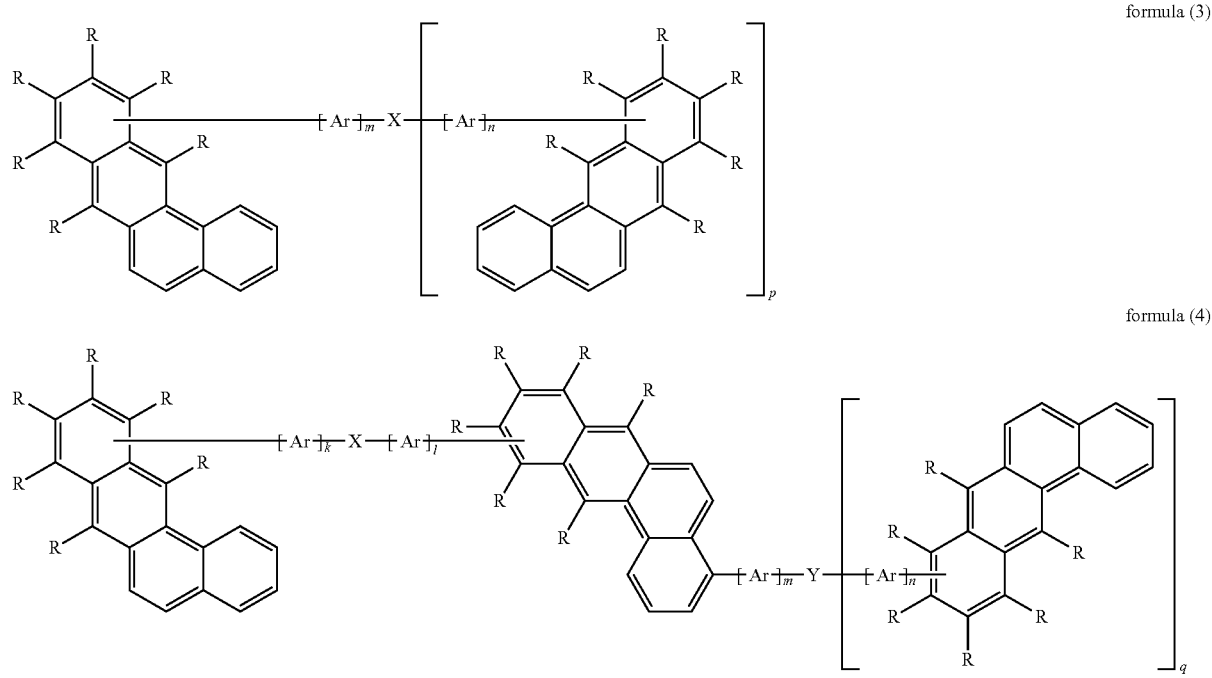

formula (3)

formula (4)

formula (5)

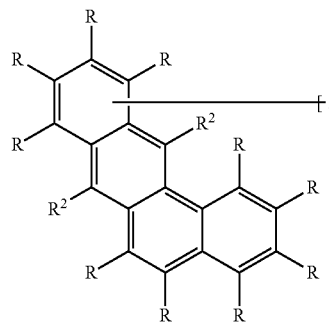 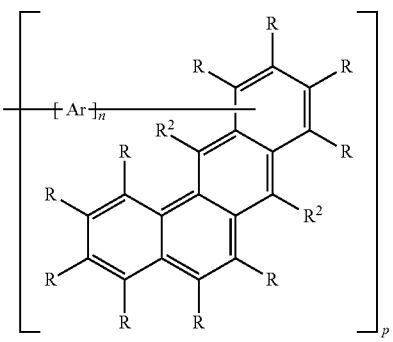

formula (6)

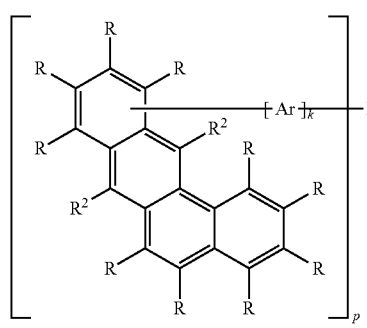 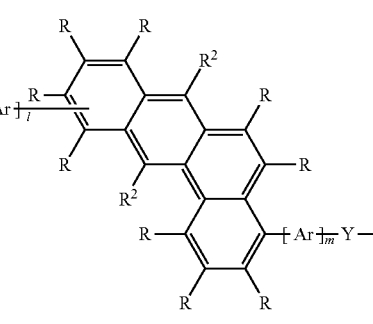 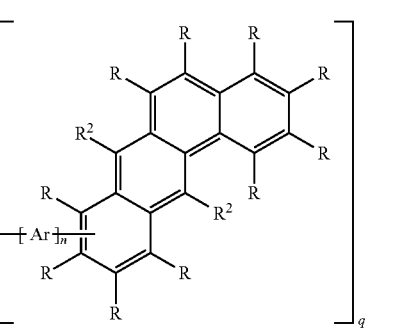

formula (7)

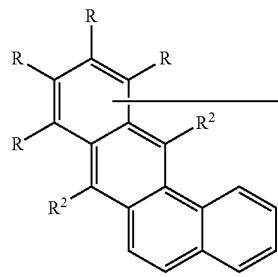 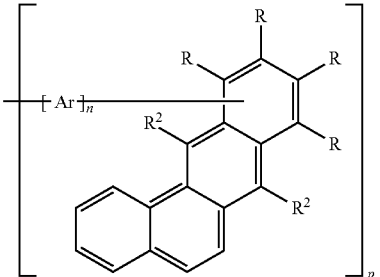

formula (8)

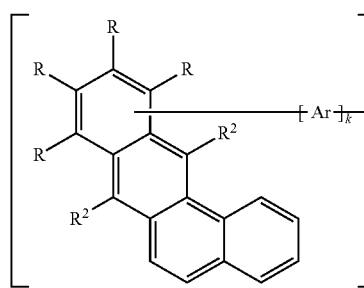 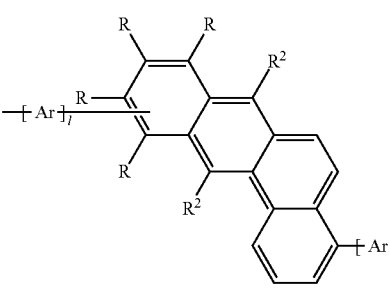 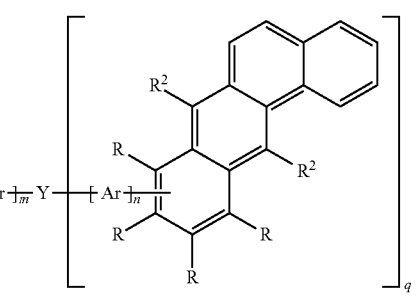

where the group Ar or X or Y is bonded via one of positions 8, 9 or 11, preferably 8 or 11, of the benz[a]anthracene or, where appropriate, the benz[a]anthracenes and where the symbols and indices have the same meanings as described in the above embodiments, where $R^2$ has the same meaning as R, with the proviso that both $R^2$ in a benz[a]anthracene are either equal to H or D or that both $R^2$ are not equal to H and D.

In the structures of the formulae (3) to (8), the substituent R in the 1-position on the benzanthracene or on a plurality of or all benzanthracenes is preferably hydrogen. It is likewise particularly preferred for all substituents R to be equal to hydrogen.

In still a further embodiment of the present invention, the compounds of the above embodiments are preferably selected from the formulae (9) to (21), formula (9)
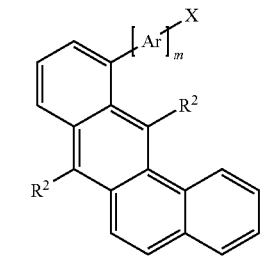
formula (10)
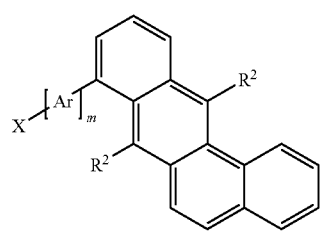
formula (11)
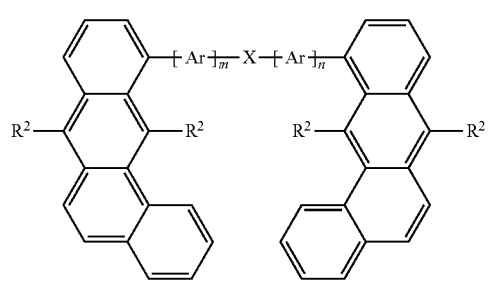
formula (12)
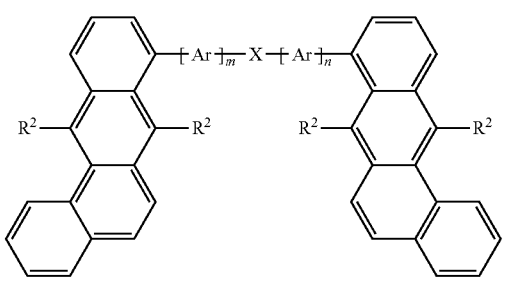
formula (13)
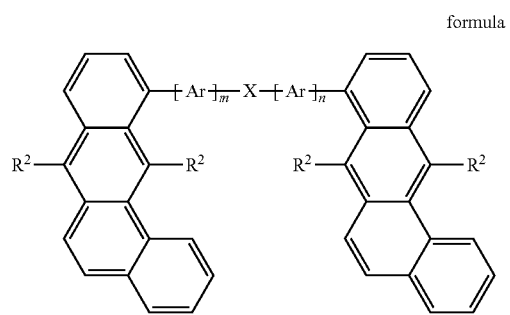
-continued
formula (14)
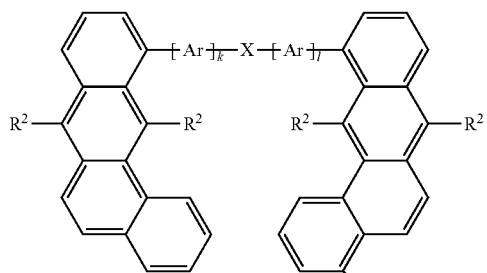
formula (15)
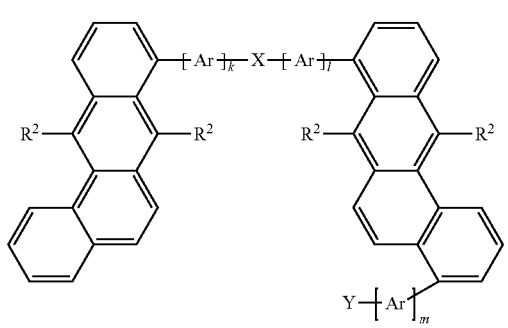
formula (16)
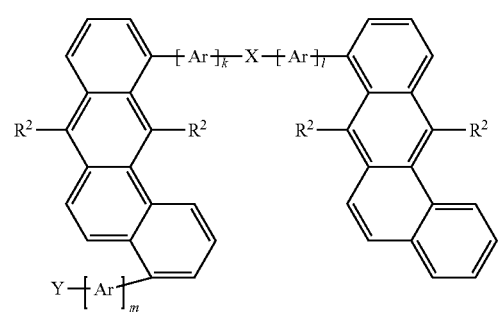
formula (17)
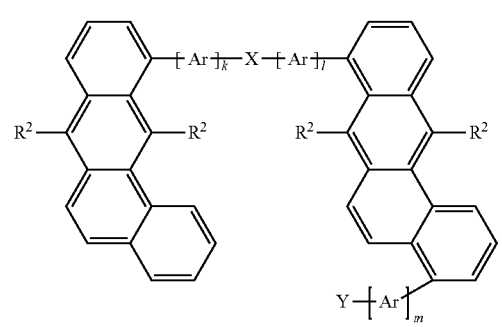

formula (18)

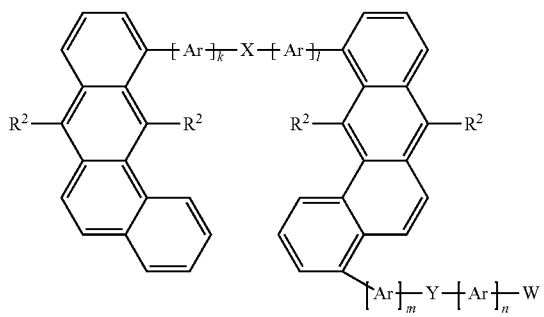

formula (19)

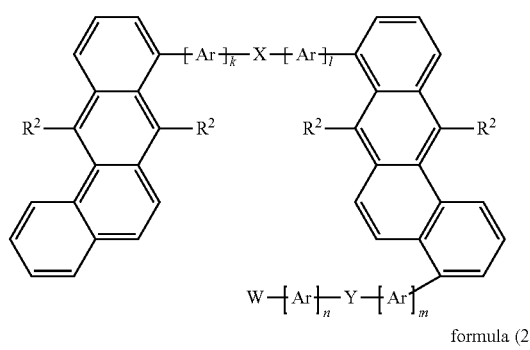

formula (20)

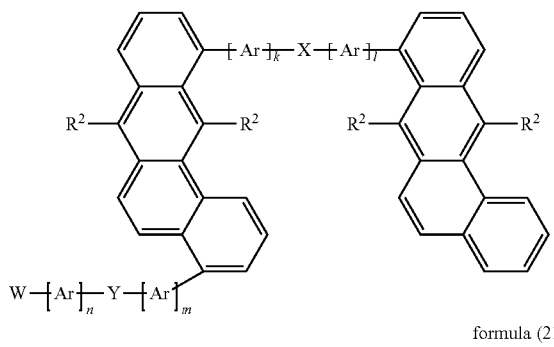

formula (21)

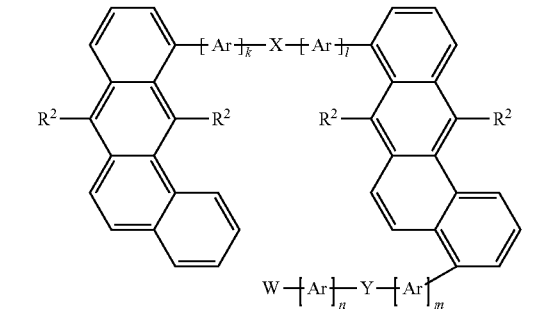

where the symbols and indices have the same meanings as described in the above embodiments, where the group X in the formulae (9) and (10) and the group Y in the formulae (14) to (17) in each case stands for a monovalent aromatic or heteroaromatic ring system or a group $N(Ar^1)_2$, where $R^2$ has the same meaning as R, with the proviso that both $R^2$ in a benz[a]anthracene are either equal to H or not equal to H, and where W is a group of the following formula (22) or (23):

formula (22)

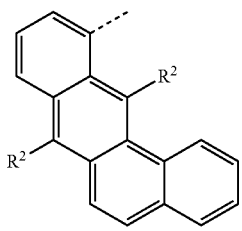

formula (23)

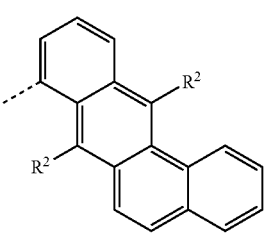

where the dashed line in formula (22) or (23) denotes the position in which this group is bonded to Ar or Y.

In compounds of the formulae (9) to (23), in each case a further substituent R other than hydrogen may be bonded in the 4-position or 5-position of the benzanthracene.

In still a further embodiment of the present invention, the group(s) X and/or Y of the above embodiments is (are) preferably built up from the groups benzene, naphthalene, anthracene, carbazole, phenanthrene, benzanthracene, chrysene, pyrene, phenanthroline, phenanthrimidazole, 1,3,5-triazine, benzimidazole, thiophene, benzothiophene, pyrazine, pyrimidine, pyridazine or triarylamine, in particular triphenylamine, or, if p=0 and/or q=0, represent(s) a group $N(Ar^1)_2$.

In still a further embodiment of the present invention, the group X in the compounds where p=0 and the group Y in the compounds where q=0 are selected from the units of the following formulae (24) to (36):

formula (24)

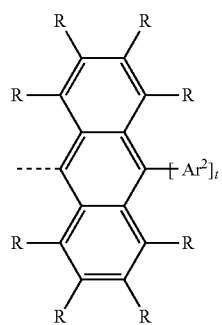

formula (25)

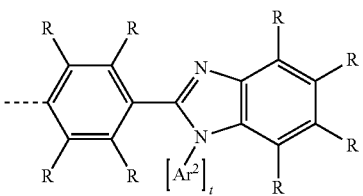

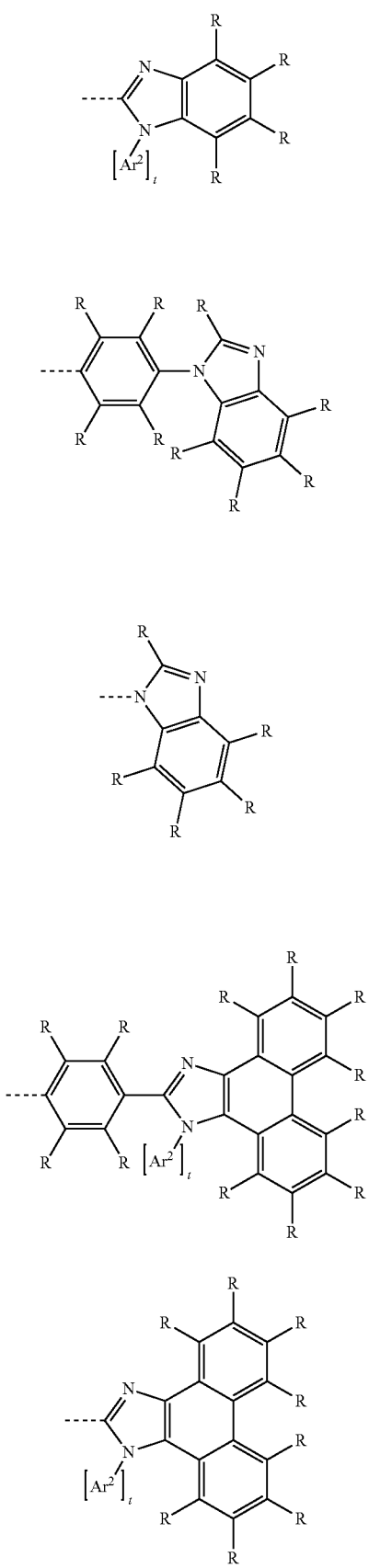

formula (26)

formula (27)

formula (28)

formula (29)

formula (30)

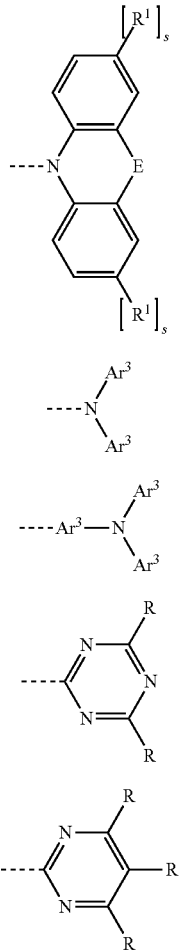

formula (31)

formula (32)

formula (33)

formula (34)

formula (35)

formula (36)

where R and $R^1$ have the meanings indicated in the above embodiments, and furthermore:

$Ar^2$ is an aryl or heteroaryl group having 5 to 16 aromatic ring atoms, preferably phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole, 2-fluorenyl, 2-spirobifluorenyl, fluoranthenyl, 2-benz[a]-anthracenyl, 3-benz[a]anthracenyl, 4-benz[a]anthracenyl, 5-benz[a]-anthracenyl or 6-benz[a]anthracenyl, each of which may be substituted by one or more radicals $R^1$, or, in formula (24), a group of the formula (31) or (32);

$Ar^3$ is, identically or differently on each occurrence, an aryl or heteroaryl group having 5 to 20 aromatic ring atoms or a triarylamine group having 15 to 30 aromatic ring atoms, each of which may be substituted by one or more radicals $R^1$, preferably an aryl or heteroaryl group having 6 to 14 aromatic ring atoms or a triarylamine group having 18 to 30 aromatic ring atoms, preferably having 18 to 22 aromatic ring atoms, each of which may be substituted by one or more radicals $R^1$; two groups $Ar^3$ here may also be bridged by a group E;

E stands for a single bond, O, S, N(R$^1$) or C(R$^1$)$_2$, where the two radicals R$^1$ on a group C(R$^1$)$_2$ may also form a spiro system through ring formation;

t is 1, 2 or 3;

s is on each occurrence, identically or differently, 0 or 1, where t is intended to denote how many groups Ar$^2$ occur successively, i.e. in the case where t is equal to 1, Ar$^2$ is a terminal monovalent group, in the case where t is equal to 2, a group Ar$^2$ is a divalent group to which the second group Ar$^1$ is bonded as a monovalent terminal group, or in the case where t is equal to 3, the first and second units Ar$^2$ connected to one another are each a divalent unit and the third group Ar$^2$, which is bonded to the second group Ar$^2$, is a terminal monovalent unit. Particularly preferred systems for t=2 are ortho-biphenyl, meta-biphenyl, para-biphenyl, phenylene-1-naphthyl, phenylene-2-naphthyl, N-phenyl-2-benzimidazole, 2-fluorenyl and 2-spirobifluorenyl.

Ar$^3$ in formula (32) particularly preferably stands, identically or differently, for phenyl, 1-naphthyl, 2-naphthyl, 2-, 3- or 4-triphenylamine, 1- or 2-naphthyldiphenylamine, which may in each case be bonded via the naphthyl or phenyl group, or 1- or 2-dinaphthylphenylamine, each of which may be bonded via the naphthyl or phenyl group. These groups may each be substituted by one or more alkyl groups having 1 to 4 C atoms or by one or more cyclic or bicyclic alkyl groups having 3 to 8 C atoms or by fluorine or cyano.

Preference is furthermore given to compounds of the above embodiments in which, in compounds of the formulae (1) to (23), the symbol Ar stands, identically or differently on each occurrence, for an arylene or heteroarylene group which is selected from 1,2-phenylene, 1,3-phenylene, 1,4-phenylene, 1,4-naphthylene, 9,10-anthrylene, 2,7-phenanthrenylene, 3,6-phenanthrenylene, 1,6-pyrenylene, 2,7-pyrenylene, 2,6-pyridinylene, 2,5-pyridinylene, 2,2'-biphenyl, 3,3'-biphenyl, 4,4'-biphenyl, 2,7-fluorenyl or 2,7-spirobifluorenyl. It should expressly be emphasised at this point that the groups Ar in the formulae (1) to (8) and (11) to (21) can be selected identically or differently.

In still a further embodiment of the present invention, it is preferred for the symbol(s) X and/or Y in the compounds of the formulae (1) to (8) where p=1 and/or q=1 or of the formulae (11) to (21) each to stand, independently of one another, for a single bond or a divalent group selected from C=O, O, NAr$^1$, POAr$^1$, O—B(Ar$^1$)—O, a divalent alkylene group having 1 to 6 C atoms or a divalent aromatic or heteroaromatic ring system having 5 to 14 aromatic ring atoms; and for the symbol(s) X and/or Y in the compounds of the formulae (1) to (8) where p=2 and/or q=2 to stand for N or a trivalent aromatic or heteroaromatic ring system having 5 to 14 aromatic ring atoms, in particular for 1,3,5-benzene or 1,3,5-triazine; and for the symbol(s) X and/or Y in the compounds of the formulae (1) and (2) where p>2 and/or q>2 to stand for an aromatic or heteroaromatic ring system having 5 to 14 aromatic ring atoms of correspondingly higher valence.

In the compounds of the formulae (1), (3), (5), (7) and (11) to (13), all indices m and n may be selected identically, which results in symmetrical compounds, or they may be selected differently, which results in asymmetrical compounds. As already mentioned above, symmetrical compounds have the advantage of easier synthetic accessibility and asymmetrical compounds have the advantage of frequently more suitable physical properties.

Preference is furthermore given to compounds of the formulae (1) to (23) in which the indices m, n, k and l stand for 0.

Preference is furthermore given to compounds of the formulae (1) to (23) in which the index p or q stands for 0, 1 or 2, particularly preferably for 0 or 1.

If a radical R stands for an N(Ar$^1$)$_2$ group, this group is preferably selected from the groups of the formula (31) or of the formula (32) depicted above.

Examples of compounds of the formula (1) and (2) are shown below.

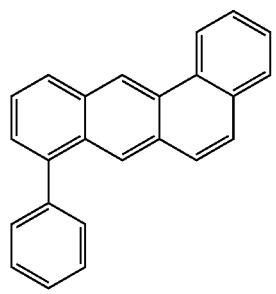

1

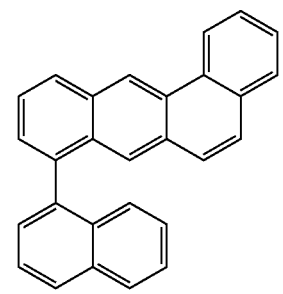

2

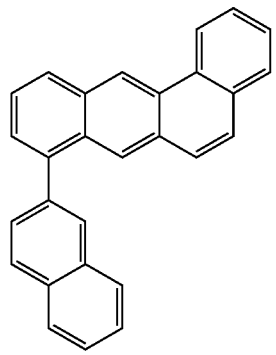

3

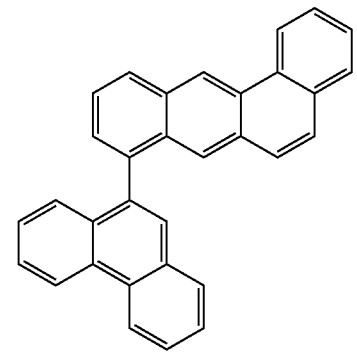

4

5
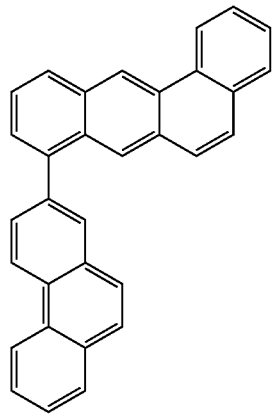
6
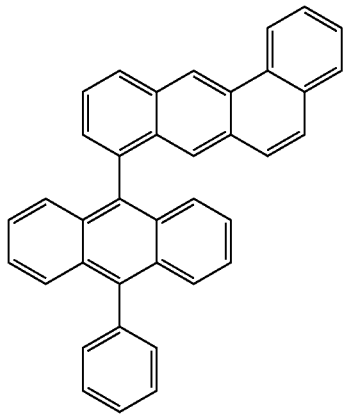
7
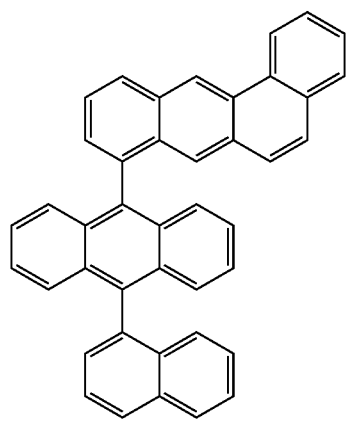
8
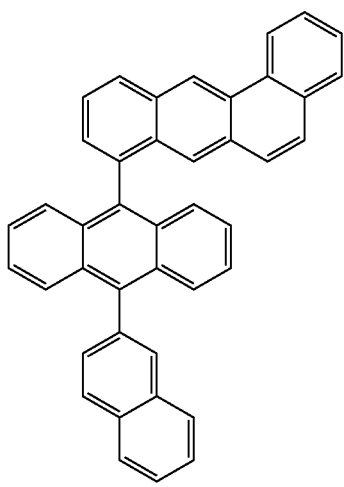
9
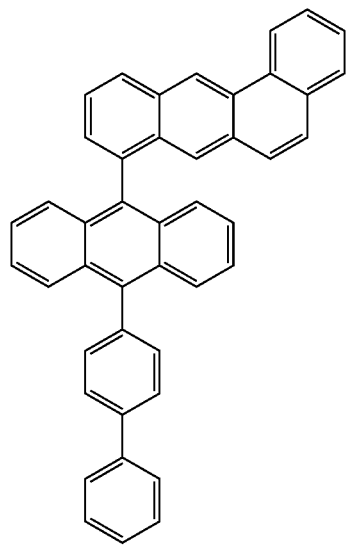
10
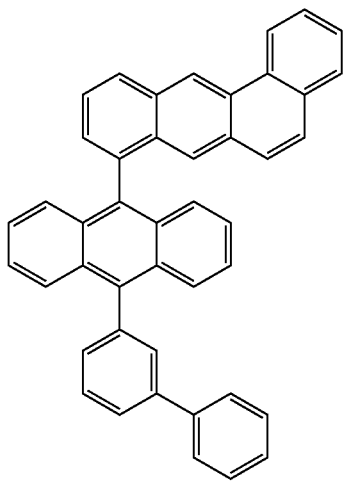

-continued
11
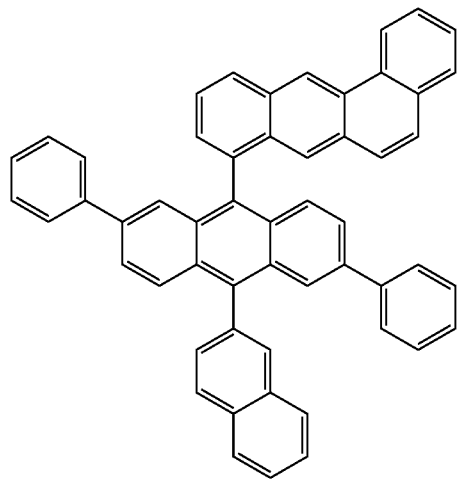
12
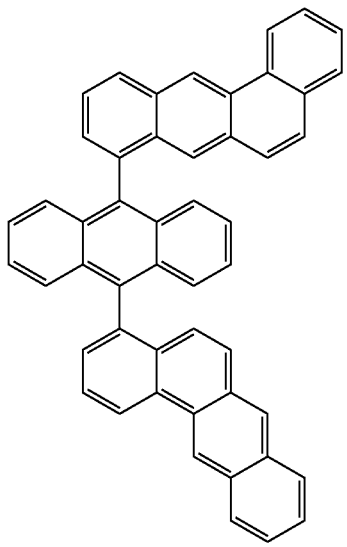
13
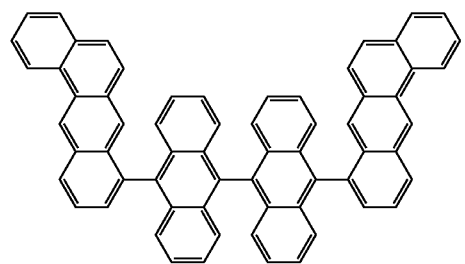
14
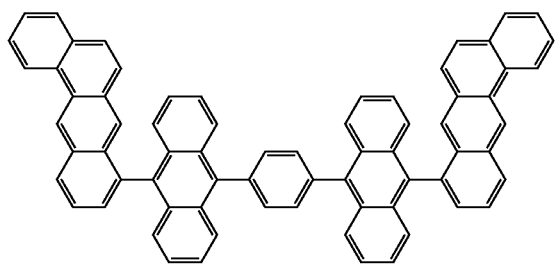
15
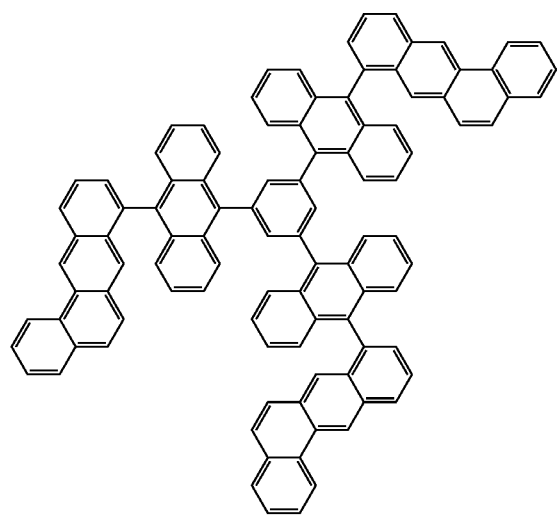
16
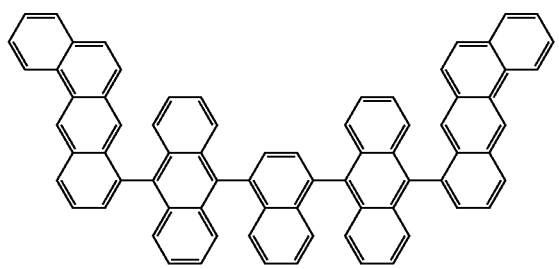

-continued
17
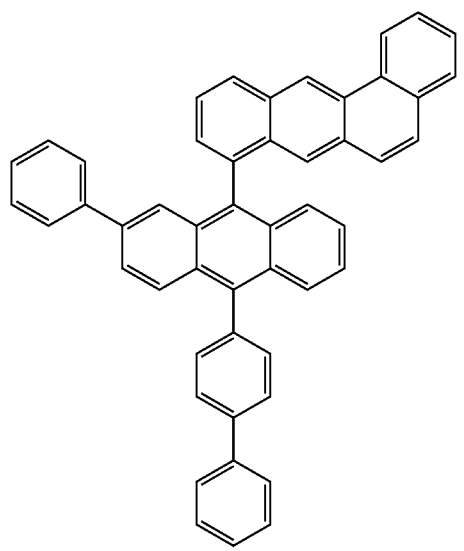
18
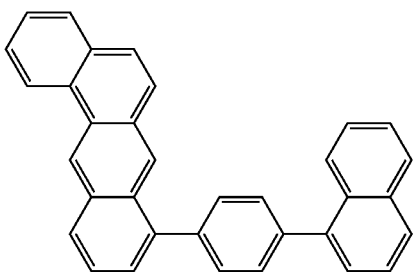
19
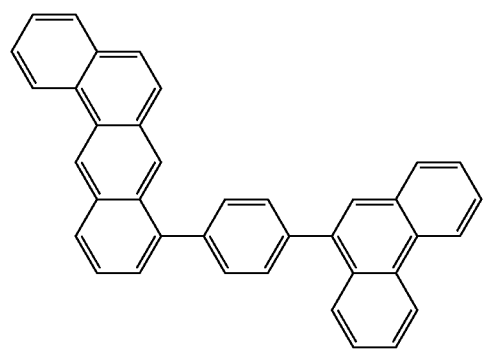
20
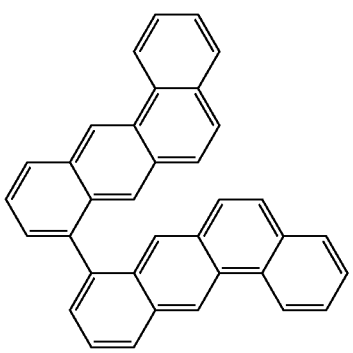
21
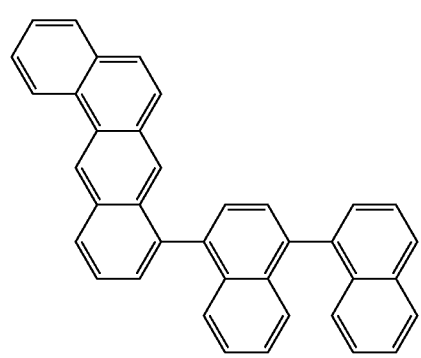
22
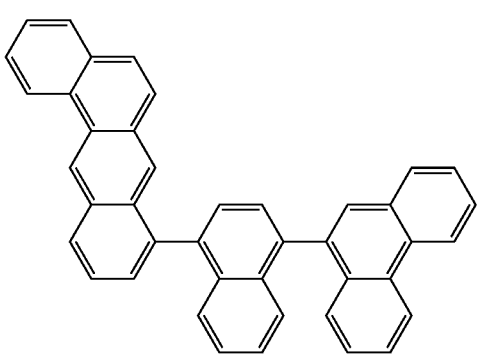
23
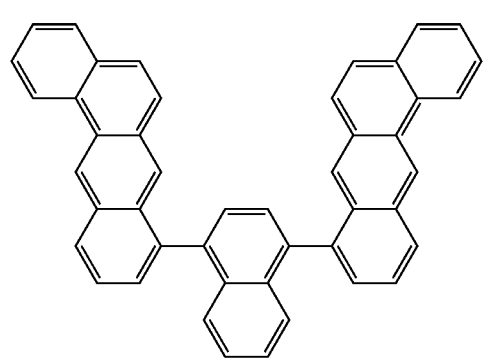
24
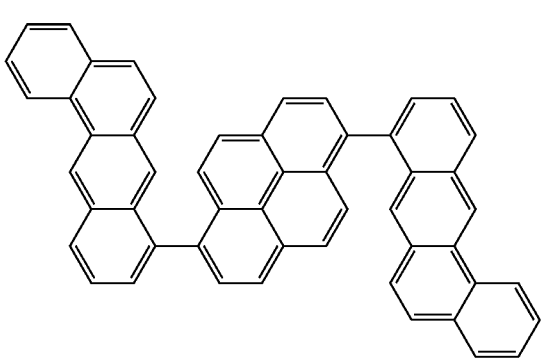

-continued
25
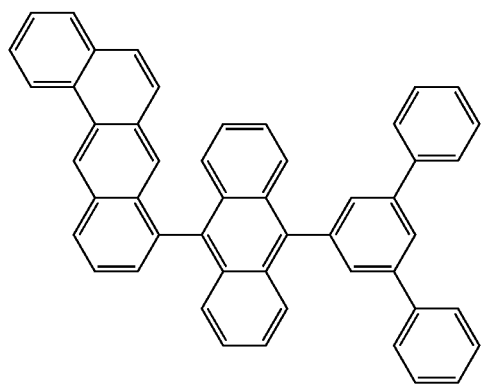
26
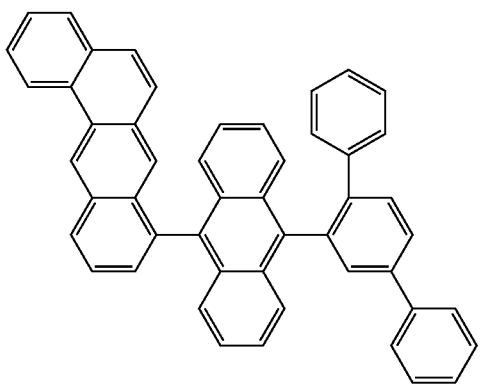
27
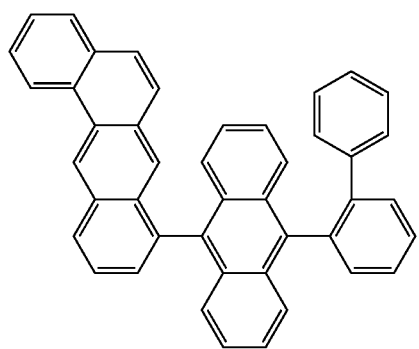
28
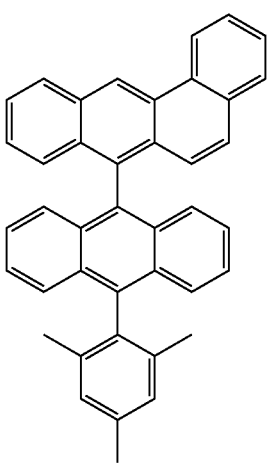
29
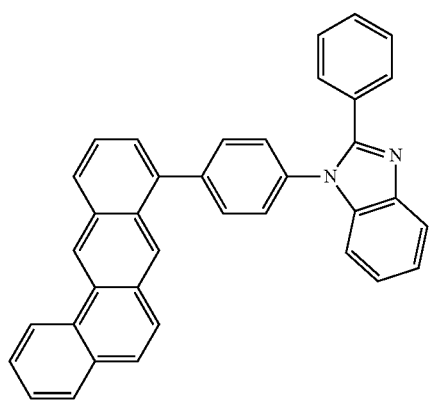
30
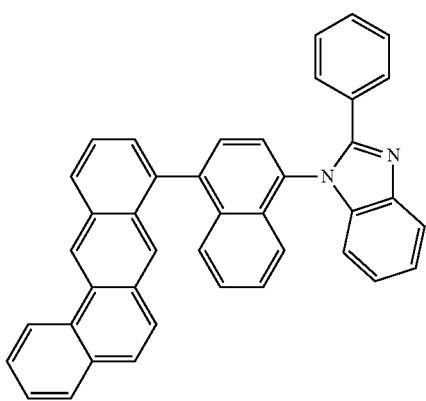

-continued
31
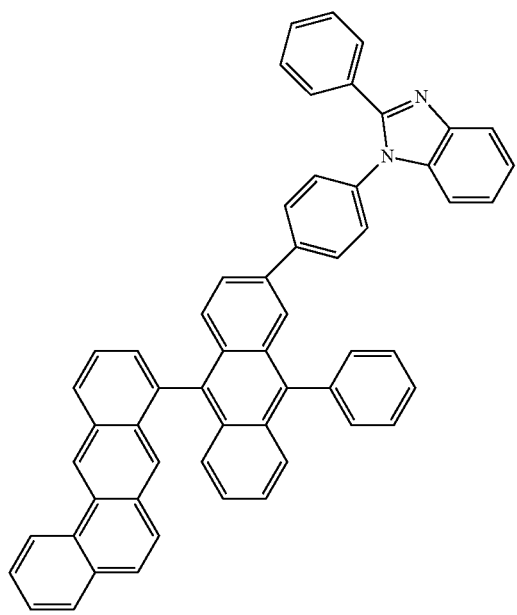
32
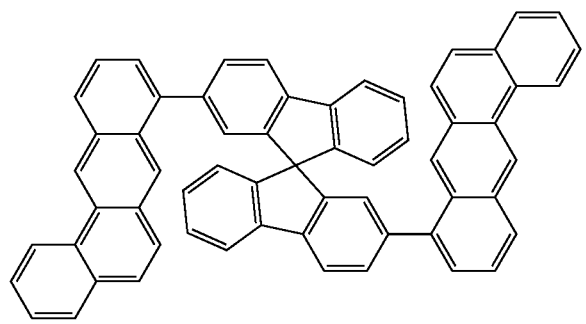
33
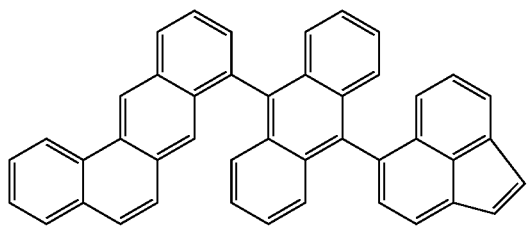
34
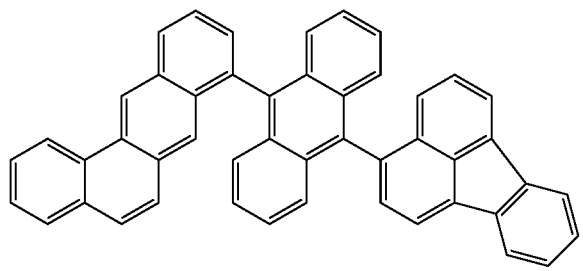
35
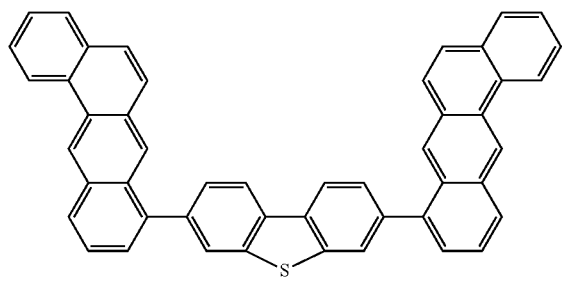
36
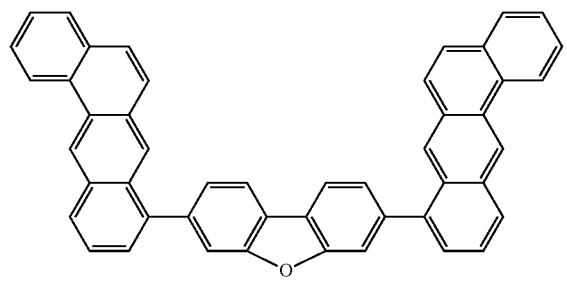
37
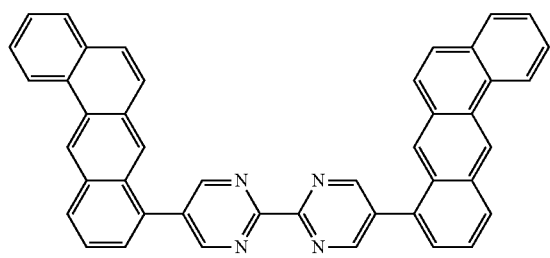
38
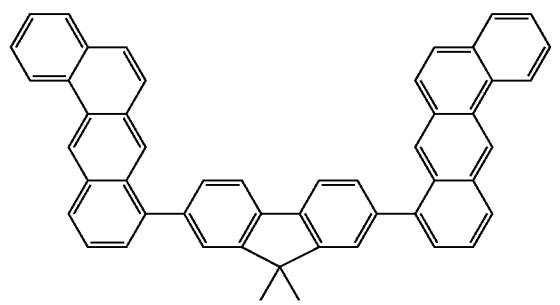

-continued
| | |
|---|---|
| 39 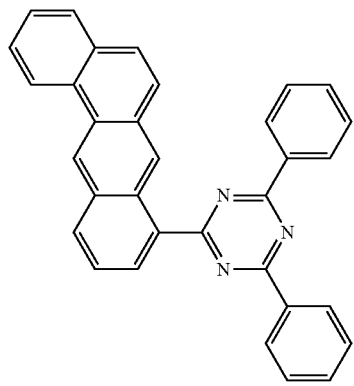 | 40 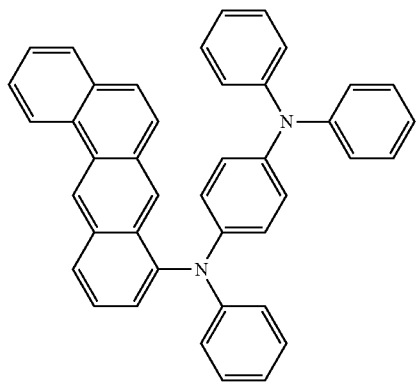 |
| 41 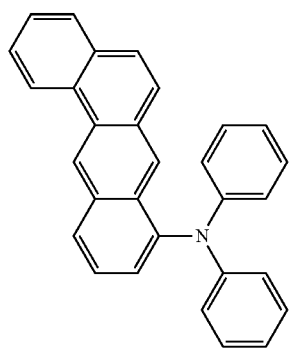 | 42 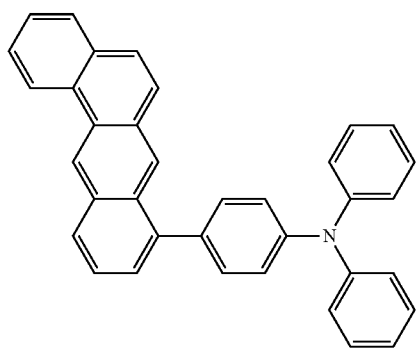 |
| 43 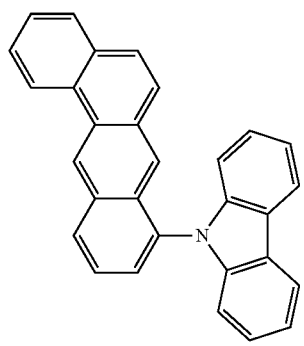 | 44 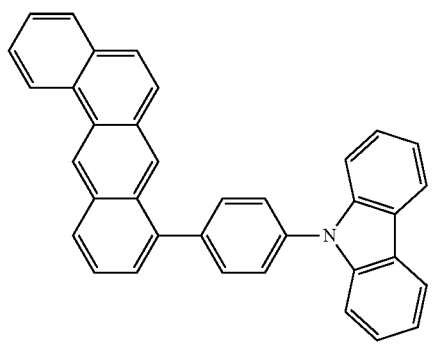 |
| 45 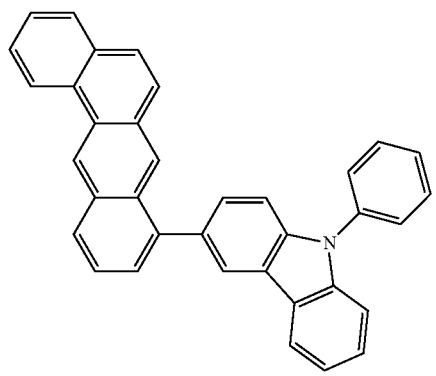 | 46 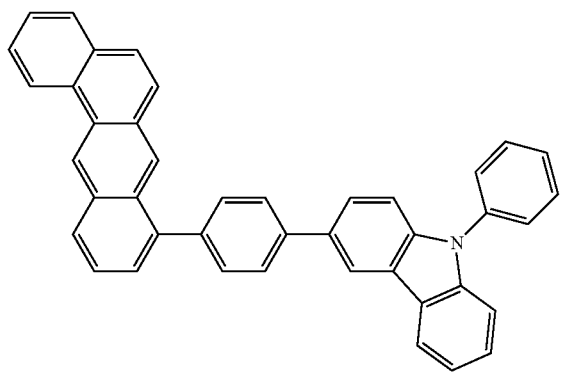 |

-continued
47
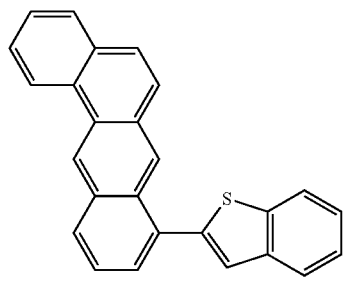
48
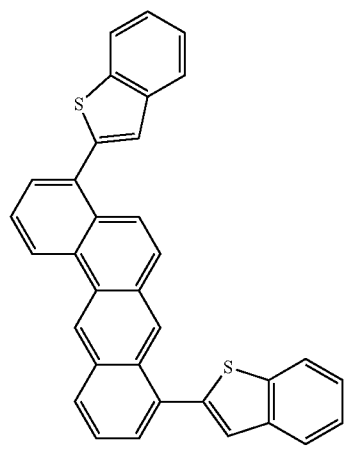
49
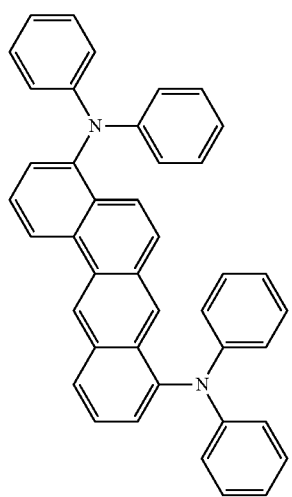
50
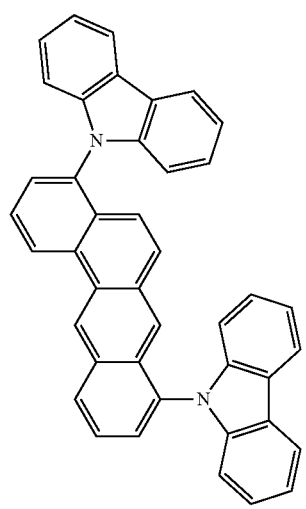
51
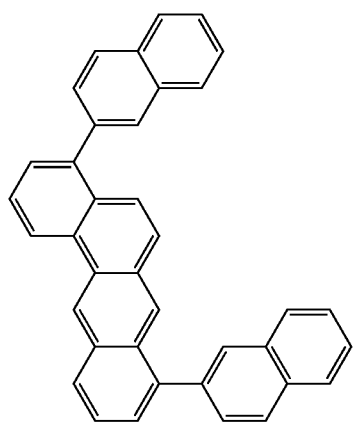
52
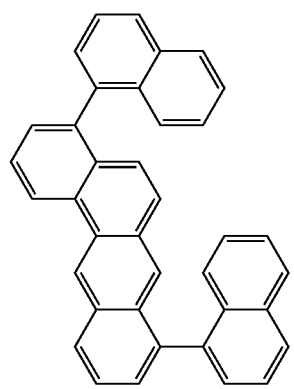

53
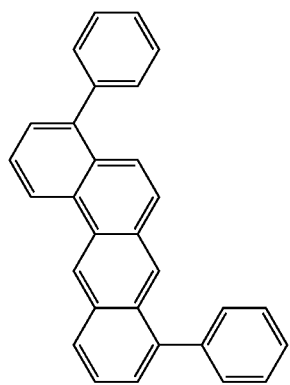
54
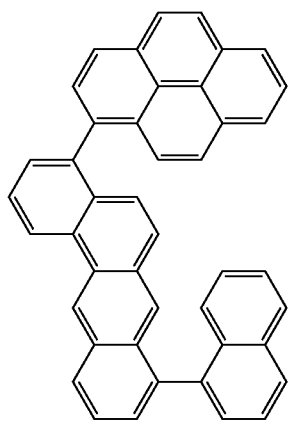
55
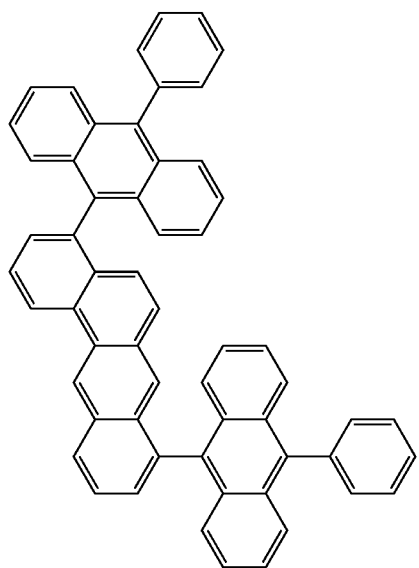
56
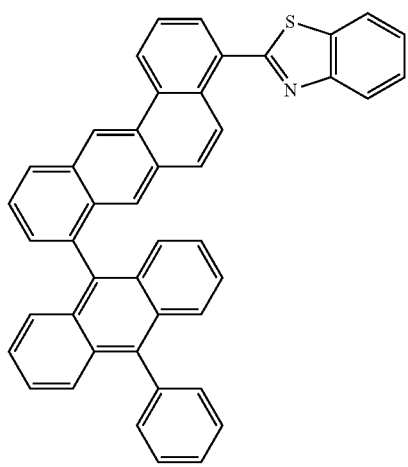
57
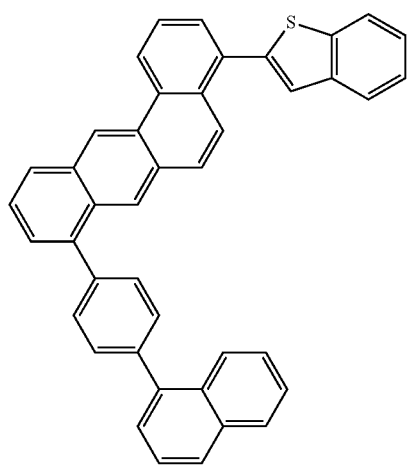
58
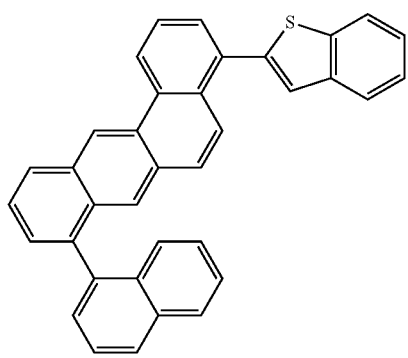

-continued
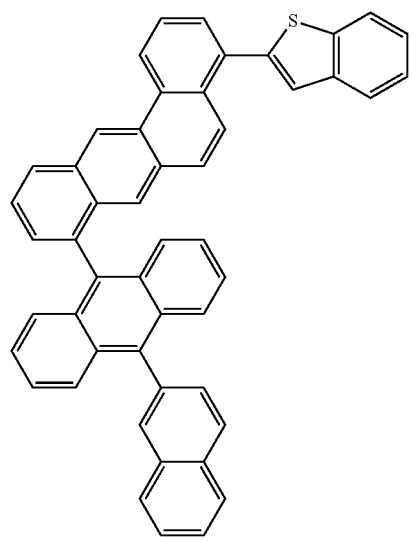
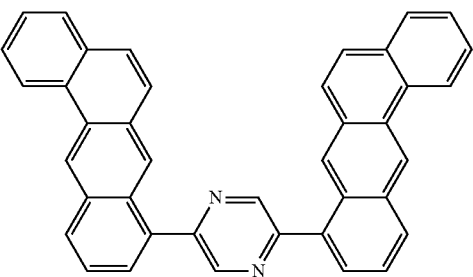
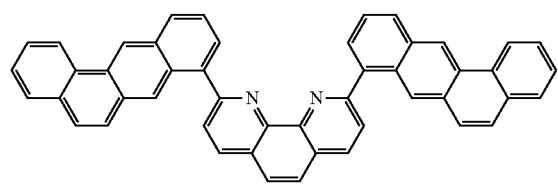
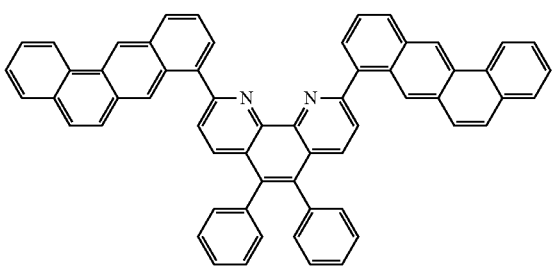
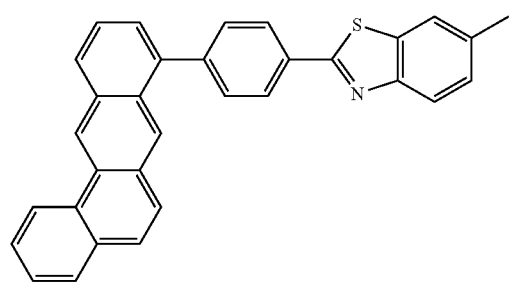
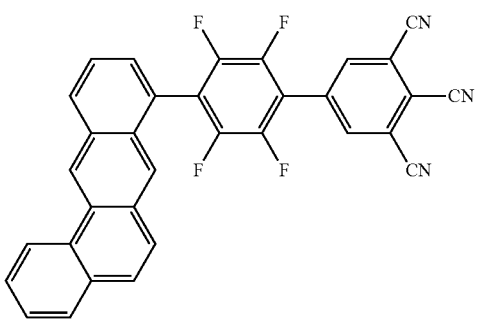
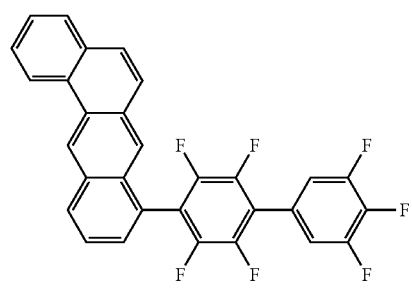
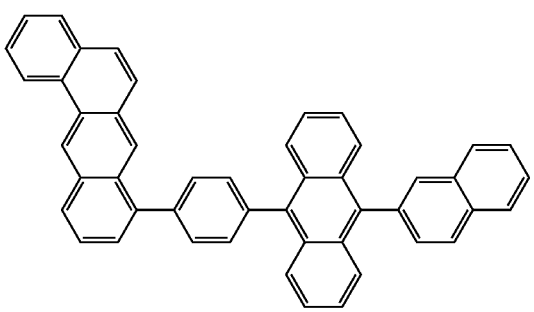

-continued
67
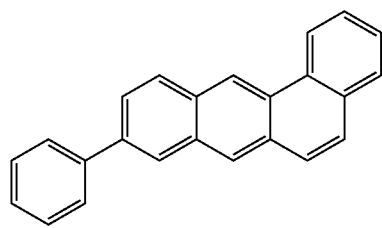
68
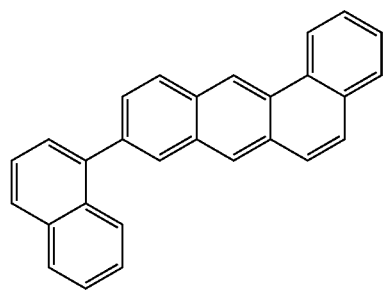
69
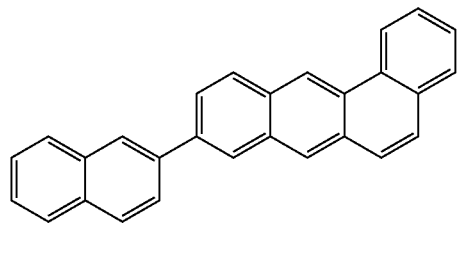
70
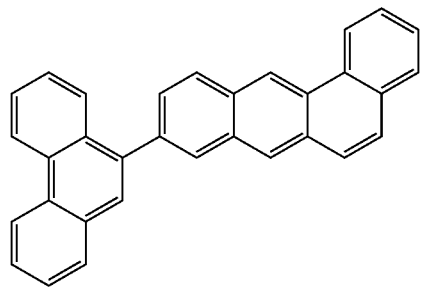
71
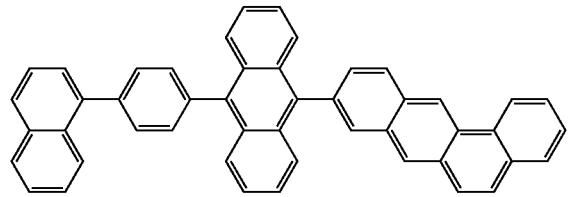
72
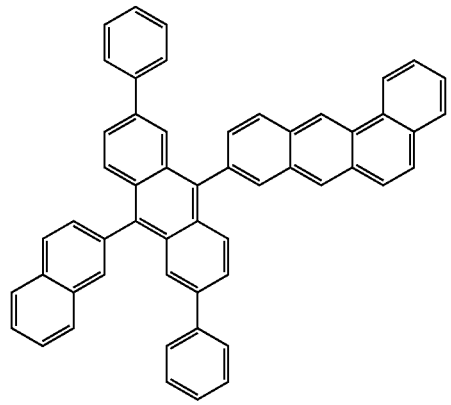
73
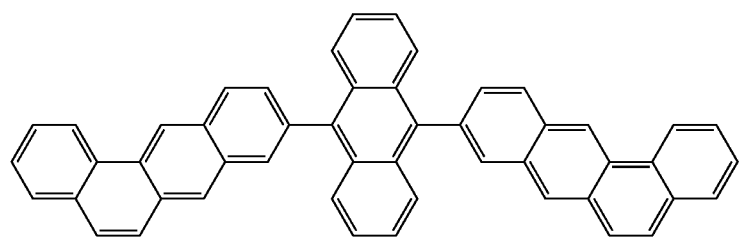
74
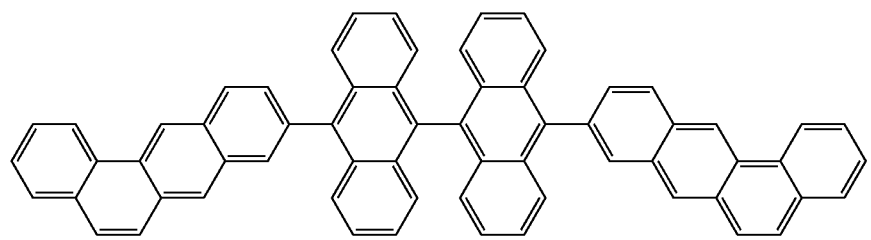

-continued
75
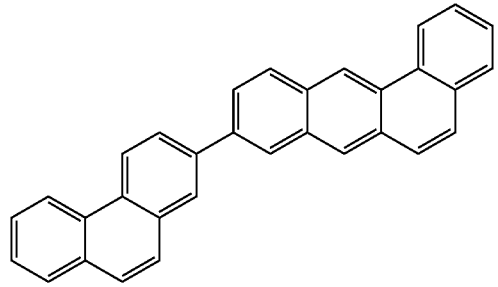
76
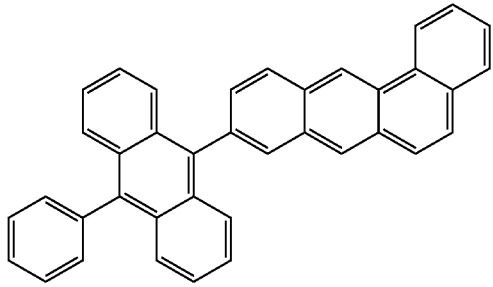
77
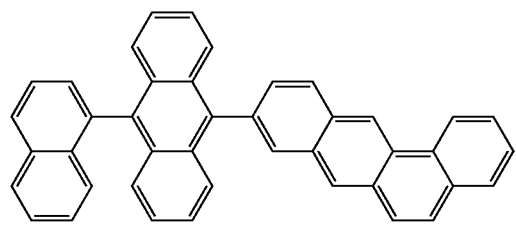
78
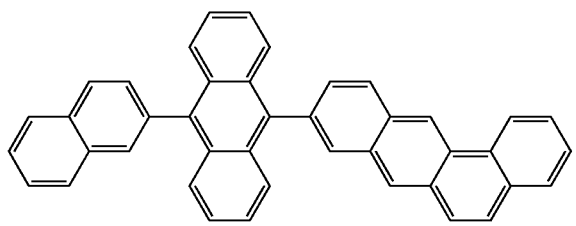
79
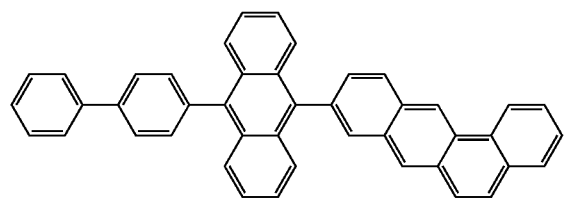
80
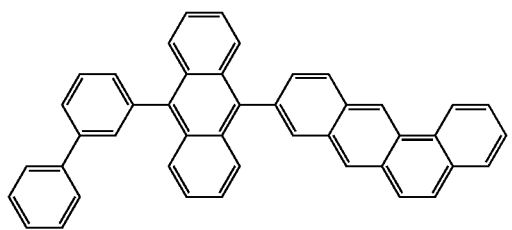
81
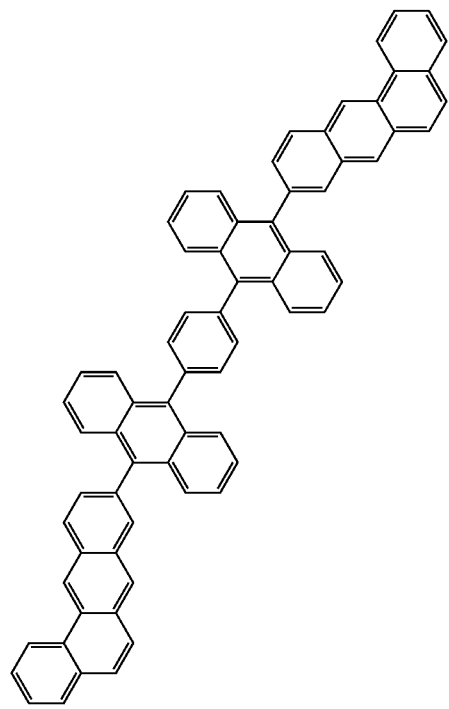

-continued
82
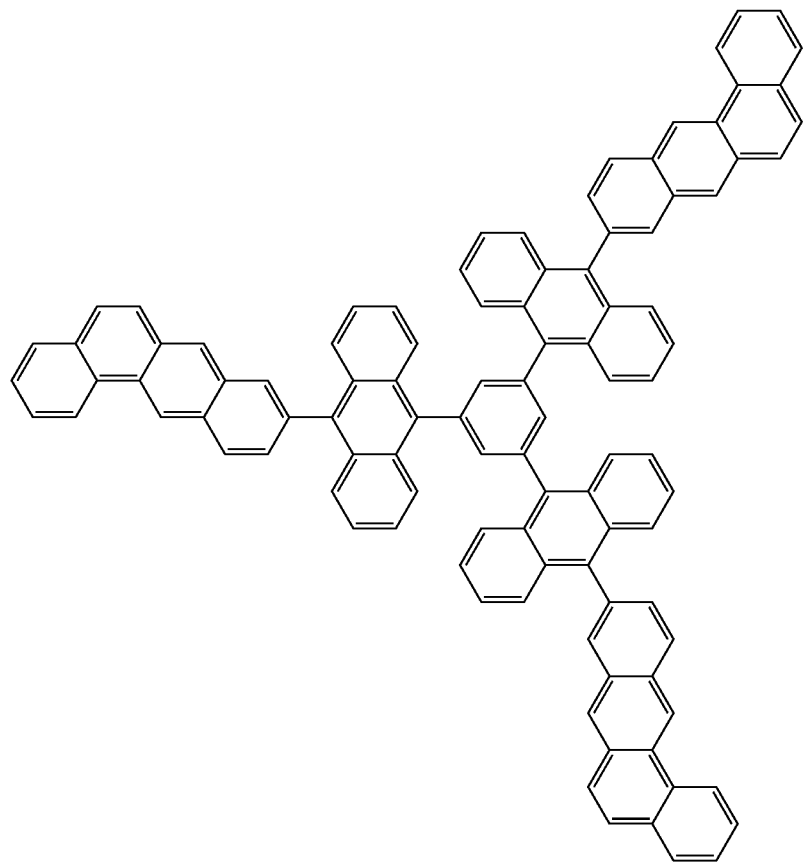
83
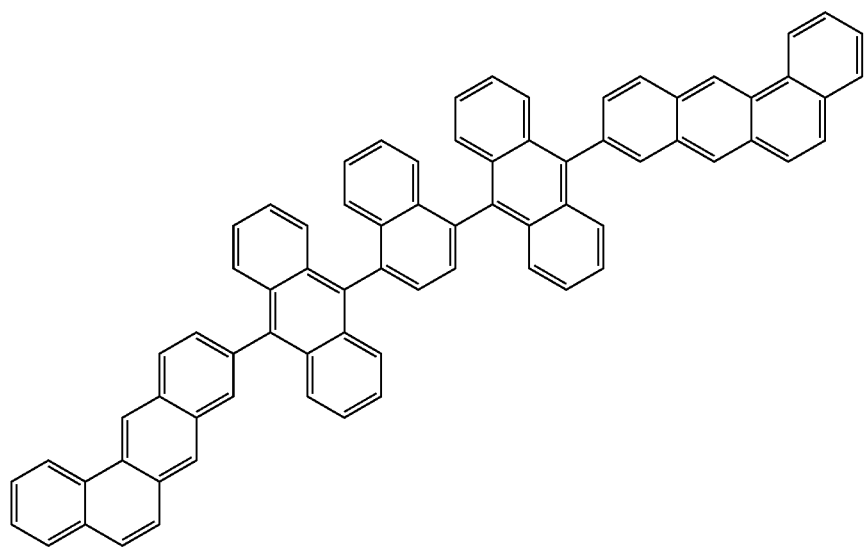

-continued
84
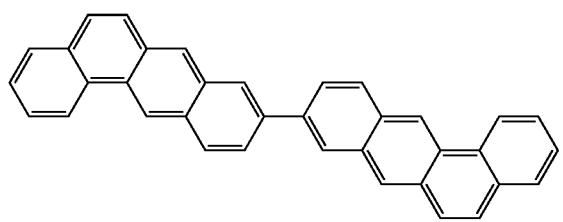
85
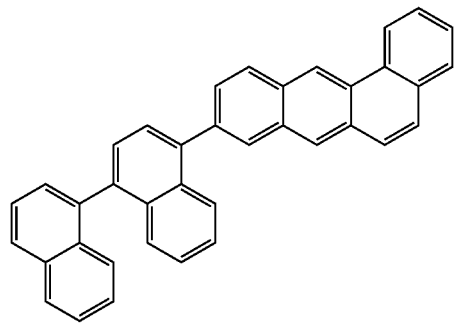
86
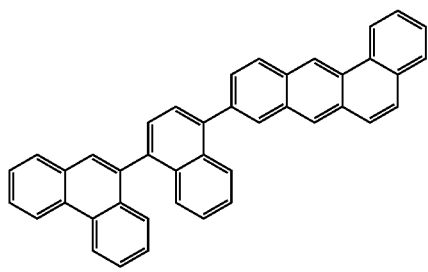
87
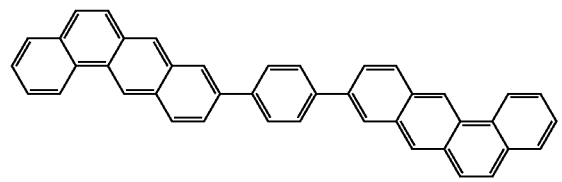
88
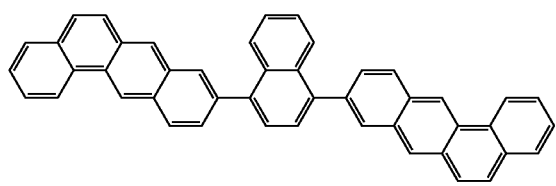
89
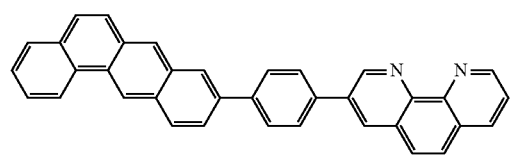
90
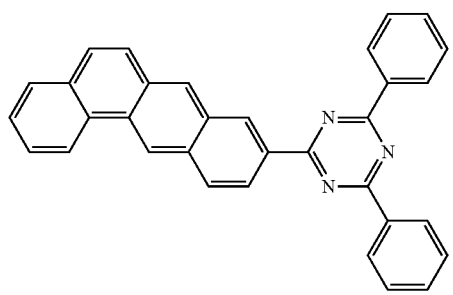
91
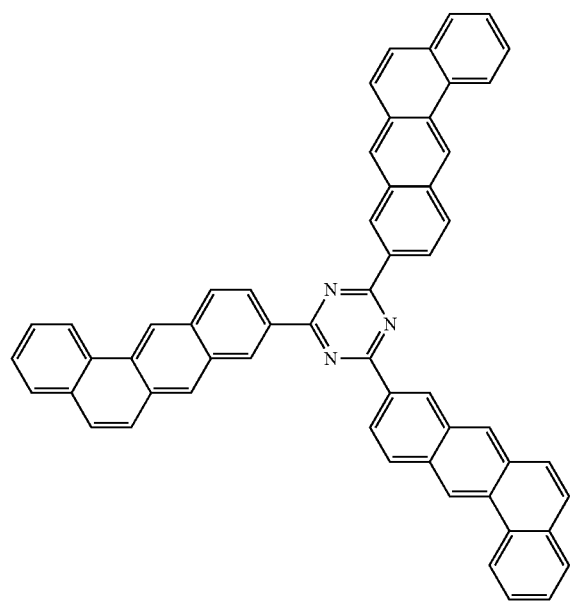

92
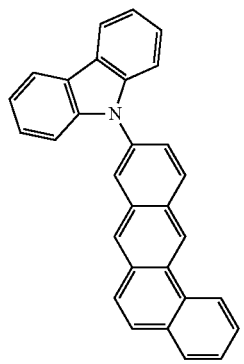
93
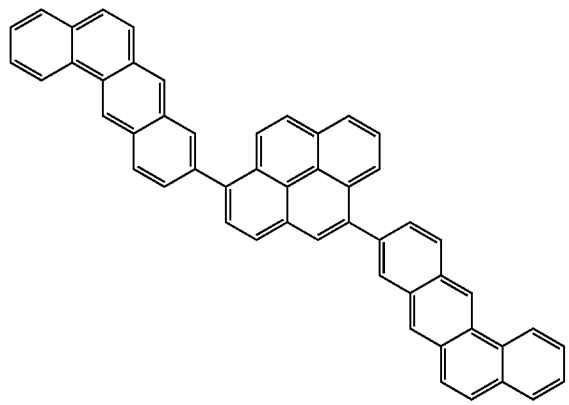
94
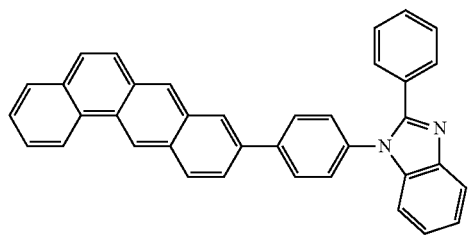
95
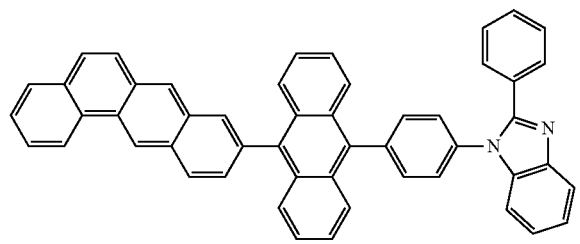
96
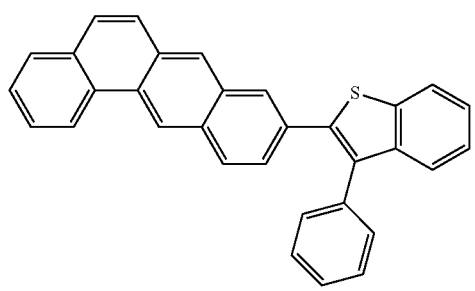
97
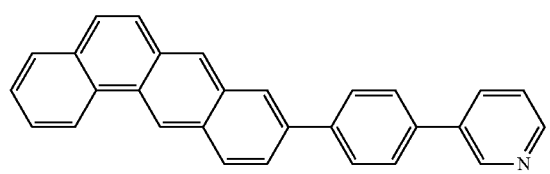
98
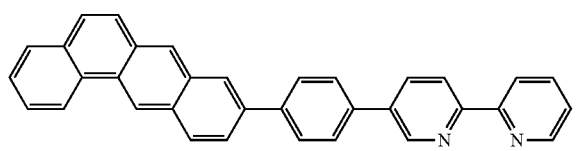
99
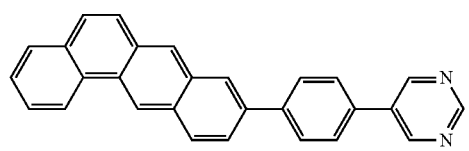
100
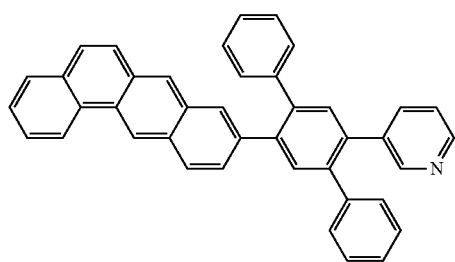
101
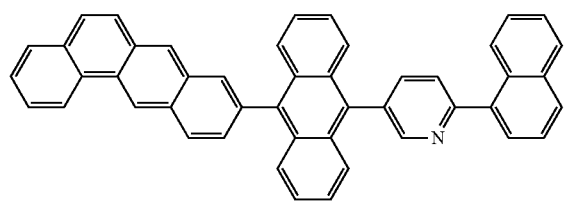

-continued
102
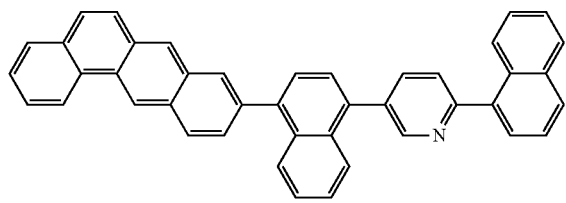
103
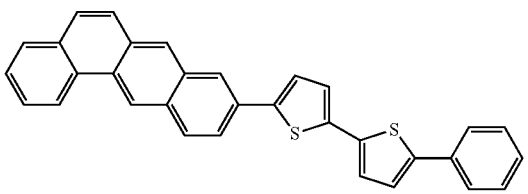
104
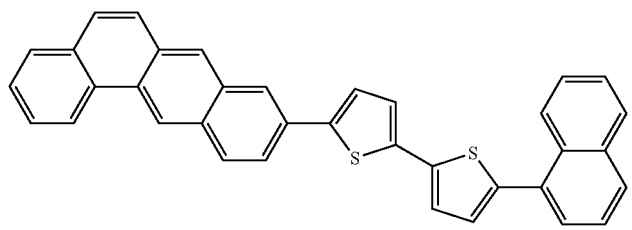
105
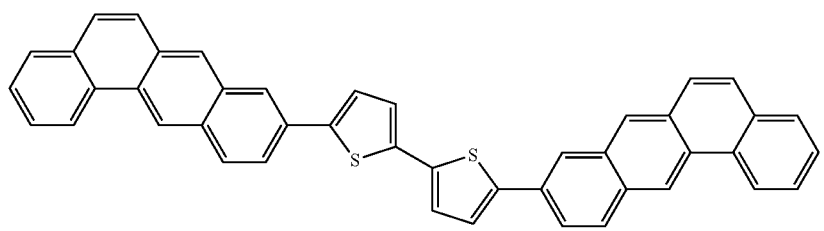
106
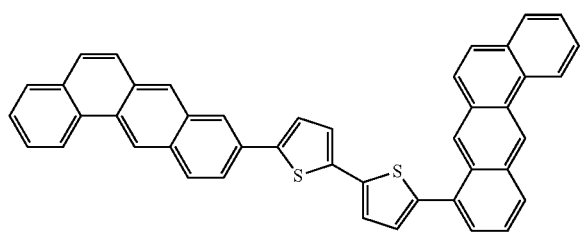
107
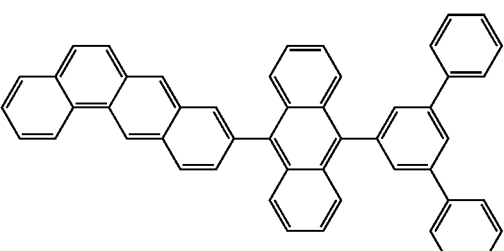
108
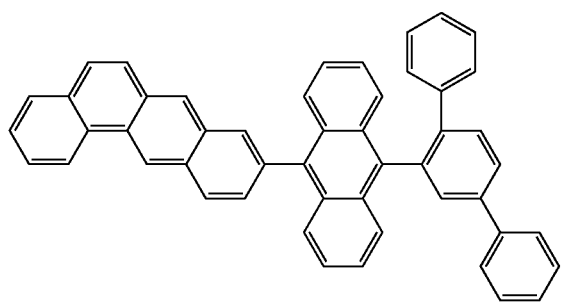
109
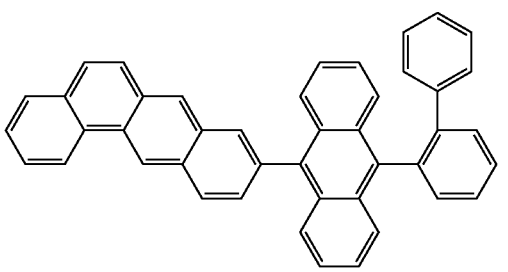
110
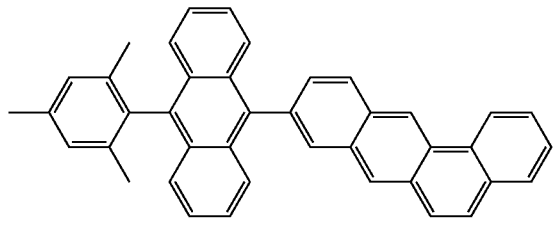
111
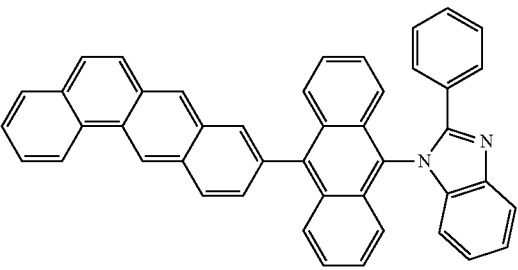

-continued
112
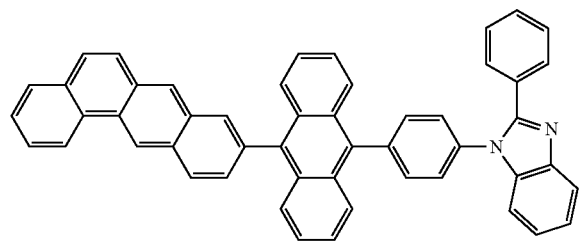
113
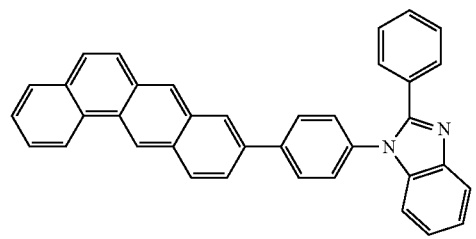
114
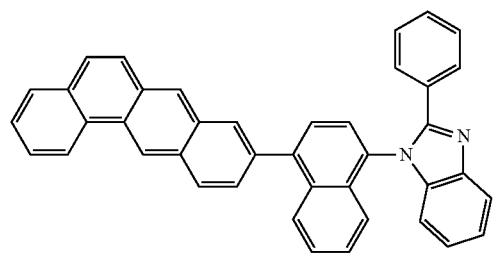
115
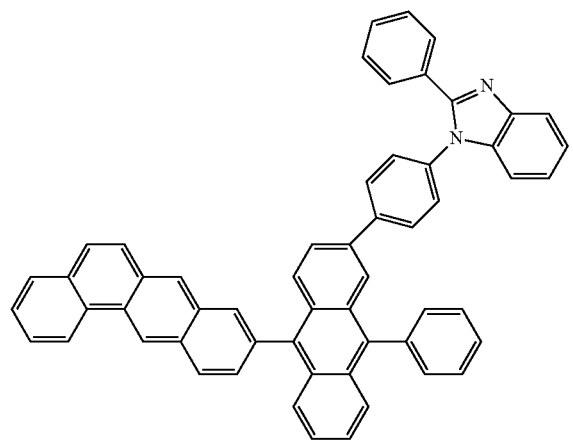
116
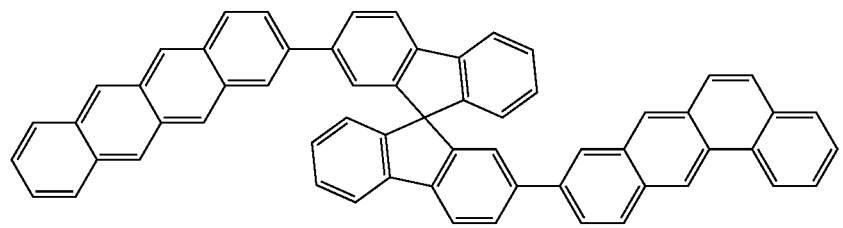
117
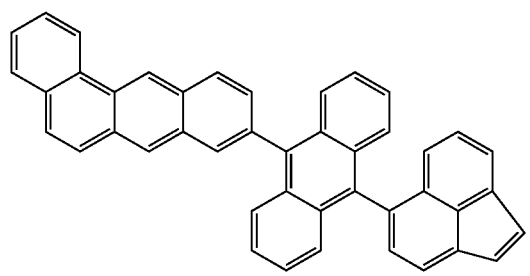
118
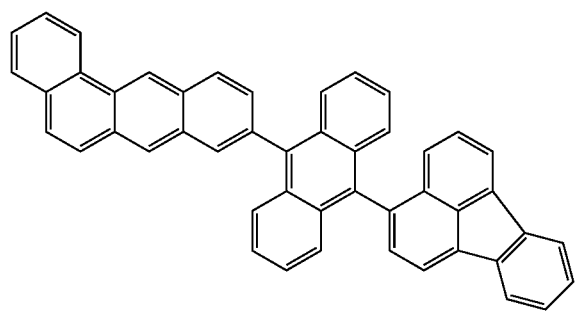
119
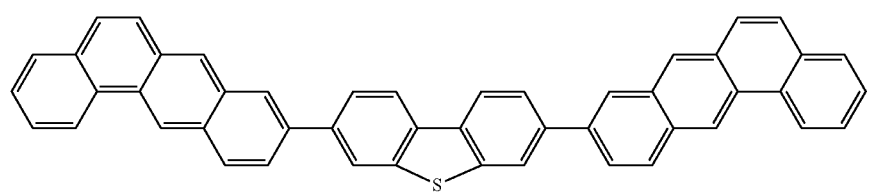

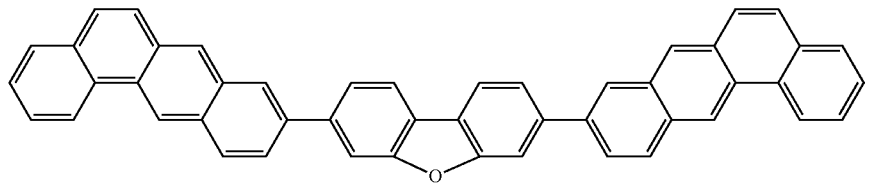
120
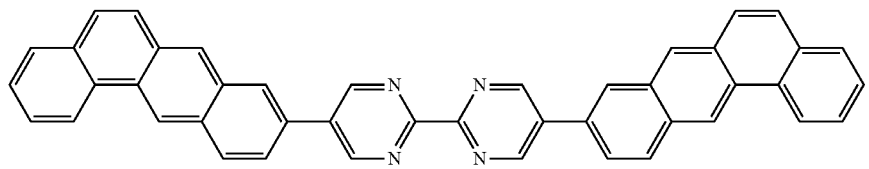
121
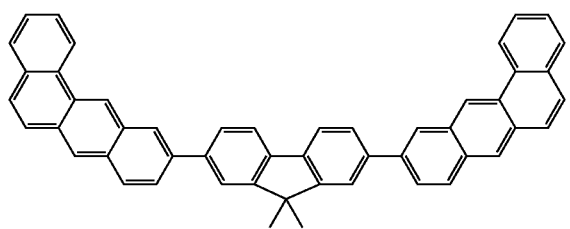
122
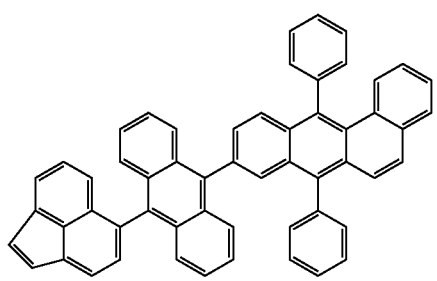
123
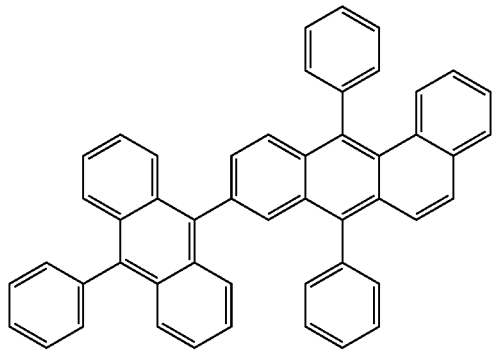
124
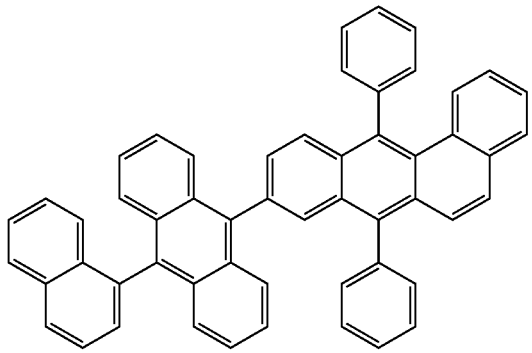
125
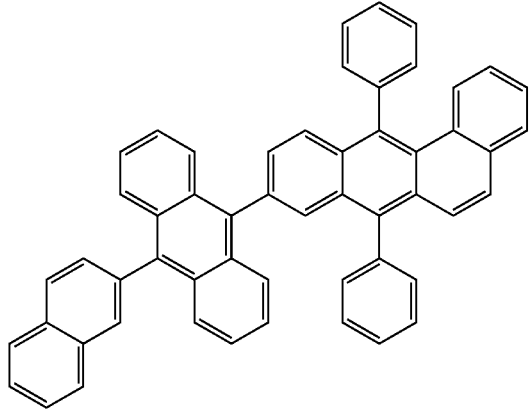
126
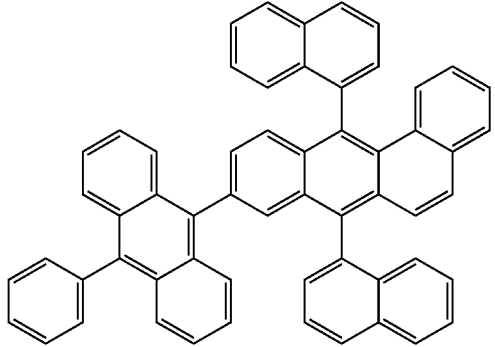
127

-continued
128
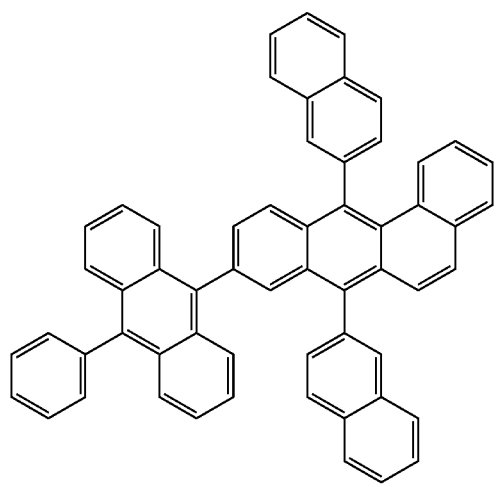
129
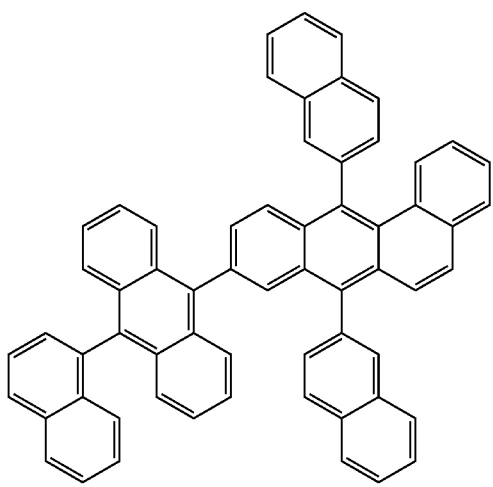
130
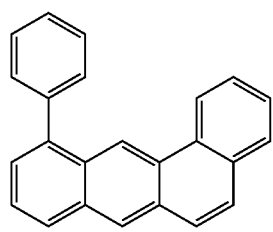
131
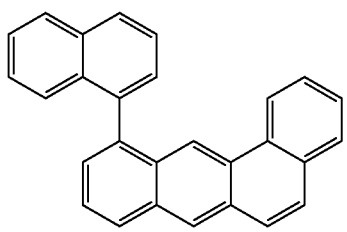
132
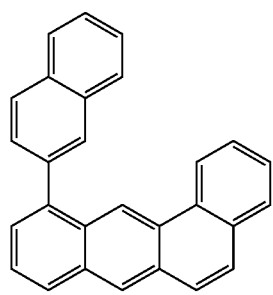
133
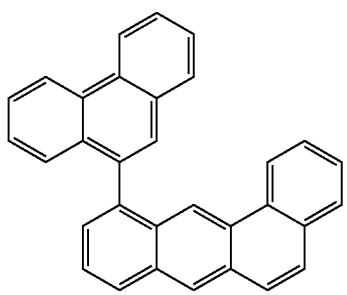
134
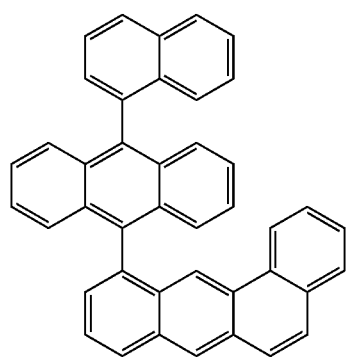
135
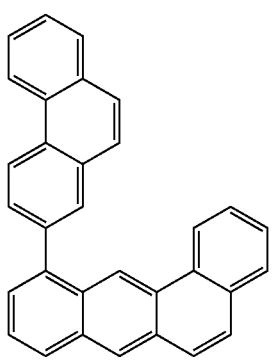

-continued
136
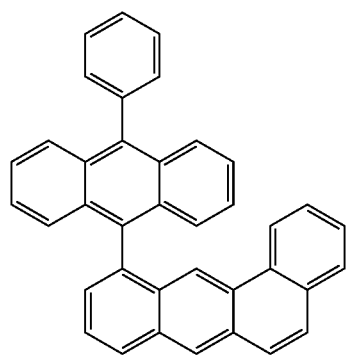
137
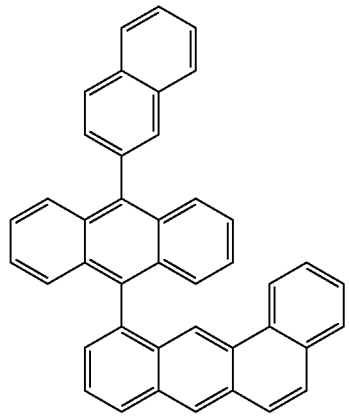
138
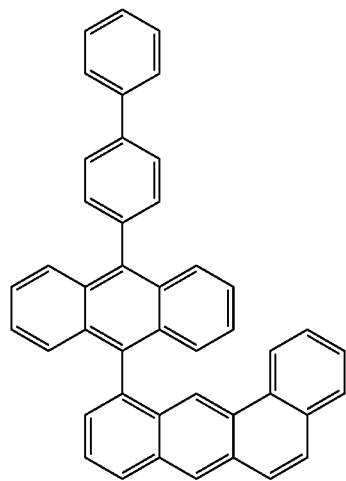
139
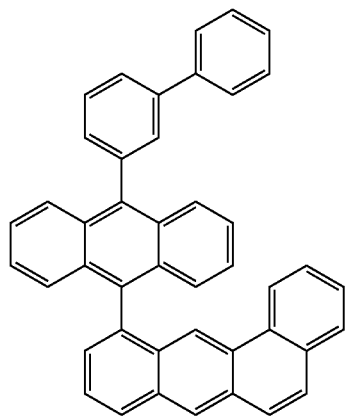
140
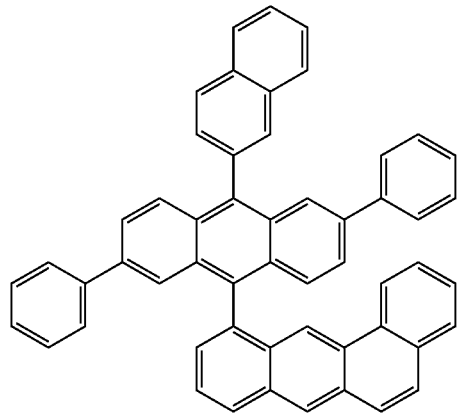
141
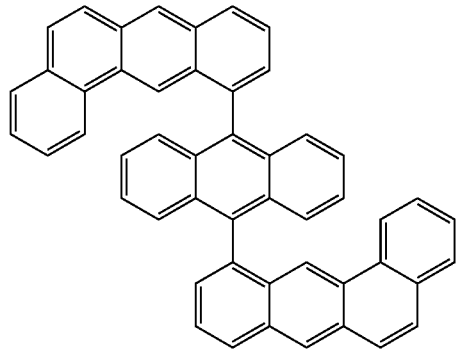

-continued
142
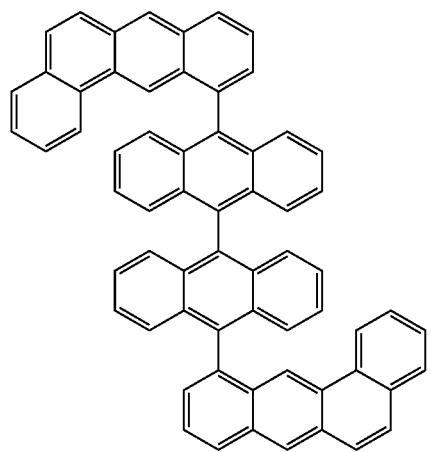
143
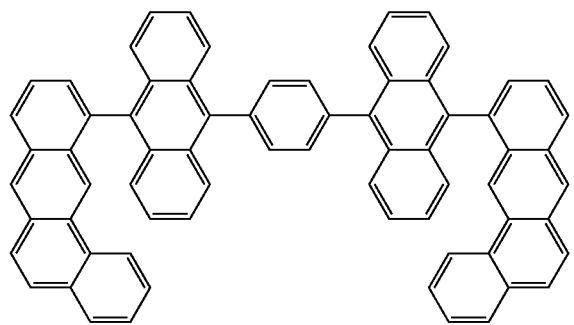
144
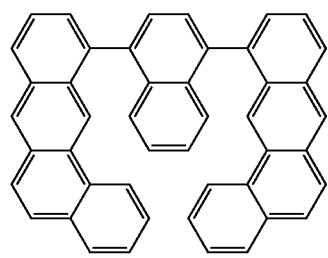
145
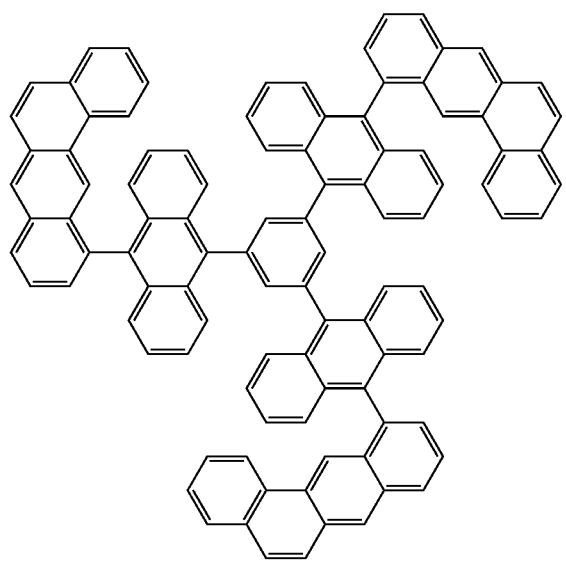
146
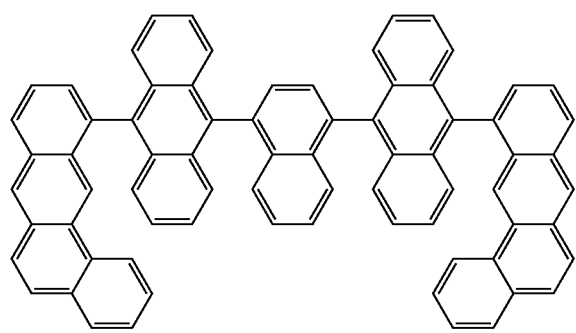
147
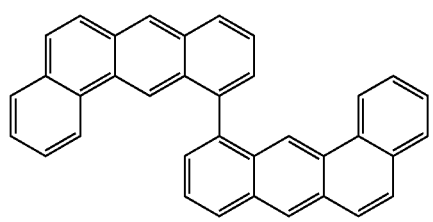

-continued
148 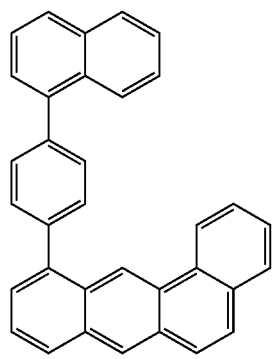
149 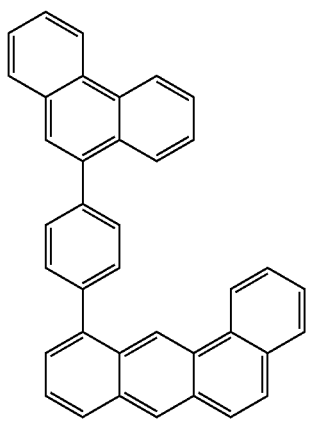
150 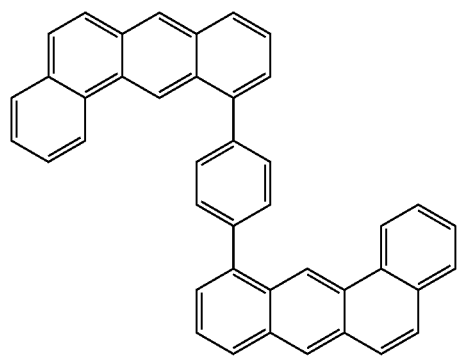
151 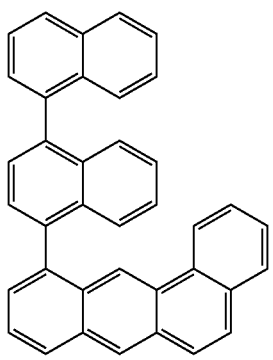
152 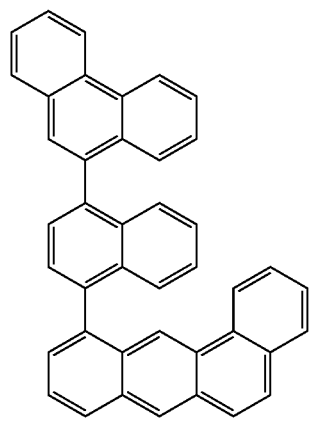
153 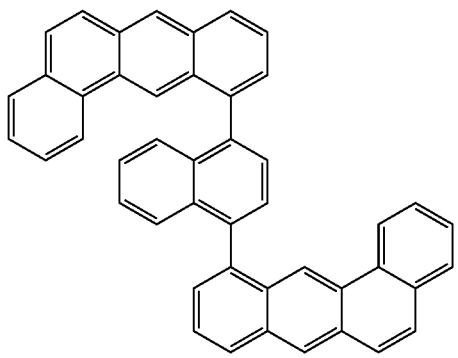
154 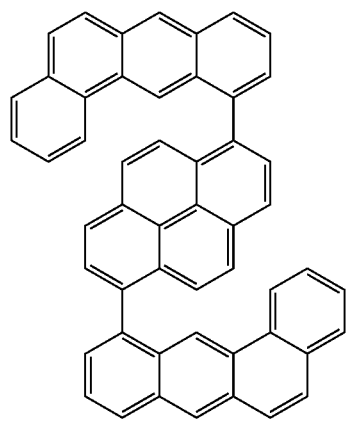
155 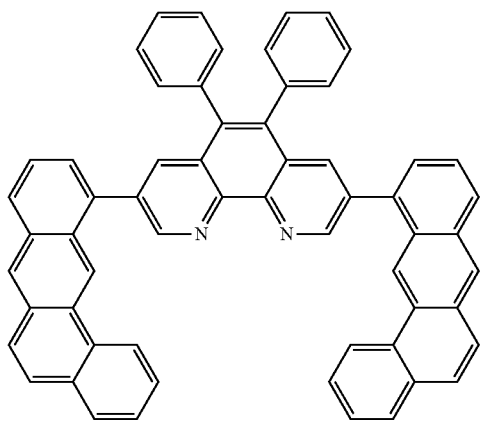

156
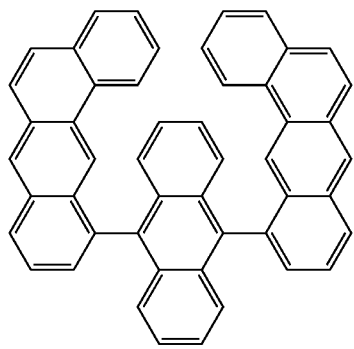
157
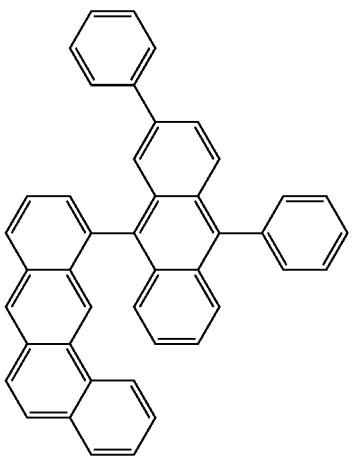
158
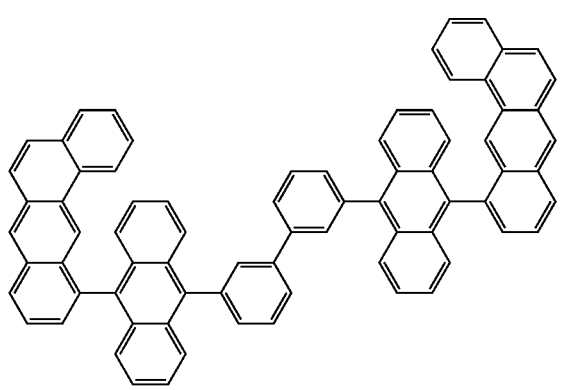
159
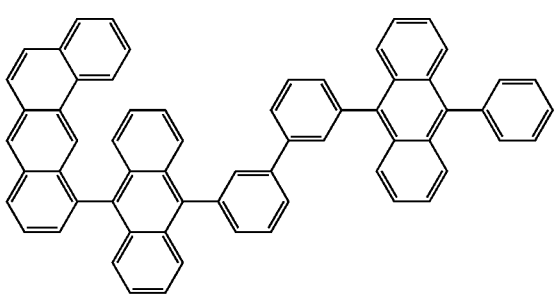
160
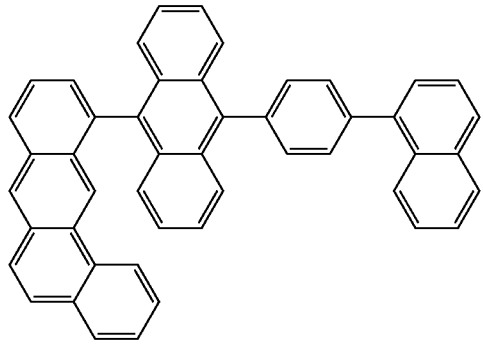
161
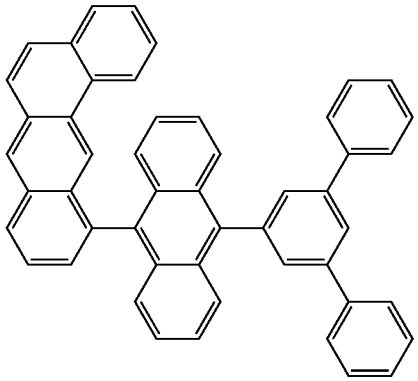
162
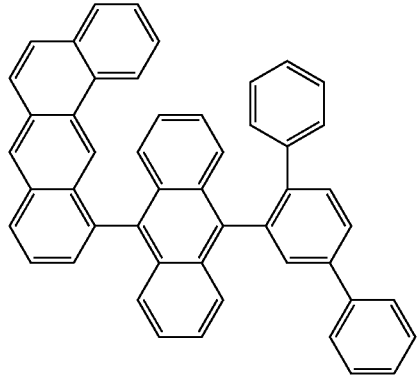
163
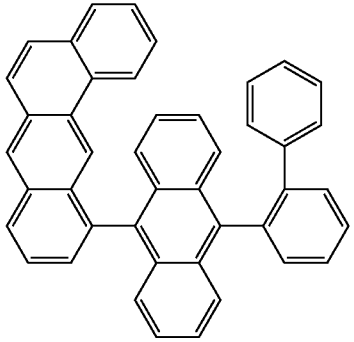

-continued
164
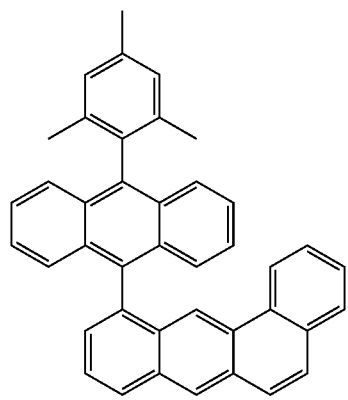
165
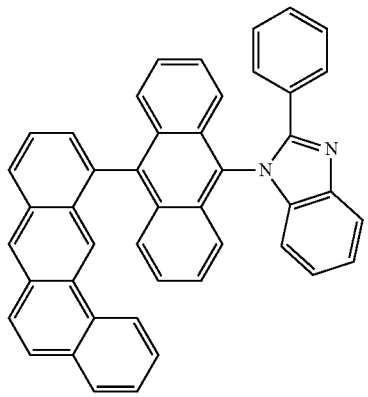
166
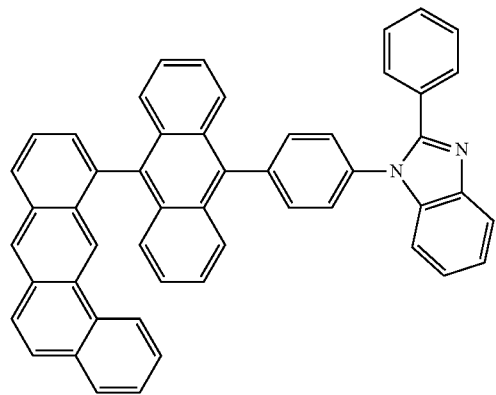
167
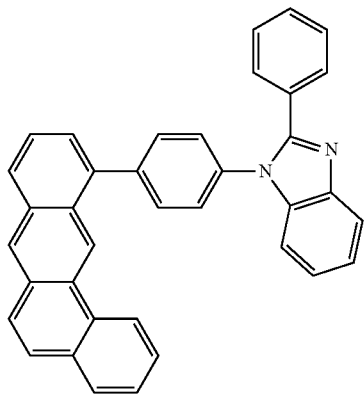
168
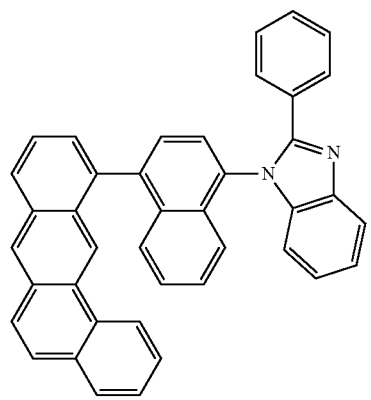
169
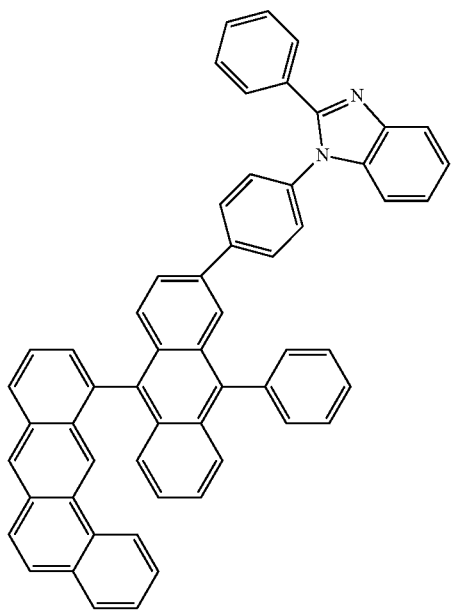

-continued
170 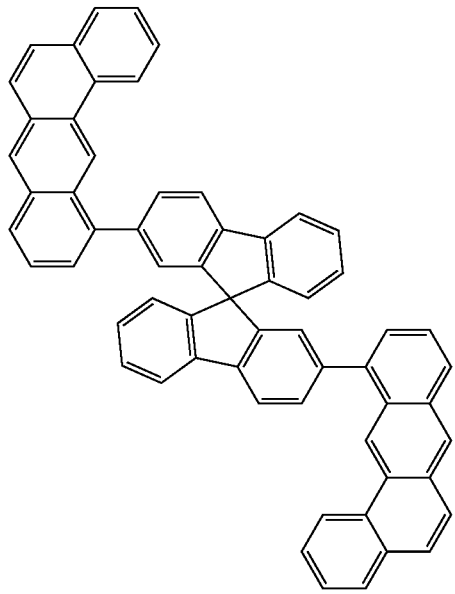 171 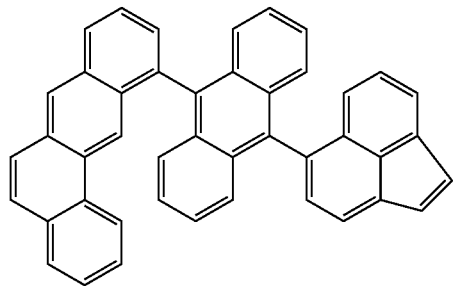
172 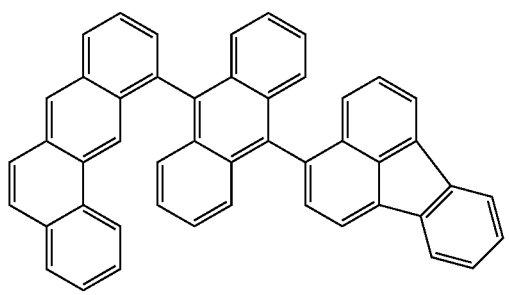 173 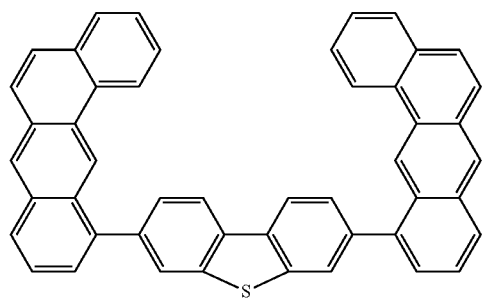
174 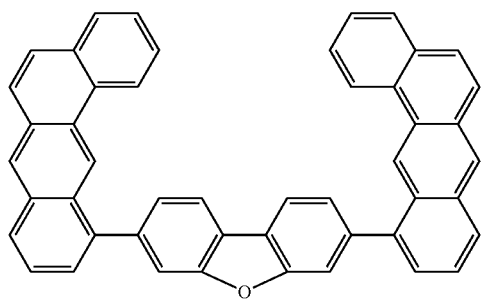 175 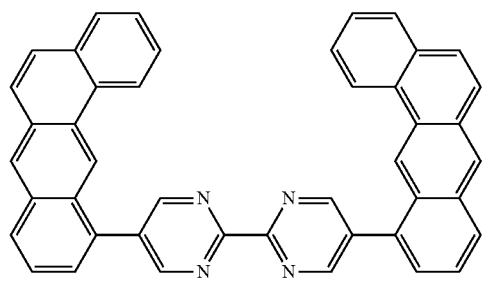
176 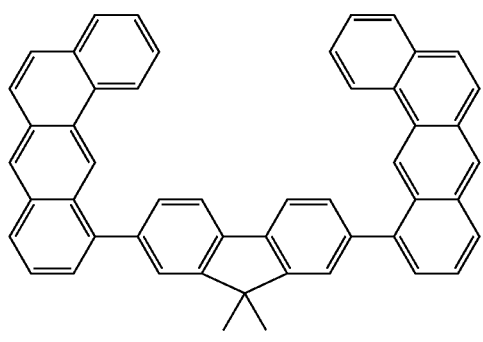 177 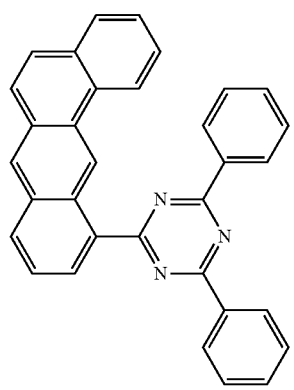

-continued
178
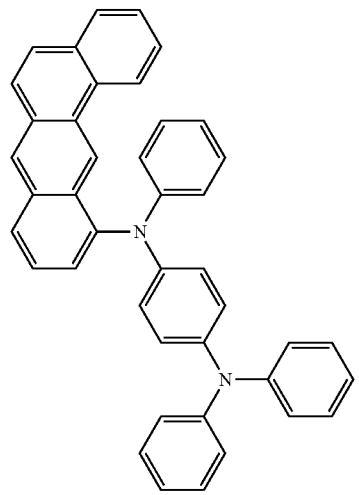
179
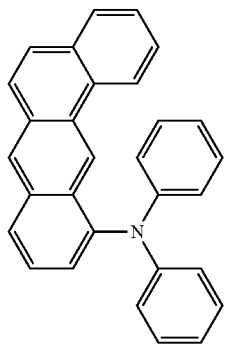
180
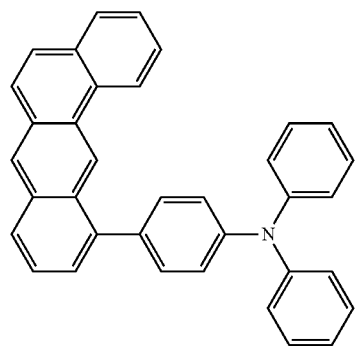
181
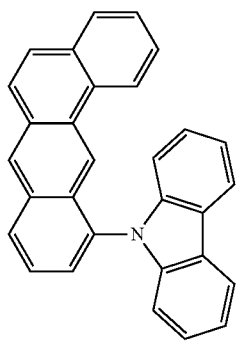
182
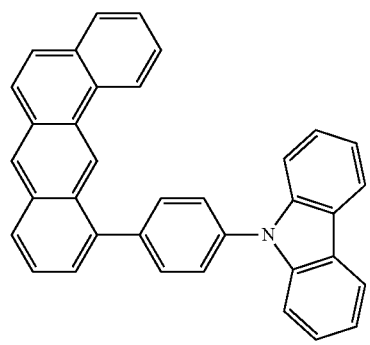
183
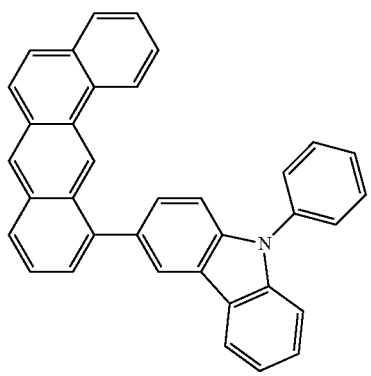
184
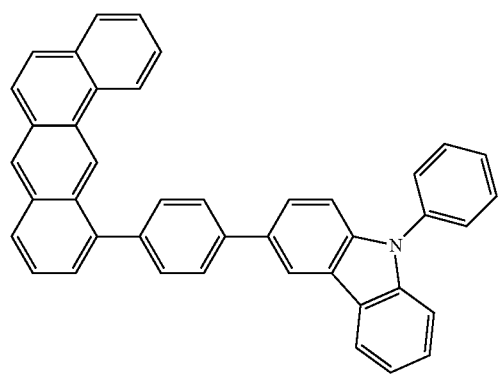
185
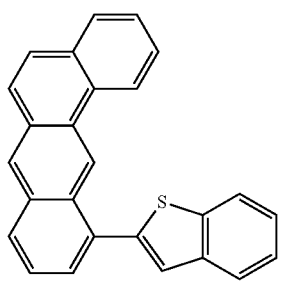

-continued
186 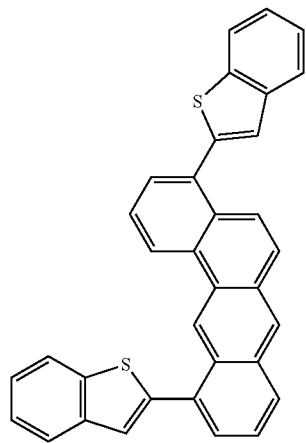
187 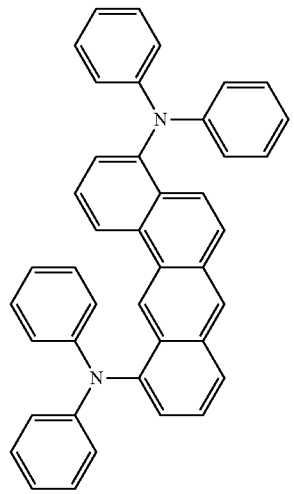
188 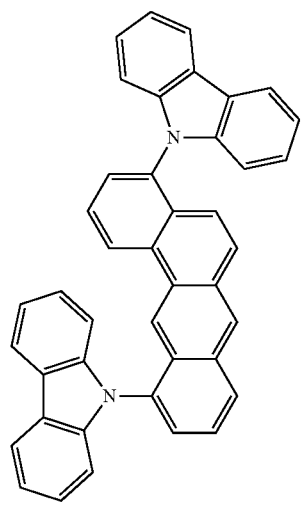
189 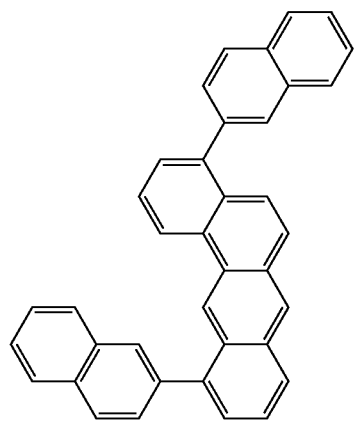
190 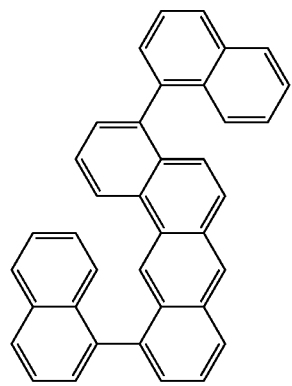
191 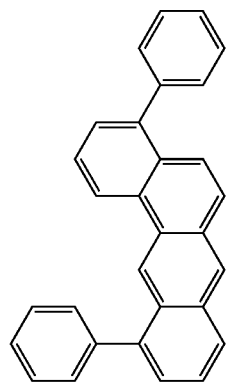

192
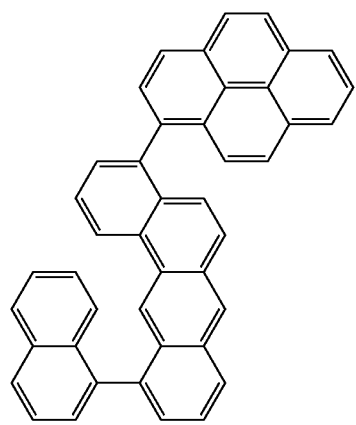
193
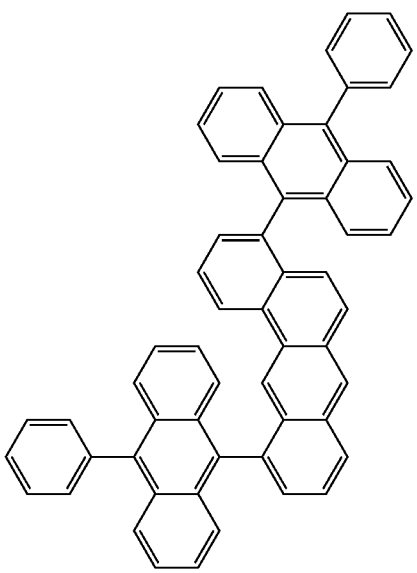
194
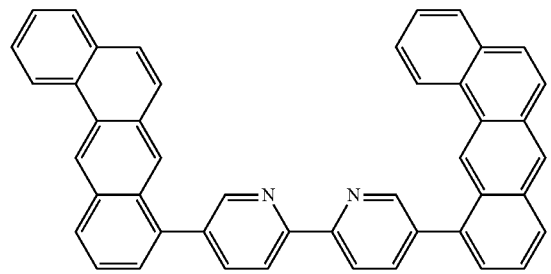
195
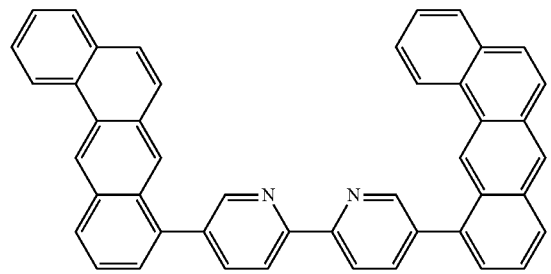
196
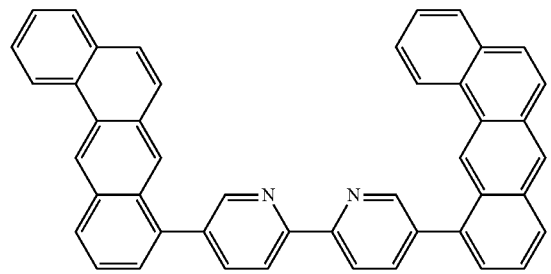
197
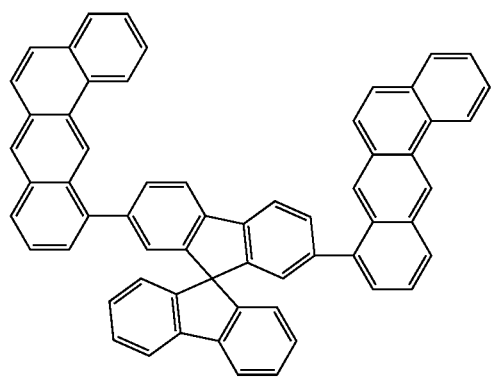
198
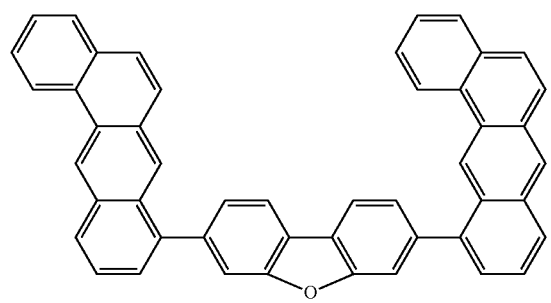
199
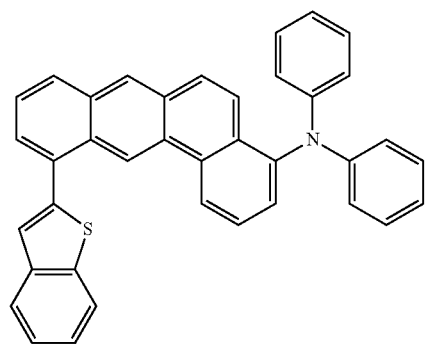

-continued
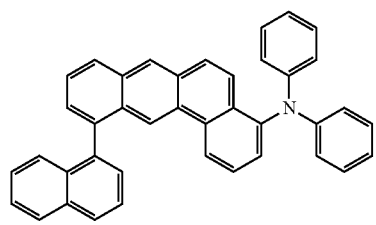
200
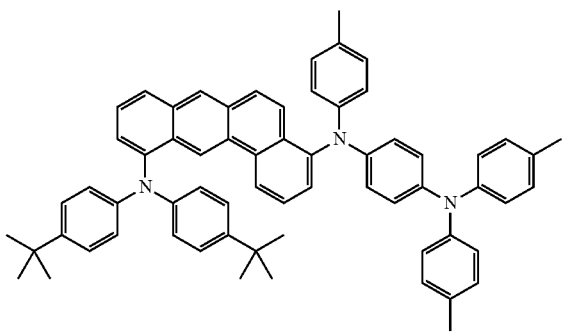
201
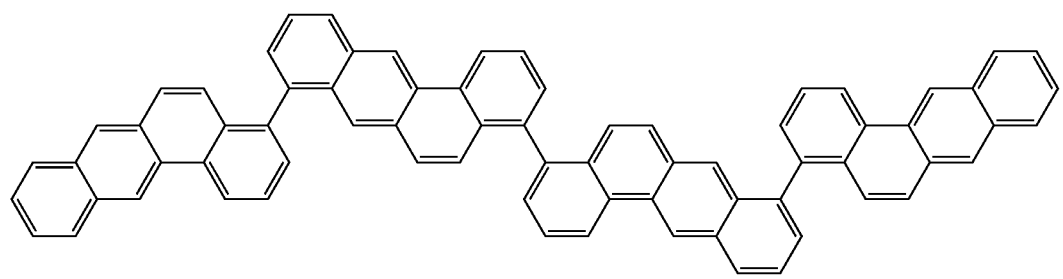
202
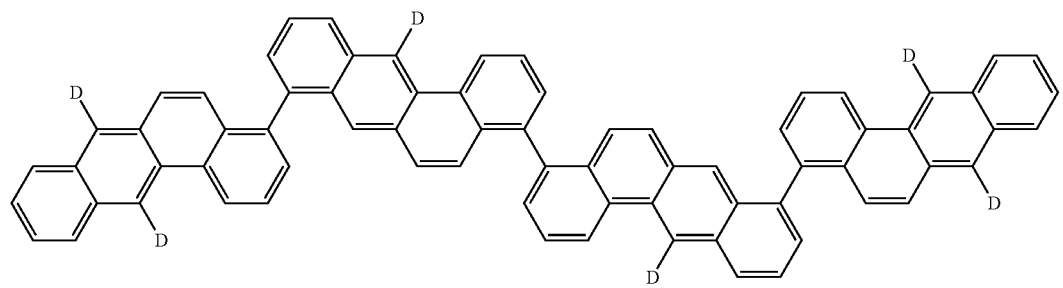
203
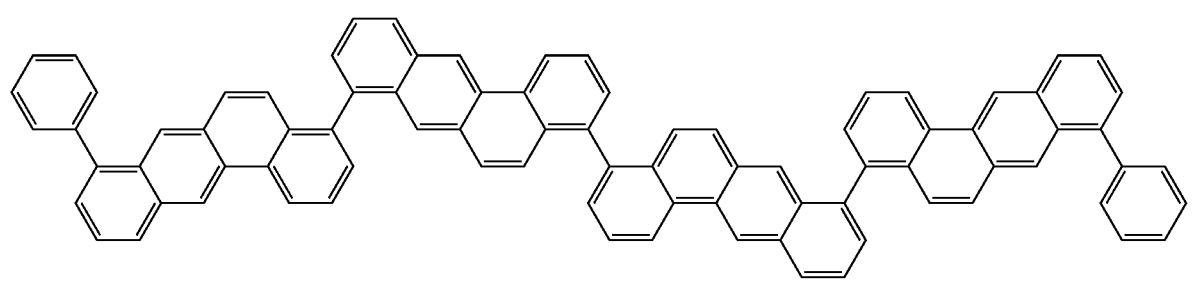
204
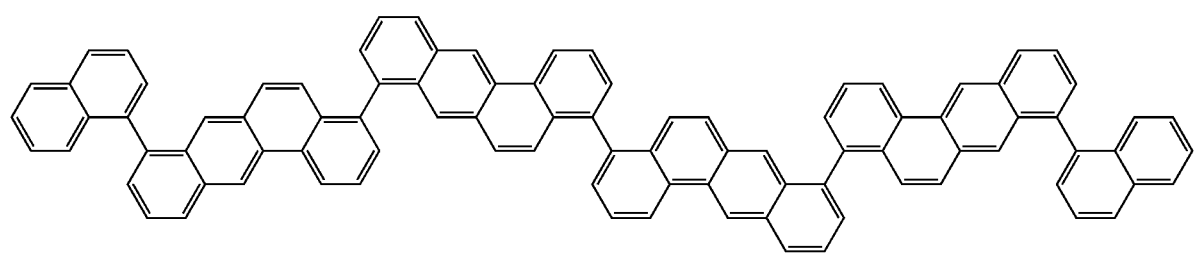
205

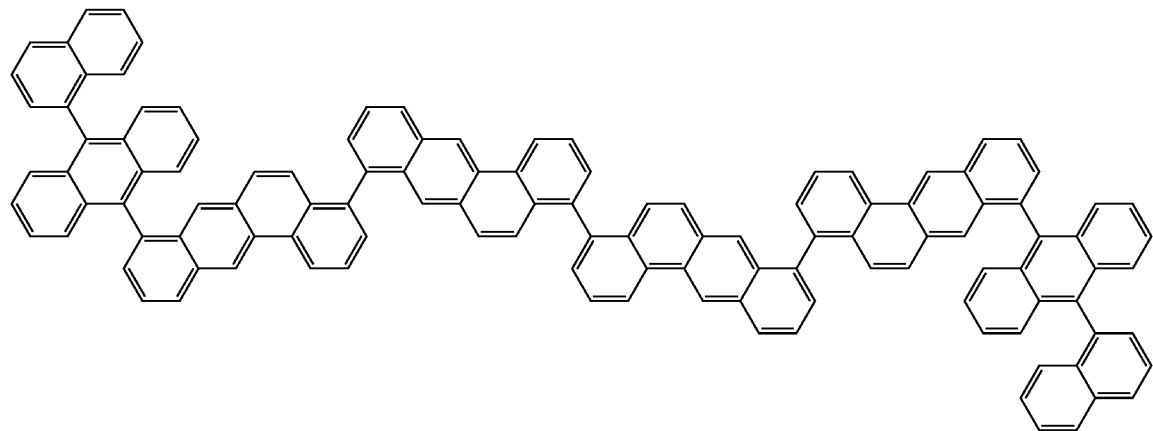
206
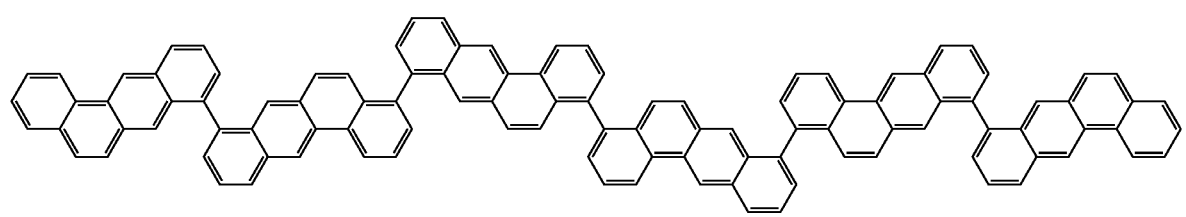
207
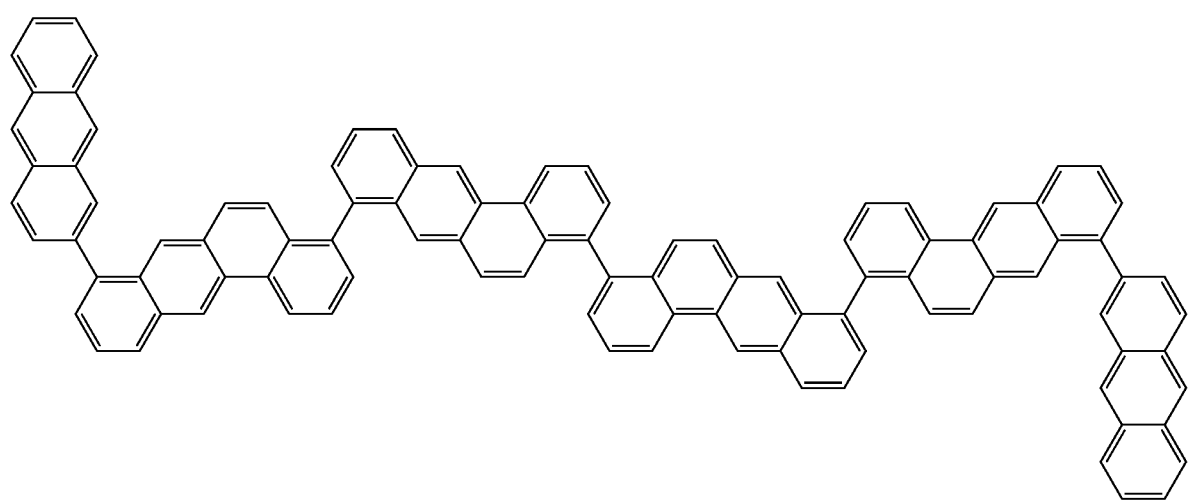
208
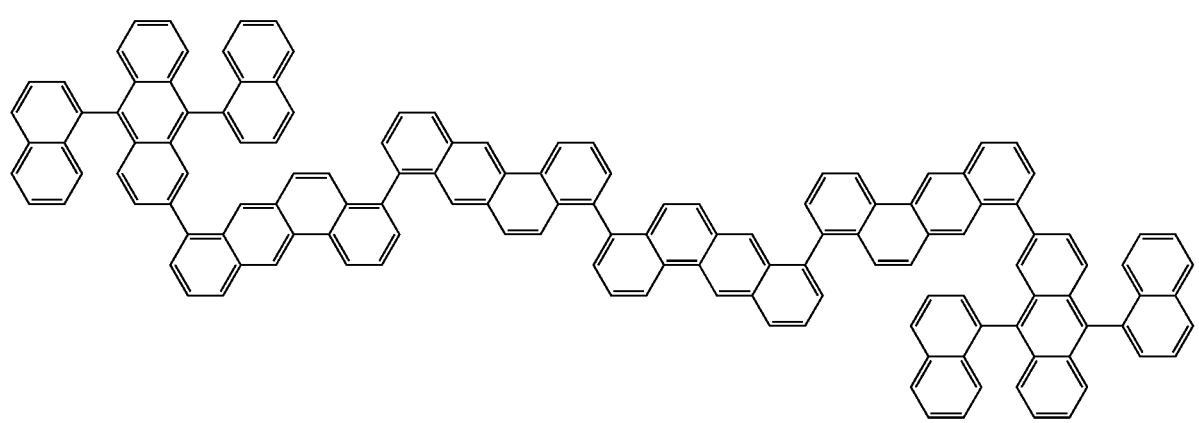
209

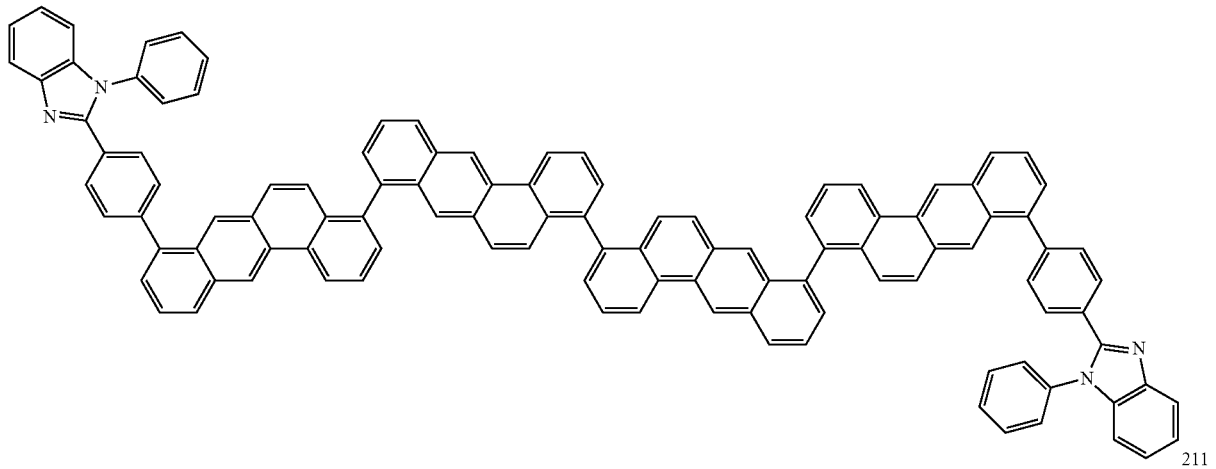
210
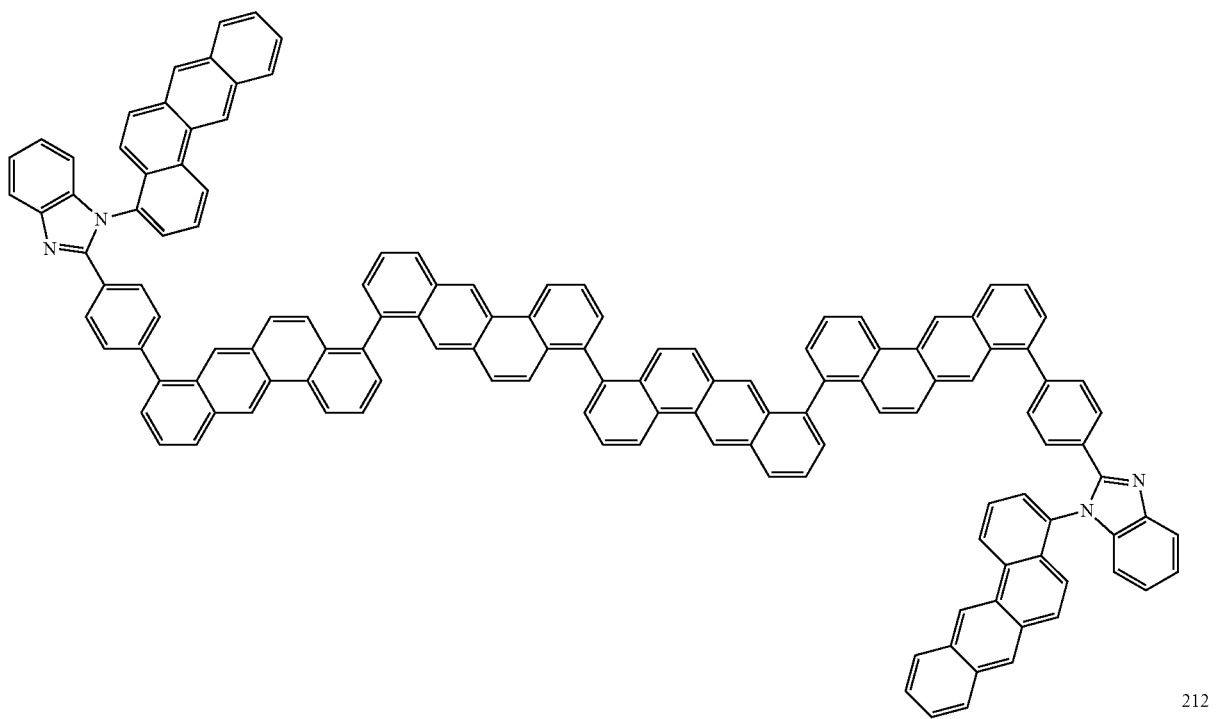
211
212
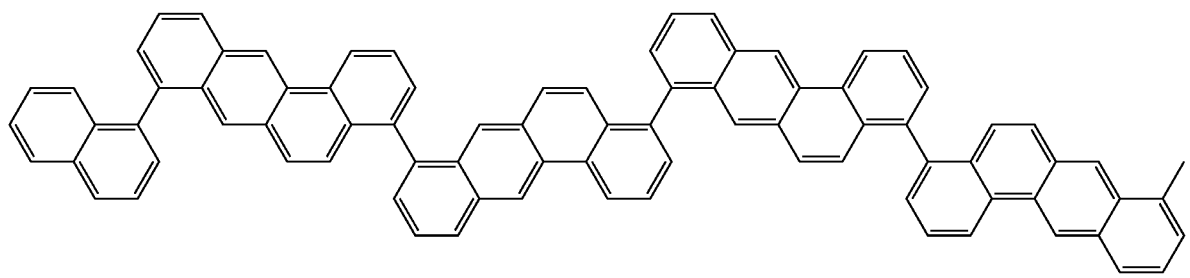
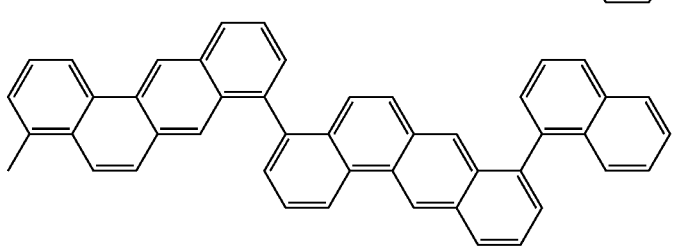

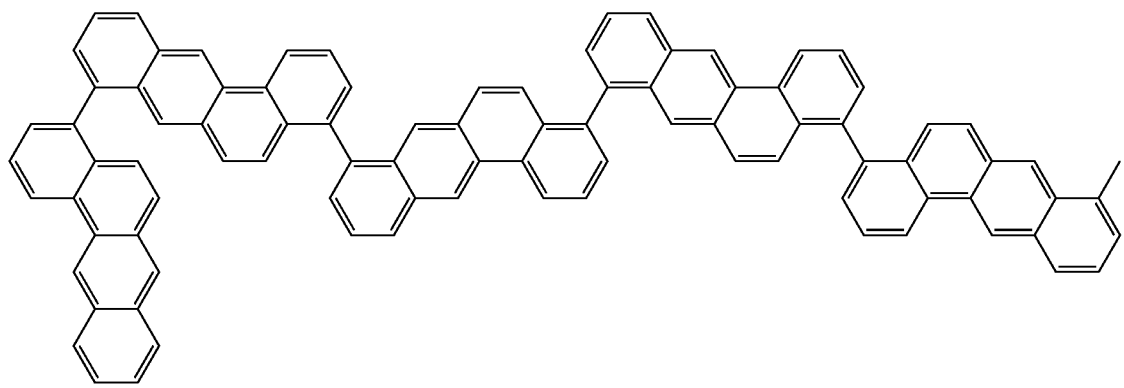
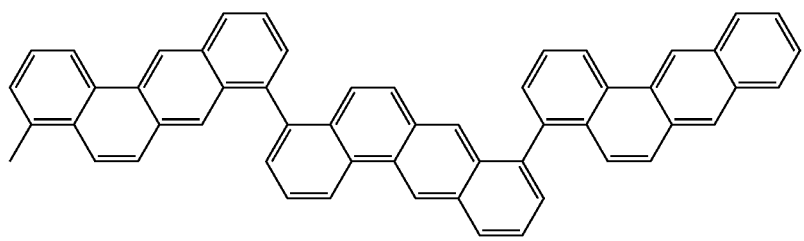
213
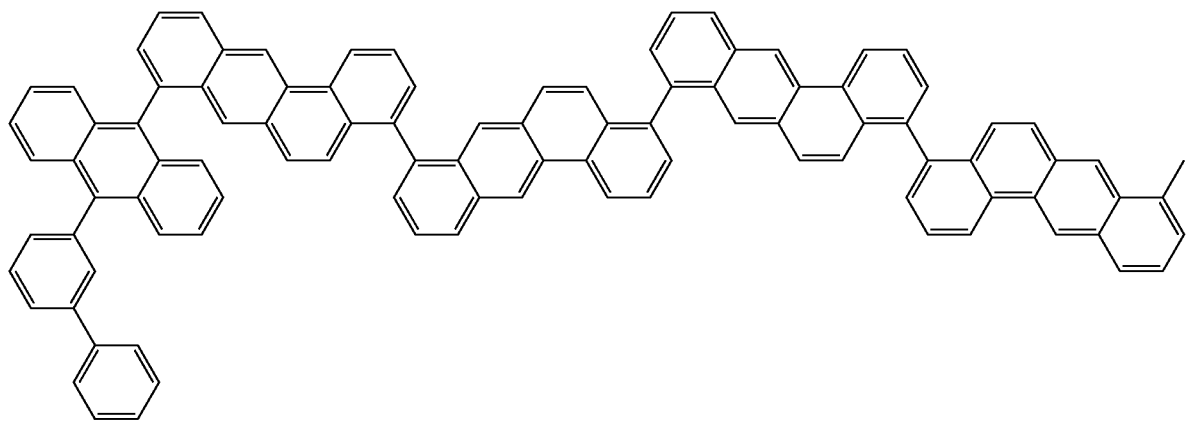
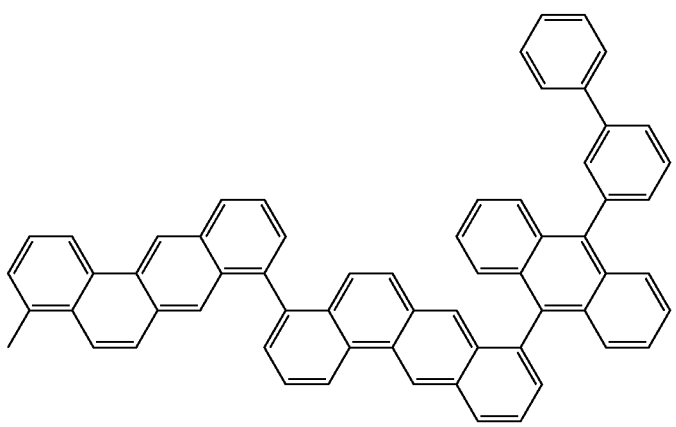
214

215
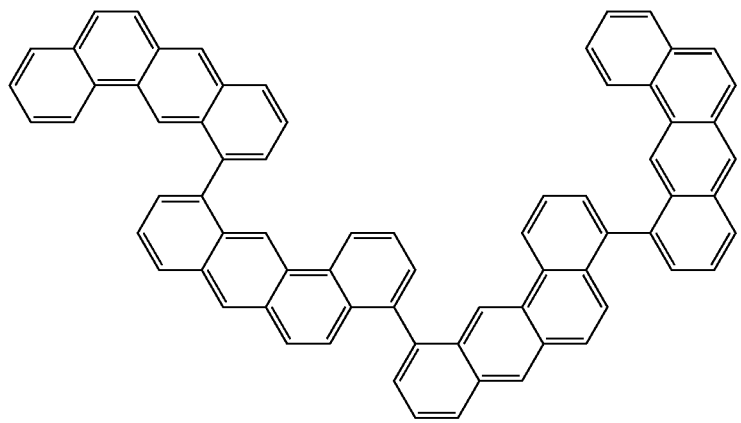
216
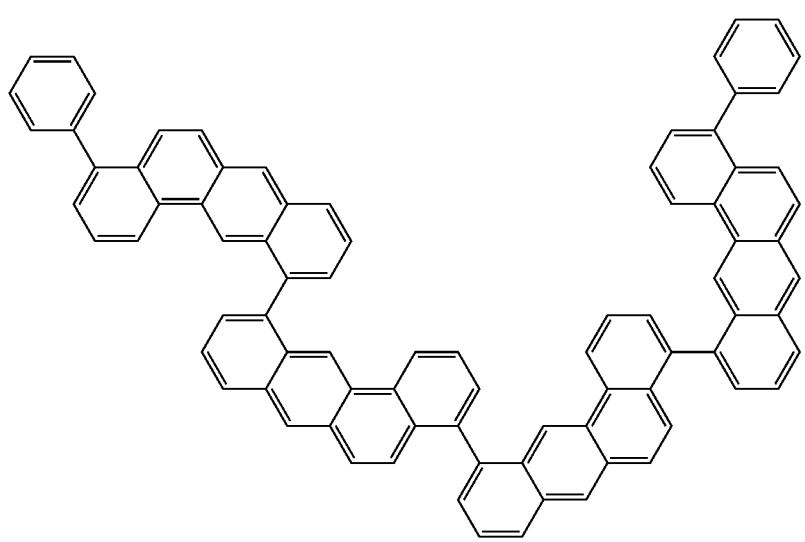
217
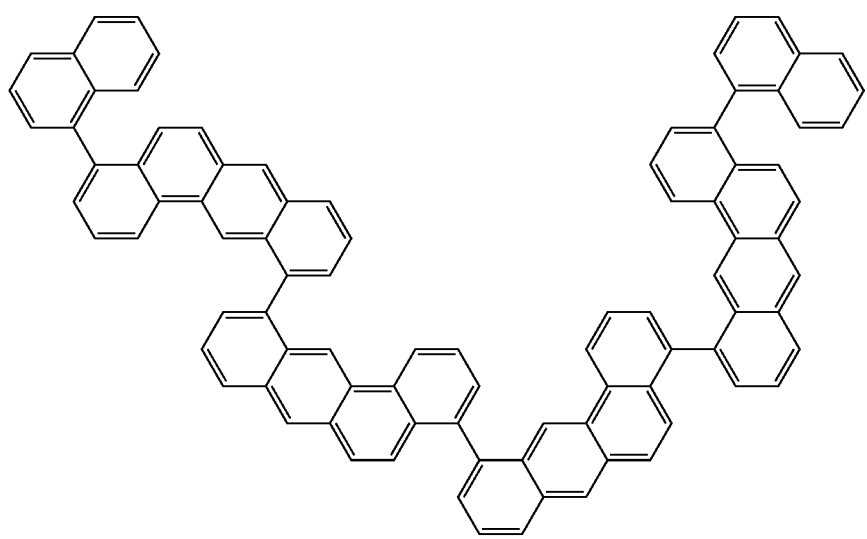

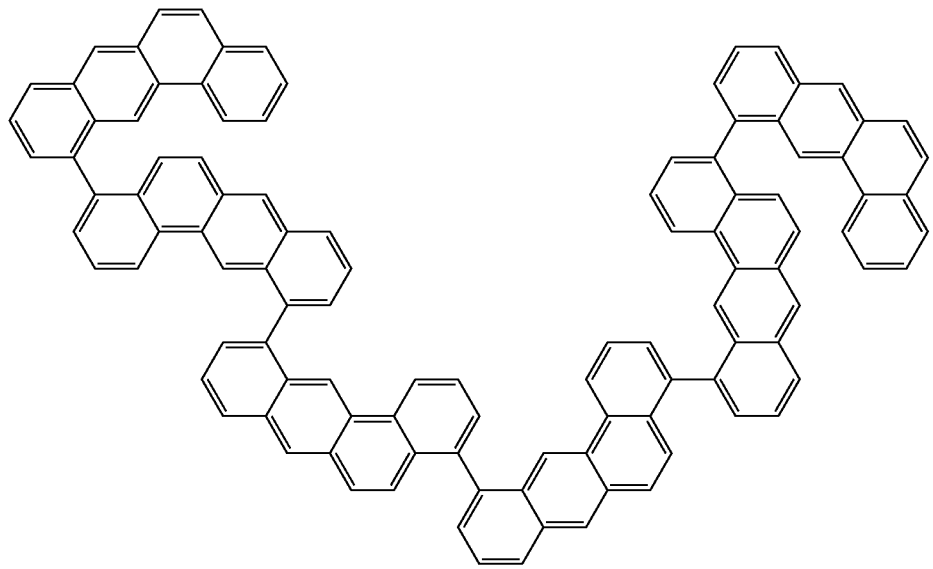

218

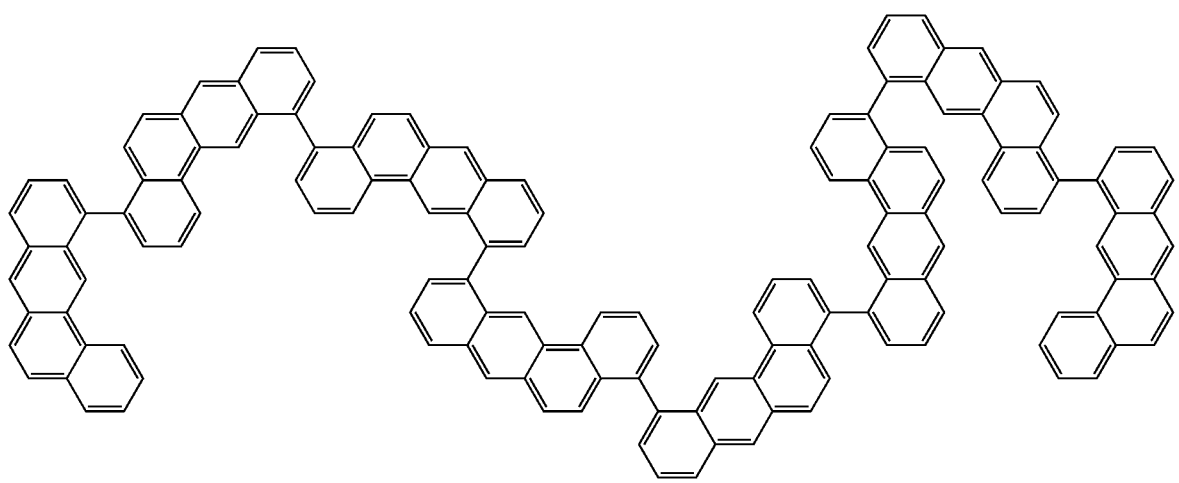

219

The compounds of the formula (1) or formula (2) according to the invention can be prepared by synthetic steps which are generally known to the person skilled in the art. The starting compounds used can be, for example, the corresponding bromobenz[a]anthraquinones, the synthesis of which is known (8-bromobenz[a]anthraquinone: J. L. Wood et al., *J. Am. Chem. Soc.* 1951, 73(9), 4494-4495, 9-bromobenz[a]anthraquinone: M. C. Kloetzel et al., *J. Org. Chem.* 1961, 26(6), 1748-1754, 8- and 11-bromobenz[a]-anthraquinone: V. Snieckus et al., *Tetrahedron Lett.* 1985, 26(9), 1145-1148). The benz[a]anthraquinones substituted by corresponding leaving groups, such as chlorine, iodine, triflate or tosylate, can likewise serve as starting compounds. The benz[a]anthraquinone derivatives can then be reduced to the corresponding benz[a]anthracenes as shown in Scheme 1 by way of example for 8-bromobenz[a]anthracene.

Scheme 1

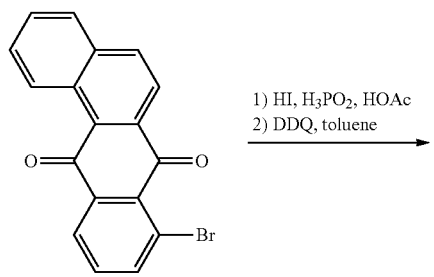

1) HI, H$_3$PO$_2$, HOAc
2) DDQ, toluene

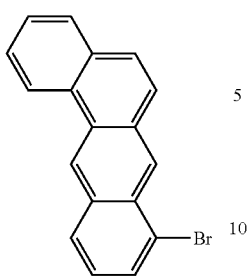

The compounds in Scheme 1 may also be substituted by one or more radicals R, where R has the same meaning as described above under formula (1) or formula (2).

Alternatively, the anthraquinone derivatives can be coupled and then reduced to the corresponding hydrocarbons, as shown in Scheme 2 by way of example for 8-bromobenz[a]anthraquinone. Instead of simple aromatisation, the corresponding 7,12-substituted benz[a]anthracene derivatives can also be synthesised here by the addition reaction of an organometallic reagent, for example an organolithium compound or a Grignard compound, followed by aromatisation.

Scheme 2

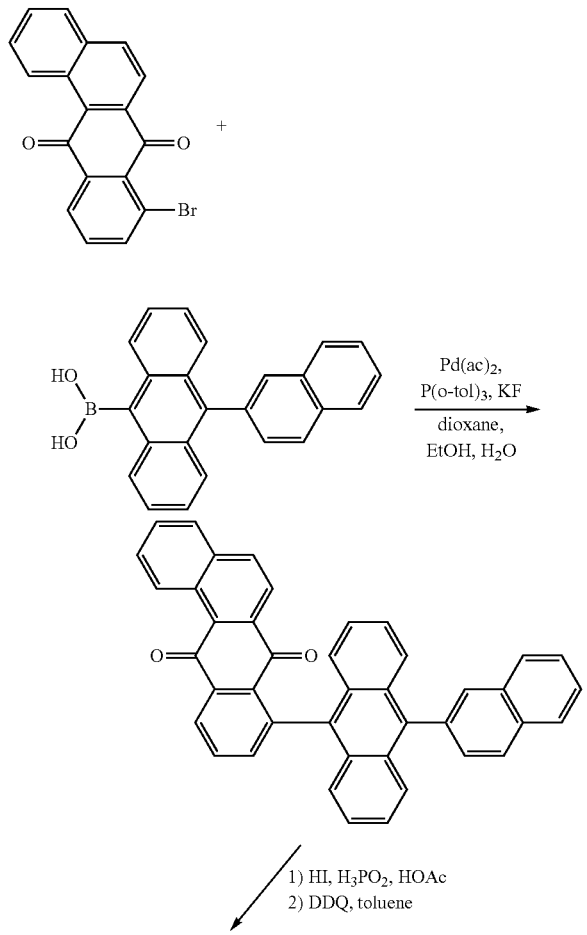

The compounds in Scheme 2 may also be substituted by one or more radicals R, where R has the same meaning as described above under formula (1) or formula (2).

The boronic acids or boronic acid derivatives derived from these compounds can be obtained by transmetallation, for example using n-butyl-lithium in THF at −78° C., followed by reaction of the lithiobenz[a]anthracene formed as an intermediate with trimethyl borate, as shown by way of example in Scheme 3 with reference to the example of 4-bromobenz[a]-anthracene, optionally followed by esterification. The lithiated compounds can furthermore be converted into ketones by reaction with electrophiles, such as benzonitrile, followed by acidic hydrolysis or into phosphine oxides using chlorodiarylphosphines followed by oxidation. Reaction of the lithiated compound with other electrophiles is also possible.

Scheme 3

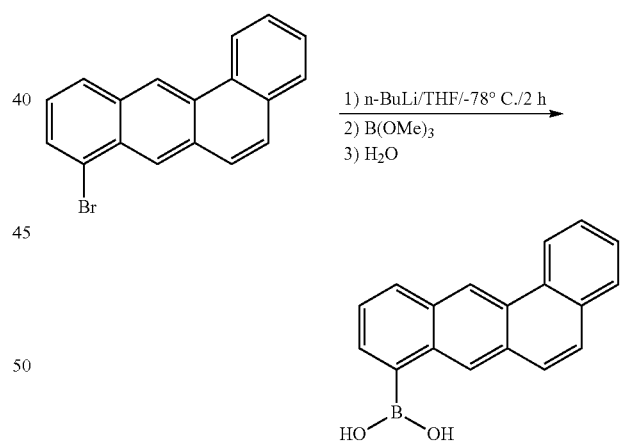

The compounds in Scheme 3 may also be substituted by one or more radicals R, where R has the same meaning as described above under formula (1) or formula (2).

The Suzuki coupling of the boronic acids or boronic acid derivatives to aryl bromides results in a large class of different aromatic and heteroaromatic compounds. This is shown by way of example in Schemes 4 a) to e), starting from benz[a]anthracene-4-boronic acid, but also applies in the same way to the other substitution patterns. Furthermore, all structures may also be substituted by one or more radicals R, where R has the same meaning as described above under formula (1) or formula (2).

Scheme 4
a)
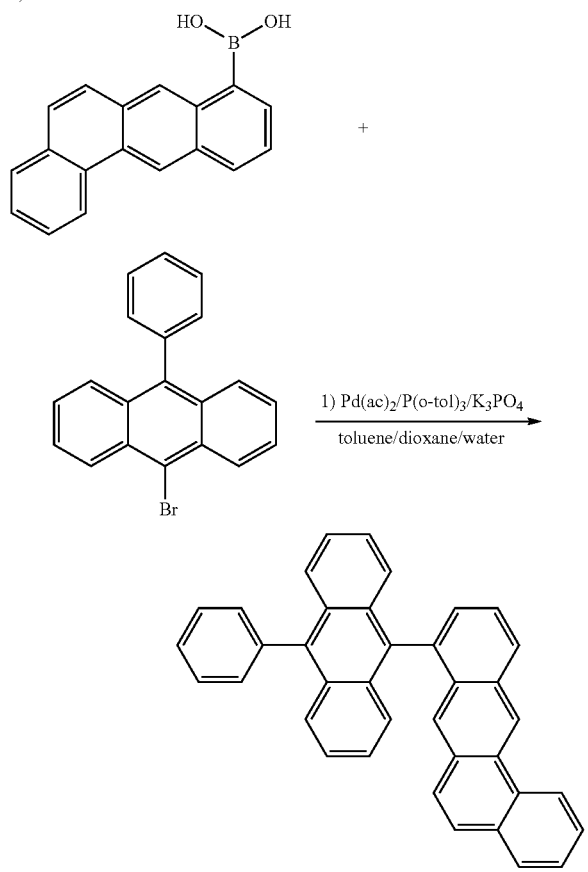
b)
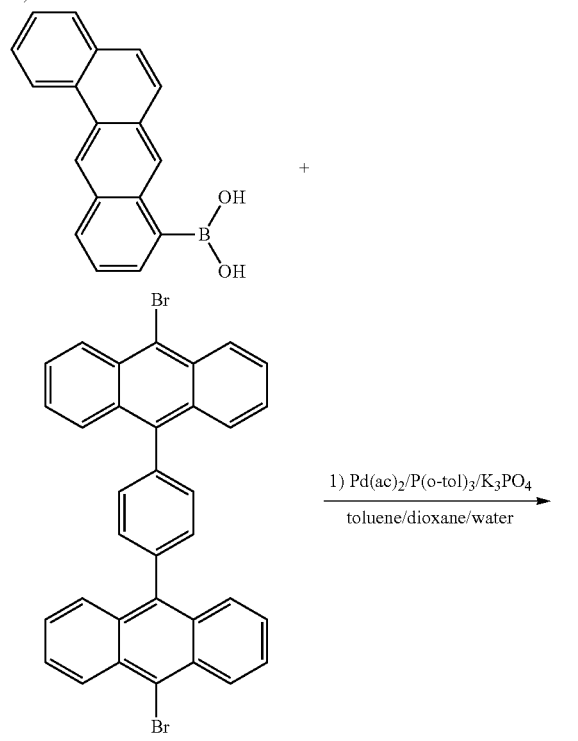
c)
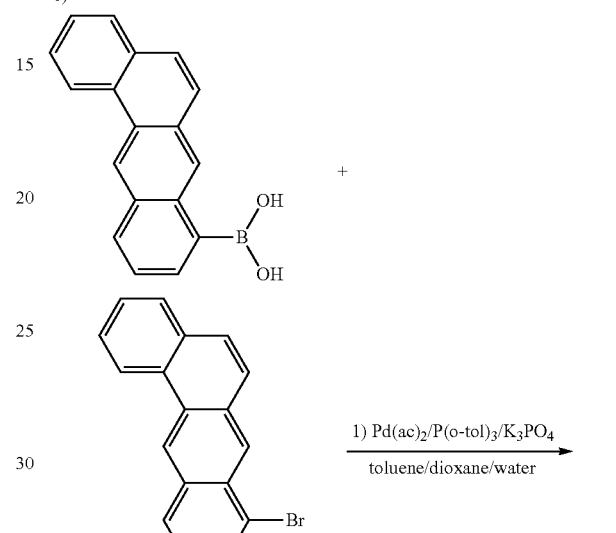
d)
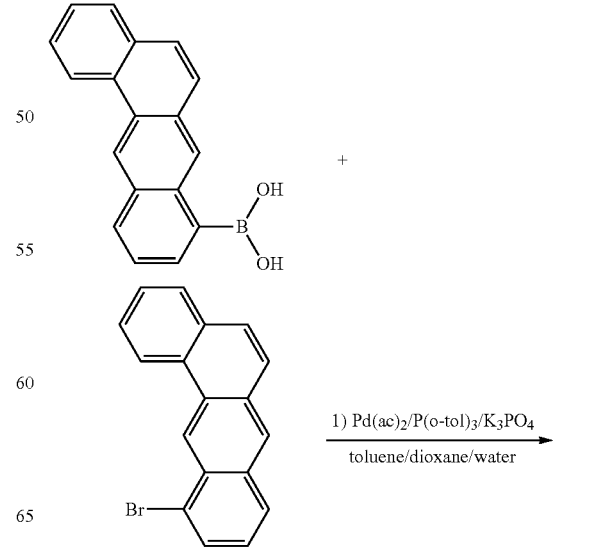
-continued
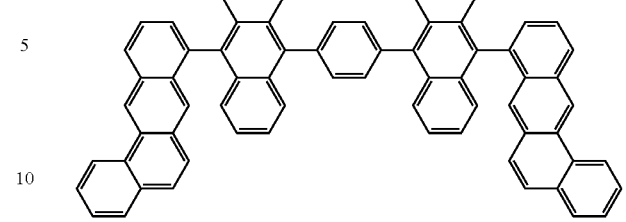

-continued

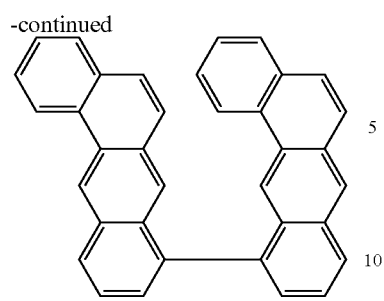

e)

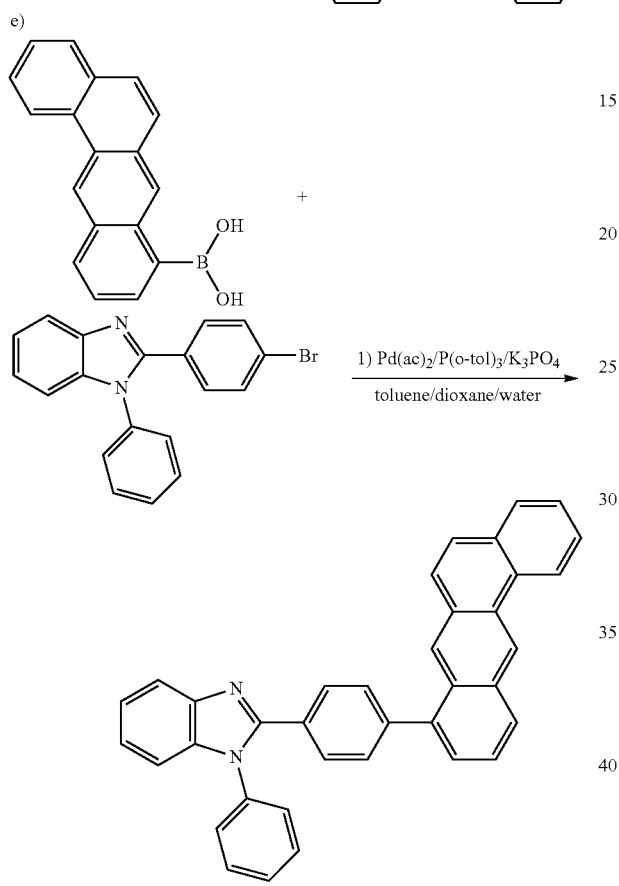

The palladium-promoted amination of the bromides by the Hartwig-Buchwald method gives the corresponding aminated benz[a]anthracenes (Scheme 6). Amination in the other positions of the benz[a]anthracene is possible correspondingly. A corresponding reaction with other leaving groups, such as chlorine, iodine, triflate, tosylate, etc., is possible.

Scheme 5

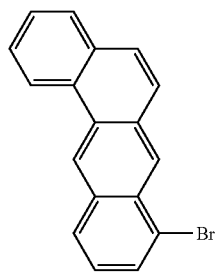

-continued

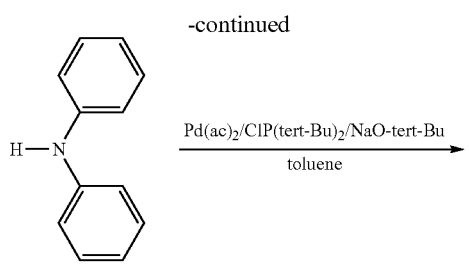

The compounds in Scheme 4 and 5 may also be substituted by one or more radicals R, where R has the same meaning as described above under formula (1) or formula (2).

Furthermore, the boronic acids can be reacted with diols, oligools and polyols to give boronic acid esters or to give anhydrides by refluxing in toluene on a water separator (Scheme 6). The reaction for positions 9 and 11 on the benz[a]anthracene proceeds correspondingly.

Scheme 6

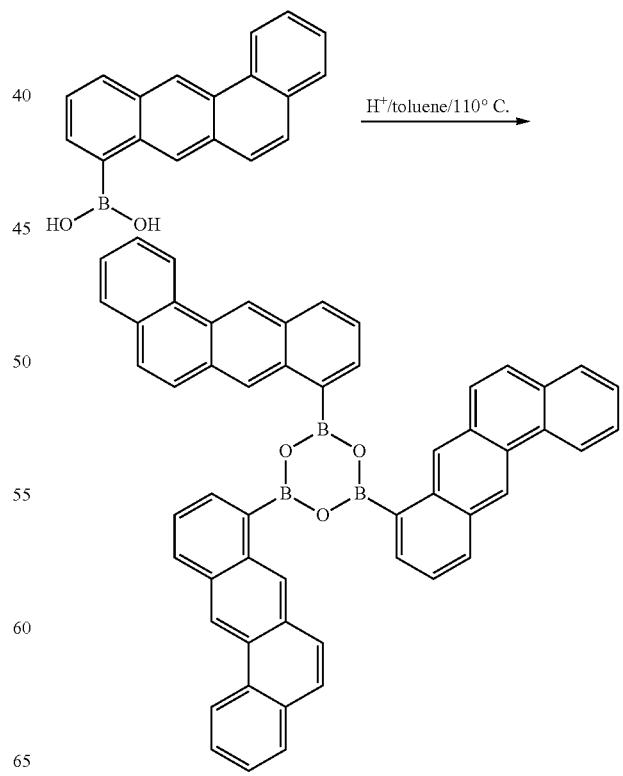

The compounds in Scheme 6 may also be substituted by one or more radicals R, where R has the same meaning as described above under formula (1) or formula (2).

The invention still furthermore relates to a process for the preparation of compounds of the formula (1) or formula (2) by coupling a benz[a]anthracene which is substituted by a reactive leaving group, in particular chlorine, bromine, iodine, triflate, tosylate, boronic acid or boronic acid ester, to a functionalised aromatic compound or to a mono- or disubstituted amine. The reactive leaving group is preferably bromine. Suitable coupling reactions between the skeleton of the formula (1) or formula (2) and the aryl substituent are, in particular, transition-metal-catalysed coupling reactions, in particular Suzuki coupling with palladium catalysis, so that coupling of a boronic acid derivative to a halogen derivative is particularly suitable here. A suitable coupling reaction to a mono- or disubstituted amine is, in particular, palladium-catalysed coupling by the Hartwig-Buchwald method. The Ullmann coupling is furthermore suitable for this purpose. The reaction conditions for such reactions are known in general terms to the person skilled in the art of organic synthesis.

The benz[a]anthraquinone derivatives described above may additionally be brominated, giving difunctionalised benz[a]anthraquinones. This is shown in Scheme 7 by way of example for the bromination of 8-bromobenz[a]-anthraquinone. The benz[a]anthraquinones substituted by corresponding leaving groups, such as chlorine, iodine, triflate or tosylate, can likewise serve as starting compounds, giving benz[a]anthraquinone derivatives having two different leaving groups.

Scheme 7

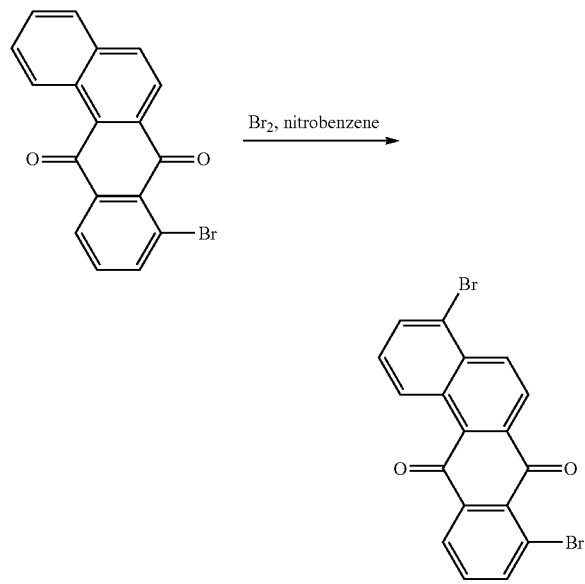

The compounds in Scheme 7 may also be substituted by one or more radicals R, where R has the same meaning as described above under formula (1) or formula (2).

The difunctionalised benz[a]anthraquinone derivatives can then be reduced to the corresponding benz[a]anthracenes, as shown in Scheme 8 by way of example for 4,8-dibromobenz[a]anthracene.

Scheme 8

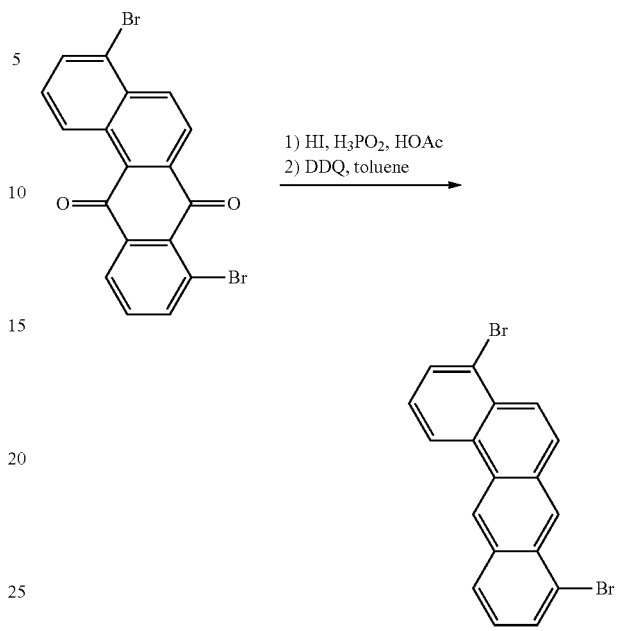

The compounds in Scheme 8 may also be substituted by one or more radicals R, where R has the same meaning as described above under formula (1) or formula (2).

Alternatively, the anthraquinone derivatives can be coupled analogously to Scheme 2 and then reduced to the corresponding hydrocarbons, giving disubstituted benz[a]anthracenes. Instead of simple aromatisation, the corresponding 7,12-substituted benz[a]anthracene derivatives can also be synthesised here by the addition reaction of an organometallic reagent, for example an organolithium compound or a Grignard compound, followed by aromatisation.

The boronic acids or boronic acid derivatives derived from these compounds can be obtained by transmetallation, for example using n-butyl-lithium in THF at −78° C., and subsequent reaction of the lithiobenz[a]-anthracene formed as intermediate with trimethyl borate, as shown in Scheme 9 by way of example for 4,8-dibromobenz[a]anthracene, optionally followed by esterification. Furthermore, the lithiated compounds can be converted into ketones by reaction with electrophiles, such as benzonitrile, and subsequent acidic hydrolysis or into phosphine oxides by reaction with diarylphosphine chlorides and subsequent oxidation. The reaction of the lithiated compound with other electrophiles is also possible. Depending on the reaction conditions, monolithiation or dilithiation is possible here.

Scheme 9

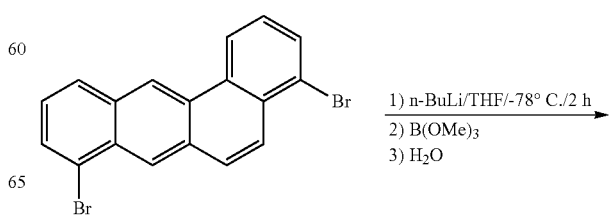

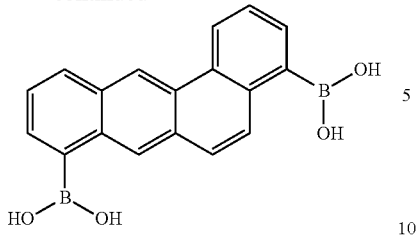 5

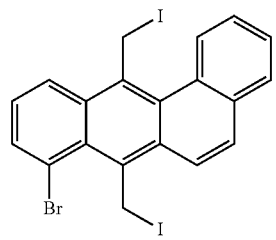

The compounds in Scheme 9 may also be substituted by one or more radicals R, where R has the same meaning as described above under formula (1) or formula (2).

A multiplicity of different aromatic and heteroaromatic compounds can also be obtained from the difunctionalised benz[a]anthracenes analogously to the syntheses described in Scheme 4 and 5 for monofunctionalised benz[a]anthracenes. The invention therefore furthermore relates to a process for the preparation of compounds of the formula (1) or formula (2) by coupling a difunctionalised benz[a]anthracene which is substituted by two reactive leaving groups, in particular chlorine, bromine, iodine, triflate, tosylate, boronic acid or boronic acid ester, to a functionalised aromatic compound or to a mono- or disubstituted amine. The reactive leaving group is preferably bromine. Suitable coupling reactions between the skeleton of the formula (1) or formula (2) and the aryl substituent or the amine are the reaction types already mentioned above.

The invention therefore furthermore relates to compounds of the following formula (37) or (37a), which represent an important intermediate in the synthesis of compounds of the formula (1) or formula (2)

formula (37)

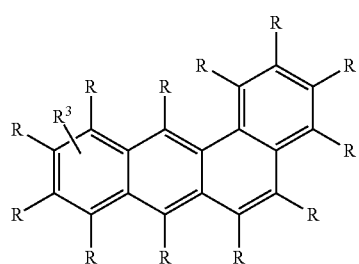

formula (37a)

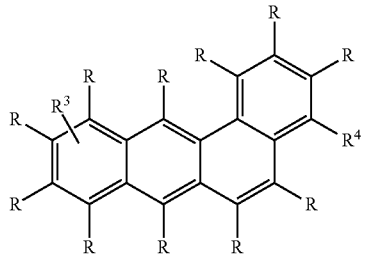

where R, $R^1$ and $Ar^1$ have the same meaning as described above for compounds of the formula (1) or formula (2), and $R^3$ is bonded in position 8, 9 or 11 of the benz[a]anthracene and correspondingly no group R is bonded at this position, and furthermore:

$R^3$, $R^4$ stand for Cl, Br, I, $B(OR^1)_2$ or $B(OAr^1)_2$;

The following compounds are excluded from the invention:

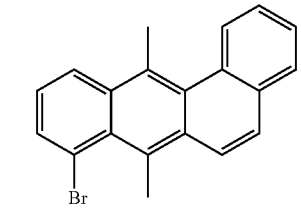

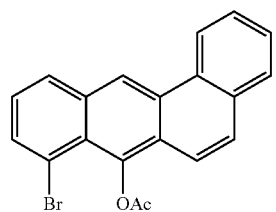

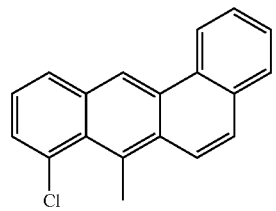

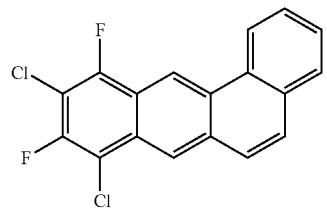

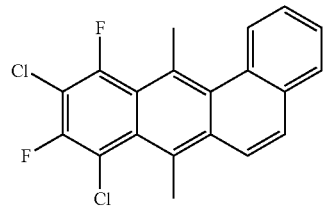

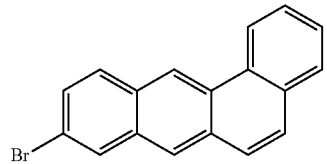

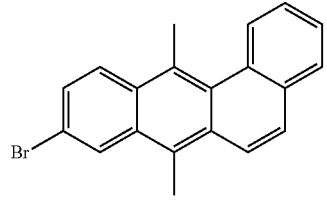

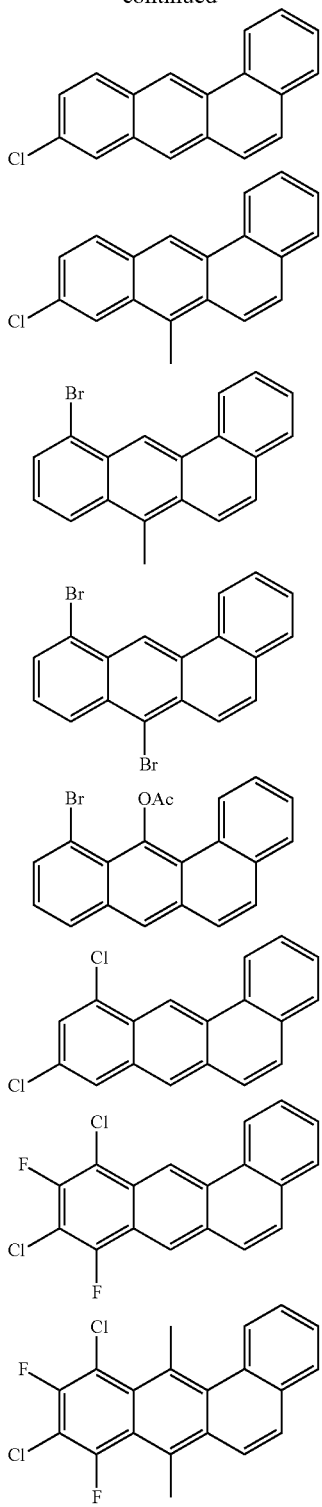

The present invention furthermore relates to the use of a compound of the formula (37) or (37a) for the preparation of a compound of the formula (1) or formula (2).

It is furthermore also possible to employ the boronic acid derivatives of the formula (37) or (37a) directly as active compound in electronic devices, as described in general terms in WO 06/117052.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here preferably takes place via the halogen functionality or the boronic acid functionality.

The invention therefore furthermore relates to oligomers, polymers or dendrimers containing one or more compounds of the formula (1) or formula (2), where one or more radicals R or $R^2$ or Ar or X or Y represent bonds from the compound of the formula (1) or formula (2) to the polymer, oligomer or dendrimer. Depending on the linking of the compound of the formula (1) or formula (2), the benz[a]anthracene unit therefore forms a side chain of the oligomer or polymer or is linked in the main chain. For the purposes of this invention, an oligomer is taken to mean a compound which contains at least three benz[a]anthracene units. The polymers, oligomers or dendrimers may be conjugated, partially conjugated or non-conjugated. The oligomers or polymers may be linear, branched or dendritic. In the structures linked in a linear manner, the units of the formula (1) or formula (2) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) or formula (2) may, for example, be linked via a trivalent or polyvalent group, for example via a trivalent or polyvalent aromatic or heteroaromatic group, to give a branched or dendritic oligomer or polymer. The units of the formula (1) or formula (2) are preferably linked into the oligomer, dendrimer or polymer via positions 4 and 8, 4 and 9 or 4 and 11 of the benz[a]-anthracene. Linking via two positions to the group R or to the group X or to the group Y is furthermore preferred.

For the recurring units of the formula (1) or formula (2) in oligomers, dendrimers and polymers, the same preferences apply as described above.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units, in particular those based on triarylamines.

A further embodiment of the present invention is the use of a compound of the following formula (38) or formula (39) or a compound of the formula (37) or an oligomer, dendrimer or polymer comprising one or more compounds of the formula (1) or formula (2), where one or more radicals R or $R^2$ or Ar or X or Y represent bonds from the compound of the formula (1) or formula (2) to the polymer, oligomer or dendrimer, in electronic devices, in particular in organic electroluminescent devices:

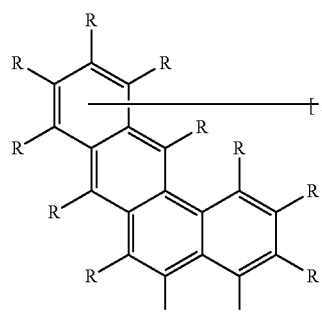
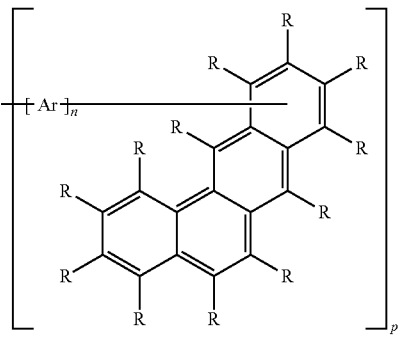

formula (38)

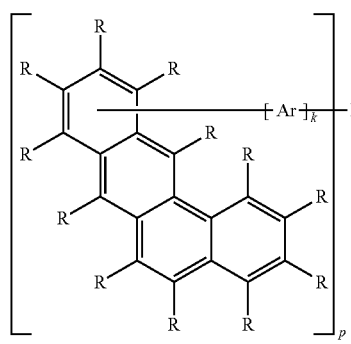
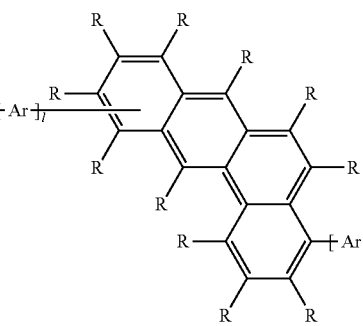

formula (39)

where the symbols and indices used are intended to have the same meanings as in the above embodiments.

The compounds of the formula (1) or formula (2) and corresponding oligomers, dendrimers and polymers are suitable for use in electronic devices, in particular in organic electroluminescent devices (OLEDs, PLEDs). Depending on the substitution, the compounds are employed in different functions and layers.

The invention therefore furthermore relates to the use of compounds of the formula (1) or formula (2) and corresponding oligomers, dendrimers or polymers in electronic devices, in particular in organic electroluminescent devices. The preferred compounds of the formulae (3) to (21) mentioned above are particularly suitable for this purpose.

The invention furthermore relates to electronic devices comprising at least one compound of the formula (1) or formula (2) or at least one corresponding oligomer, dendrimer or polymer, in particular organic electroluminescent devices comprising anode, cathode and at least one emitting layer, characterised in that at least one organic layer, which may be an emitting layer or another layer, comprises at least one compound of the formula (1) or formula (2) or at least one corresponding oligomer, dendrimer or polymer. The preferred compounds of the formulae (3) to (21) mentioned above are particularly suitable for this purpose.

Apart from the cathode, anode and the emitting layer, the organic electroluminescent device may also contain further layers. These are selected, for example, from in each case one or more hole-injection layers, hole-transport layers, electron-transport layers, electron-injection layers, organic or inorganic p/n junctions and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

The person skilled in the art of organic electroluminescence knows which materials he can employ for these further layers. In general, all materials as used in accordance with the prior art are suitable for the further layers, and the person skilled in the art will be able to combine these materials with the materials according to the invention in an organic electroluminescent device without carrying out an inventive step. Examples of preferred hole-transport materials which can be used in a hole-transport or hole-injection layer in the electroluminescent device according to the invention are indenofluorenamines and related derivatives (for example in accordance with WO 06/122630 or WO 06/100896), the amine derivatives disclosed in EP 1661888, hexaazatriphenylene derivatives (for example in accordance with WO 01/049806), amine derivatives with condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847).

In a further preferred embodiment of the invention, the organic electroluminescent device comprises two or more emitting layers, where at least one organic layer comprises at least one compound of the formula (1) or formula (2). These emission layers particularly preferably have in total a plurality of emission maxima between 380 nm and 750 nm, resulting overall in white emission, i.e. various emitting compounds which are able to fluoresce or phosphoresce and emit blue and yellow and orange or red light are used in the emitting layers. The compound of the formula (1) or formula (2) is preferably used here in a blue-emitting layer. Particular preference is given to three-layer systems, i.e. systems having three emitting layers, where at least one of these layers comprises at least one compound of the formula (1) or formula (2) and where the three layers exhibit blue, green and orange or red emission (for the basic structure see, for example, WO 05/011013). The green and orange or red emitters employed here are preferably phosphorescent compounds. Emitters which have broad-band emission and thus exhibit white emission are likewise suitable for white emission.

In an embodiment of the invention, the compounds of the formulae (1) to (21) are employed as matrix material for fluorescent dopants, in particular for blue-fluorescent dopants. In this case, one or more groups Ar and/or X and/or Y in formulae (1) to (10) and (14) to (17) are preferably selected from simple or condensed aryl or heteroaryl groups, in particular phenylanthryl or 1- or 2-naphthylanthryl. One or more groups Ar and/or X and/or Y in formulae (1) to (8) and (11) to (21) are furthermore preferably selected from condensed arylene groups, in particular 9,10-anthracene.

A matrix material in a system comprising matrix and dopant is taken to mean the component which is present in the higher proportion in the system. In a system comprising one matrix and a plurality of dopants, the matrix is taken to mean the component which has the highest proportion in the mixture. It is furthermore also possible to use a mixture of a plurality of matrix materials.

The proportion of the matrix material of the formula (1) or formula (2) in the emitting layer is between 50.0 and 99.9% by weight, preferably between 80.0 and 99.5% by weight and particularly preferably between 90.0 and 99.0% by weight. Correspondingly, the proportion of the dopant is between 0.01 and 50.0% by weight, preferably between 0.5 and 20.0% by weight and particularly preferably between 1 and 10% by weight, in each case based on 100% of the entire emitting layer.

It is furthermore also possible to use a mixture of a plurality of matrix materials, where one matrix material is a compound of the formula (1) or (2). Suitable further matrix materials with which the compounds according to the invention can be combined are selected from arylamines, anthracene derivatives, in particular anthracene derivatives substituted by at least one condensed aryl group, aromatic hydrocarbons or electron-conducting compounds, in particular compounds which contain at least one electron-deficient heteroaromatic ring system.

Preferred dopants, which can be employed in combination with the above-mentioned matrix material, are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic amine. A distyryl-amine is taken to mean a compound which contains two substituted or unsubstituted styryl groups and at least one, preferably aromatic amine. A tristyrylamine is taken to mean a compound which contains three substituted or unsubstituted styryl groups and at least one, preferably aromatic amine. A tetrastyrylamine is taken to mean a compound which contains four substituted or unsubstituted styryl groups and at least one, preferably aromatic amine. The styryl groups are particularly preferably stilbenes, which may also be further substituted. Cor-responding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoeindenofluorenamines or benzoeindenofluorenediamines, for example in accordance with WO 08/006449, and dibenzoindenofluorenamines or dibenzoindenofluorenediamines, for example in accordance with WO 07/140847. Examples of dopants from the class of the styrylamines are substituted or unsubstituted tristilbenamines or the dopants described in WO 06/000388, WO 06/058737, WO 06/000389, WO 07/065549 and WO 07/115610. Preference is again furthermore given to the dopants according to the invention described below. Preferred fluorescent dopants are furthermore condensed aromatic hydrocarbons, such as, for example, the compounds disclosed in DE 102008035413.

In a further embodiment of the invention, the compounds of the formula (1) or formula (2) are employed as emitting materials. The compounds are particularly suitable as emitting compounds If at least one Ar and/or X and/or Y group in compounds of the formulae (1) to (21) contains at least one arylamino unit. Preferred arylamino units are the groups of the formulae (31) and (32) depicted above. The compounds are furthermore suitable as emitting compounds If the group X or the group Y in compounds of the formulae (1) to (21) stands for N or NAr$^1$. However, compounds which do not contain an amino group can also be employed as emitting compounds.

The proportion of the compound of the formula (1) or formula (2) in the mixture of the emitting layer is between 0.1 and 50.0% by weight, preferably between 0.5 and 20.0% by weight, particularly preferably between 1.0 and 10.0% by weight. Correspondingly, the proportion of the matrix material is between 50.0 and 99.9% by weight, preferably between 80.0 and 99.5% by weight, particularly preferably between 90.0 and 99.0% by weight, in each case base on 100% of the mixture as a whole.

Suitable matrix materials in this case are materials from various classes of substance. Preferred matrix materials are selected from the classes of the oligoarylenes (for example 2,2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi in accordance with EP 676461), the benzanthracene derivatives (for example in accordance with WO 08/145239), the benzophenanthrene derivatives (for example in accordance with WO 09/069566 or the unpublished application DE 102009005746.3), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268) or the boronic acid derivatives (for example in accordance with WO 06/117052). Suitable matrix materials are furthermore also the benz[a]anthracene compounds according to the invention described above. Apart from the compounds according to the invention, particularly preferred matrix materials are selected from the classes of the oligoarylenes containing naphthalene, anthracene and/or pyrene, or atropisomers of these compounds, the oligoarylenevinylenes, the ketones, the phosphine oxides and the sulfoxides. Apart from the benz[a]anthracene compounds according to the invention, very particularly preferred matrix materials are selected from the classes of the oligoarylenes containing anthracene and/or pyrene, or atropisomers of these compounds, the phosphine oxides and the sulfoxides. For the purposes of this invention, an oligoarylene is intended to be taken to mean a compound in which at least three aryl or arylene groups are bonded to one another.

In still a further embodiment of the invention, the compounds of the formula (1) or formula (2) are employed as hole-transport material or hole-injection material. The compounds are then preferably substituted by at least one $N(Ar^1)_2$ group; at least one radical R particularly preferably represents an $N(Ar^1)_2$ group. The $N(Ar^1)_2$ groups are preferably selected from the formulae (31) and (32) described above. The compounds are furthermore preferred if the group X or the group Y in compounds of the formulae (1) to (21) stands for N or $NAr^1$. The compound is preferably employed in a hole-transport or hole-injection layer. For the purposes of this invention, a hole-injection layer is a layer which is directly adjacent to the anode. For the purposes of this invention, a hole-transport layer is a layer which is located between a hole-injection layer and an emission layer or an electron-blocking layer. If the compounds of the formula (1) or formula (2) are used as hole-transport material or hole-injection material, it may be preferred for them to be doped with electron-acceptor compounds, for example with $F_4$-TCNQ or with compounds as described in EP 1476881 or EP 1596445.

In still a further embodiment of the invention, the compounds of the formula (1) or formula (2) are employed as electron-transport material. It is preferred here for one or more substituents R and/or $R^1$ to contain at least one C=O, P(=O) and/or $SO_2$ unit, which is preferably bonded directly to the benz[a]anthracene. It is likewise preferred here for one or more substituents R and/or $R^1$ to contain an electron-poor heterocycle, such as, for example, imidazole, triazine, pyrimidine, pyrazine, pyridazine, pyrazole, thiazole, benzimidazole, benzothiazole, triazole, oxadiazole, benzothiadiazole, phenanthroline, etc. It is likewise preferred for one or more $Ar^1$ groups in compounds of the formulae (1) to (21) to stand for an electron-poor heterocycle, such as, for example, imidazole, triazine, pyrimidine, pyrazine, pyridazine, pyrazole, thiazole, benzimidazole, benzothiazole, triazole, oxadiazole, benzothiadiazole, phenanthroline, etc., and/or for the group Y to stand for an electron-poor heterocycle of this type or for C=O, $POAr^1$, SO or $SO_2$. It may furthermore be preferred for the compound to be doped with electron-donor compounds.

Recurring units of the formula (1) or formula (2) can also be employed in polymers either as polymer backbone, as emitting unit, as hole-transporting unit and/or as electron-transporting unit. The preferred substitution patterns here correspond to those described above.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, where the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds.

It is also possible to use a plurality of the processes mentioned above and, for example, to apply one or more layers from solution and to apply one or more further layers by vapour deposition.

Solutions or formulations of the compounds according to the invention are necessary for application from solution. The present invention therefore furthermore relates to a solution or formulation comprising at least one compound of the formula (1) or (2) and at least one solvent, preferably an organic solvent.

The compounds according to the invention have increased efficiency and a significantly longer lifetime on use in organic electroluminescent devices, making the organic electroluminescent devices according to the invention more suitable for use in high-quality and long-lived displays than those which comprise materials in accordance with the prior art. Furthermore, the compounds according to the invention have high thermal stability and a high glass-transition temperature and can be sublimed without decomposition.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photo receptors.

The present invention likewise relates to the use of the compounds according to the invention in the corresponding devices and to these devices themselves.

It is part of the present invention that the said embodiments, or preferred ranges or definitions of the present invention can be combined with one another as desired.

The invention is now explained in greater detail by the following examples, without wishing to restrict it thereby. The person skilled in the art will be able to use the details given to carry out the invention throughout the range disclosed and will be able to prepare further compounds according to the invention without inventive step and use these in electronic devices or use the process according to the invention.

EXAMPLES

The following syntheses are carried out, unless indicated otherwise, under a protective-gas atmosphere. The starting materials can be purchased from ALDRICH or ABCR or prepared by literature methods. 8-Bromobenz[a]anthracene-7,12-dione: J. L. Wood et al., *J. Am. Chem. Soc.* 1951, 73(9), 4494-4495, 9-bromobenz[a]anthracene-7,12-dione: M. C. Kloetzel et al., *J. Org. Chem.* 1961, 26(6), 1748-1754, 8- and 11-bromo bromobenz[a]anthracene-7,12-dione: V. Snieckus et al., *Tetrahedron Lett.* 1985, 26(9), 1145-1148.

Example 1

Synthesis of 8-bromobenz[a]anthracene

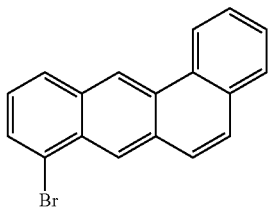 [SMILES: Brc1cccc2cc3c(ccc4ccccc43)cc12]

200 ml of hypophosphorous acid (50%) are added to a suspension of 75 g (200.2 mmol) of 8-bromobenz[a]anthracene-7,12-dione in 900 ml of glacial acetic acid, and 400 ml of hydroiodic acid (57%) are added dropwise. The reaction mixture is heated under reflux for 16 h. After cooling, the precipitated solid is filtered off with suction and washed with 500 ml of each of water, ethanol/water (1:1, v/v) and ethanol. The crude product is washed by boiling in ethanol and subsequently recrystallised from toluene/glacial acetic acid (1:1, v/v, about 15 ml/g). Drying gives 35.8 g (115.4 mmol) 57.6% of product, purity 99%.

Example 2

Synthesis of benz[a]anthracene-8-boronic acid

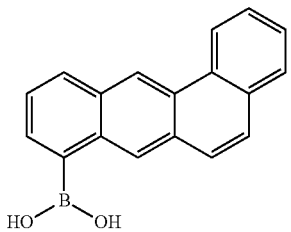 [SMILES: OB(O)c1cccc2cc3c(ccc4ccccc43)cc12]

52 ml (130 mmol) of n-butyllithium (2.5 M in n-hexane) are added dropwise with vigorous stirring at −78° C. to a suspension of 30.7 g (100 mmol) of 8-bromobenz[a]anthracene in 1000 ml of THF, and the mixture is stirred for a further 2 h. 16.7 ml (150 mmol) of trimethyl borate are added to the red solution in one portion with vigorous stirring, the mixture is stirred at −78° C. for a further 30 min., then warmed to room temperature over the course of 3 h, 300 ml of water are added, and the mixture is stirred for 30 min. The organic phase is separated off and evaporated to dryness in vacuo. The solid is taken up in 100 ml of n-hexane, filtered off with suction, washed once with 100 ml of hexane and dried in vacuo. Yield: 23.7 g (87 mmol), 87%, purity about 90% (NMR) of boronic acid, with varying amounts of boronic anhydride and borinic acid. The boronic acid can be used in this form without further purification.

The corresponding boronic acids are obtained analogously to Example 2 from the corresponding bromides (Examples 3 and 4).

| Ex. | Bromide | Boronic acid | Yield |
|---|---|---|---|
| 3 | | | 77.1% |
| 4 | | | 72.7% |

Example 5

Synthesis of 9-(naphth-2-yl)-10-(benz[a]anthracen-8-yl)-anthracene

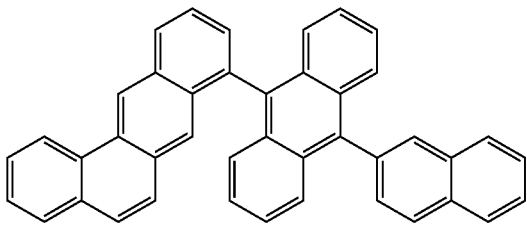 [SMILES: c1ccc2cc(-c3c4ccccc4c(-c4cccc5cc6c(ccc7ccccc76)cc45)c4ccccc34)ccc2c1]

913 mg (3 mmol) of tri-o-tolylphosphine and then 112 mg (0.5 mmol) of palladium(II) acetate are added to a well-stirred suspension of 19.2 g (50 mmol) of 9-bromo-10-(2-naphthyl)anthracene, 15.0 g (55 mmol) of benz[a]anthracene-8-boronic acid, 25.5 g (120 mmol) of tripotassium phosphate in a mixture of 300 ml of toluene, 100 ml of dioxane and 400 ml of water, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol, recrystallised three times from chlorobenzene (about 10 ml/g) and subsequently sublimed twice ($p=5\times10^{-5}$ mbar, $T=340°$ C.). Yield: 14.8 g (27.5 mmol), 55.0%, purity 99.9% (HPLC).

The following compounds according to the invention are obtained analogously to Example 5 from the corresponding bromides and boronic acids (Ex. 6 to 11).

| Ex. | Boronic acid | Bromide | Product | Yield |
|---|---|---|---|---|
| 6 | | | | 63.8% |
| 7 | | | | 61.2% |
| 8 | | | | 48.9% |

-continued
| Ex. | Boronic acid | Bromide | Product | Yield |
|---|---|---|---|---|
| 9 | 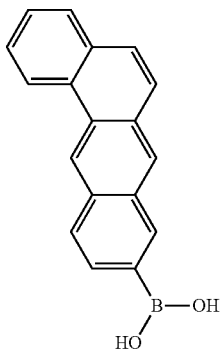 [SMILES: OB(O)c1ccc2cc3c(ccc4ccccc43)cc2c1] | 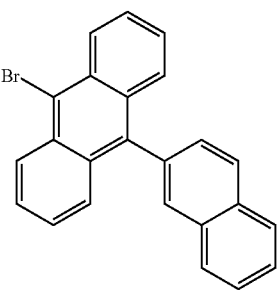 [SMILES: Brc1c2ccccc2c(-c2ccc3ccccc3c2)c2ccccc12] | 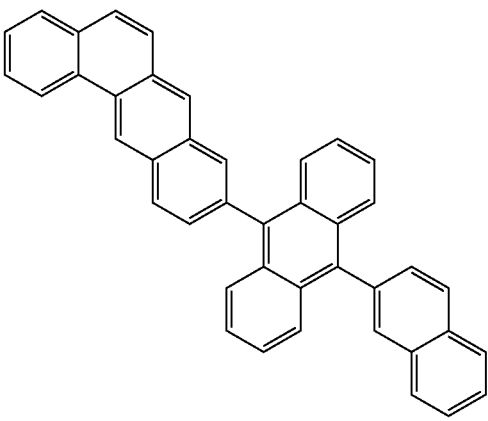 [SMILES: c1ccc2cc(-c3c4ccccc4c(-c4ccc5cc6c(ccc7ccccc76)cc5c4)c4ccccc34)ccc2c1] | 68.5% |
| 10 | 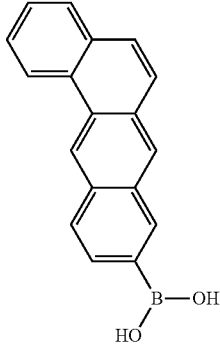 [SMILES: OB(O)c1ccc2cc3c(ccc4ccccc43)cc2c1] | 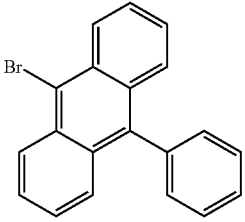 [SMILES: Brc1c2ccccc2c(-c2ccccc2)c2ccccc12] | 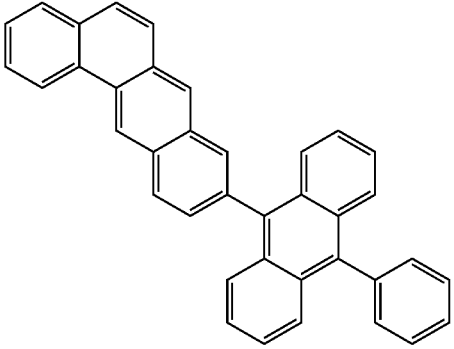 [SMILES: c1ccc(-c2c3ccccc3c(-c3ccc4cc5c(ccc6ccccc65)cc4c3)c3ccccc23)cc1] | 64.2% |
| 11 | 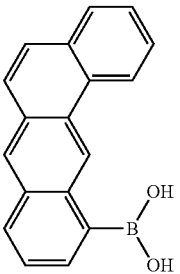 [SMILES: OB(O)c1cccc2cc3ccc4ccccc4c3cc12] | 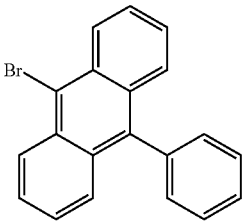 [SMILES: Brc1c2ccccc2c(-c2ccccc2)c2ccccc12] | 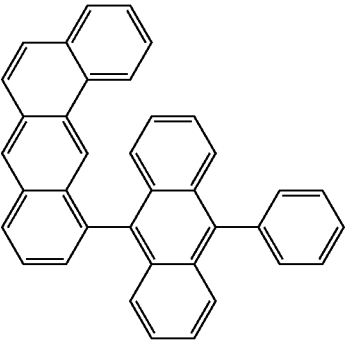 [SMILES: c1ccc(-c2c3ccccc3c(-c3cccc4cc5ccc6ccccc6c5cc34)c3ccccc23)cc1] | 45.2% |

Example 12

Synthesis of 1-phenyl-2-(4-benz[a]anthracen-8-yl-phenyl)benzimidazole

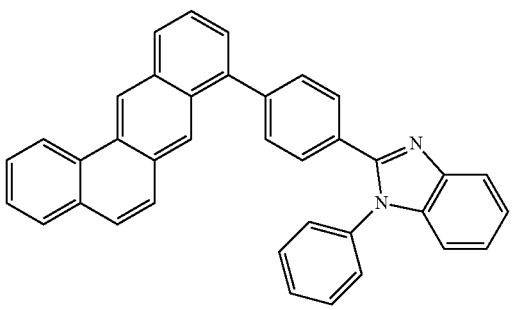 [SMILES: c1ccc(-n2c(-c3ccc(-c4cccc5cc6c(ccc7ccccc76)cc45)cc3)nc3ccccc32)cc1]

Preparation analogous to Example 7. The 19.2 g (50 mmol) of 9-bromo-10-(2-naphthyl)anthracene are replaced by 17.5 g (50 mmol) of 1-phenyl-2-(4-bromophenyl)benzimidazole. After the reaction mixture has been cooled, the organic phase is separated off, washed three times with 300 ml of water, filtered through silica gel and evaporated to dryness. The glass-like residue is dissolved in 50 ml of boiling toluene, and 100 ml of ethanol are added to the solution. After standing for 12 h, the colourless crystals are filtered off with suction and subsequently chromatographed on silica gel with pure dichloromethane (Rf=0.32). Finally, the product is recrystallised again from toluene/ethanol. Sublimation (p=5×10$^{-5}$ mbar, T=305° C.). Yield: 16.7 g (33.4 mmol), 66.8%, purity>99.9% (HPLC).

Example 13

Synthesis of 8-(bis(4-methylphenyl)amino)benz[a]-anthracene

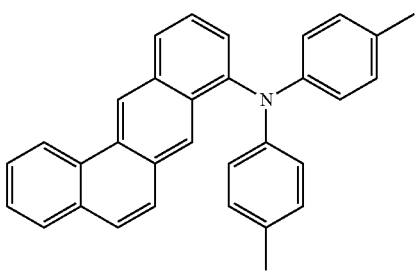 [SMILES: Cc1ccc(N(c2ccc(C)cc2)c2cccc3cc4c(ccc5ccccc54)cc23)cc1]

190 μl (1 mmol) of chloro-di-tert-butylphosphine and then 112 mg (0.5 mmol) of palladium(II) acetate are added to a suspension of 15.4 g (50 mmol) of 8-bromobenz[a]anthracene, 11.8 g (60 mmol) of bis(4-methylphenyl)amine and 7.7 g (80 mmol) of sodium tert-butoxide in 500 ml of toluene, and the mixture is subsequently heated under reflux for 5 h. After the mixture has been cooled to 60° C., 500 ml of water are added, the organic phase is separated off, filtered through silica gel, evaporated virtually to dryness at 80° C. in vacuo, and 300 ml of ethanol are then added. After cooling, the solid is filtered off with suction. The product is recrystallised five times from toluene/ethanol (1:1, v/v, about 10 ml/g); sublimation (p=5×10$^{-5}$ mbar, T=240° C.). Yield: 10.1 g (23.8 mmol), 47.5%, purity>99.9% (HPLC).

Example 14

Synthesis of 4,8-dibromobenz[a]anthracene-7,12-dione

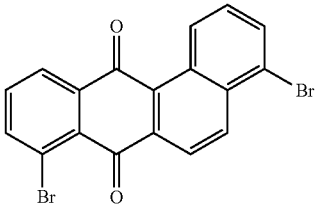 [SMILES: O=C1c2ccc3c(Br)cccc3c2C(=O)c2cccc(Br)c21]

38 ml (740 mmol) of bromine are slowly added dropwise to a solution, warmed to 140° C., of 125 g (370 mmol) of 8-bromobenz[a]anthracene-7,12-dione in 500 ml of nitrobenzene. When the evolution of hydrogen bromide has subsided (about 4 h) and after cooling, the mixture is diluted with 500 ml of ethanol, the precipitated solid is filtered off with suction and washed with copious ethanol. Washing by boiling in 1 l of ethanol and drying gives 140 g (336.5 mmol) 90.8% of product, purity about 90% (NMR), which can be used in this form without further purification.

Example 15

Synthesis of 4,8-dibromobenz[a]anthracene

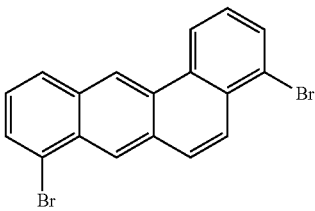 [SMILES: Brc1cccc2cc3c(ccc4c(Br)cccc43)cc12]

200 ml of hypophosphorous acid (50%) are added to a suspension of 83.2 g (200 mmol) of 4,8-dibromobenz[a]anthracene-7,12-dione in 900 ml of glacial acetic acid, and 400 ml of hydroiodic acid (57%) are added dropwise. The reaction mixture is heated under reflux for 36 h. After cooling, the precipitated solid is filtered off with suction and washed with 500 ml of each of water, ethanol/water (1:1, v/v) and ethanol. The crude product is washed by boiling in ethanol and subsequently recrystallised from toluene/glacial acetic acid (1:1, v/v, about 12 ml/g). Drying gives 48.6 g (125.9 mmol) 62.9% of product, purity 99%.

Example 16

Synthesis of benz[a]anthracene-4,8-diboronic acid

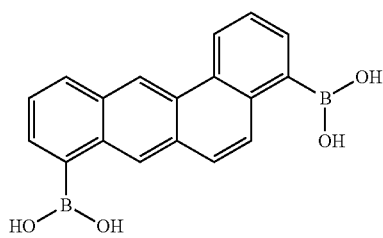 [SMILES: OB(O)c1cccc2cc3c(ccc4c(B(O)O)cccc43)cc12]

104 ml (260 mmol) of n-butyllithium (2.5 M in n-hexane) are added dropwise with vigorous stirring at −78° C. to a suspension of 38.6 g (100 mmol) of 4,8-dibromobenz[a]anthracene in 1000 ml of THF, and the mixture is stirred for a further 2 h. 33.4 ml (300 mmol) of trimethyl borate are added in one portion to the red solution with vigorous stirring, the mixture is stirred at −78° C. for a further 30 min. and then warmed to room temperature over the course of 3 h, 500 ml of water are added, and the mixture is stirred for 30 min. The organic phase is separated off and evaporated to dryness in vacuo. The solid is taken up in 100 ml of n-hexane, filtered off with suction, washed once with 100 ml of hexane and dried in vacuo. Yield: 26.5 g (84 mmol), 84%, purity about 90% (NMR) of diboronic acid, with varying amounts of boronic anhydride and borinic acid. The diboronic acid can be used in this form without further purification.

Example 17

Synthesis of 4,8-bis(naphth-2-yl)benz[a]anthracene

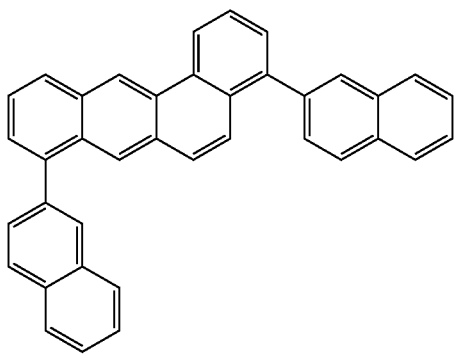 [SMILES: c1ccc2cc(-c3cccc4cc5c(ccc6c(-c7ccc8ccccc8c7)cccc65)cc34)ccc2c1]

1.83 g (6 mmol) of tri-o-tolylphosphine and then 224 mg (1 mmol) of palladium(II) acetate are added to a vigorously stirred suspension of 15.8 g (50 mmol) of benz[a]anthracene-4,8-diboronic acid and 22.8 g (110 mmol) of 2-bromonaphthalene, 50.1 g (240 mmol) of tripotassium phosphate in a mixture of 300 ml of toluene, 100 ml of dioxane and 400 ml of water, and the mixture is subsequently heated under reflux for 16 h. After cooling, the mixture is diluted with 1000 ml of ethanol, the precipitated solid is filtered off with suction, washed three times with 50 ml of ethanol:water (1:1, v:v) and three times with 100 ml of ethanol. The crude product is recrystallised four times from dioxane (about 7 ml/g) and subsequently sublimed twice (p=5×10$^{-5}$ mbar, T=380° C.). Yield: 10.3 g (21.5 mmol), 43.0%, purity 99.9% (HPLC).

Example 18

Production of OLEDs

OLEDs are produced by a general process as described in WO 04/058911, which is adapted in individual cases to the particular circumstances (for example layer-thickness variation in order to achieve optimum efficiency or colour).

Examples 19 to 32 below show the results for various OLEDs. Glass plates coated with structured ITO (indium tin oxide) form the substrates of the OLEDs. For improved processing, 20 nm of PEDOT (spin-coated from water; purchased from H.C. Starck, Goslar, Germany; poly(3,4-ethylenedioxy-2,5-thiophene)) are applied to the substrate. The OLEDs consist of the following layer sequence: substrate/PEDOT/hole-transport layer (HTM) 40 nm/emission layer (EML) 30 nm/electron-transport layer (ETM) 20 nm and finally a cathode. The materials apart from the PEDOT are thermally vapour-deposited in a vacuum chamber. The emission layer here always consists of a matrix material (host) and a dopant with which the matrix material is admixed by co-evaporation. The cathode is formed by an LiF layer with a thickness of 1 nm and a 100 nm Al layer deposited thereon.

Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current/voltage/luminance characteristic lines (IUL characteristic lines), and the lifetime are determined. The lifetime is defined as the time after which the initial luminance has dropped from 6000 cd/m$^2$ to half.

Table 2 shows the results for some OLEDs (Examples 19 to 30). The compounds of Examples 5, 6 and 11 are used as matrix materials according to the invention. Matrix material H1 in accordance with the prior art is used as comparison.

Table 3 shows the results for OLEDs (Examples 31 and 32) which comprise the compound from Example 12 as electron-transport material according to the invention. As comparison, AlQ$_3$ is used as electron-transport material in accordance with the prior art.

TABLE 1

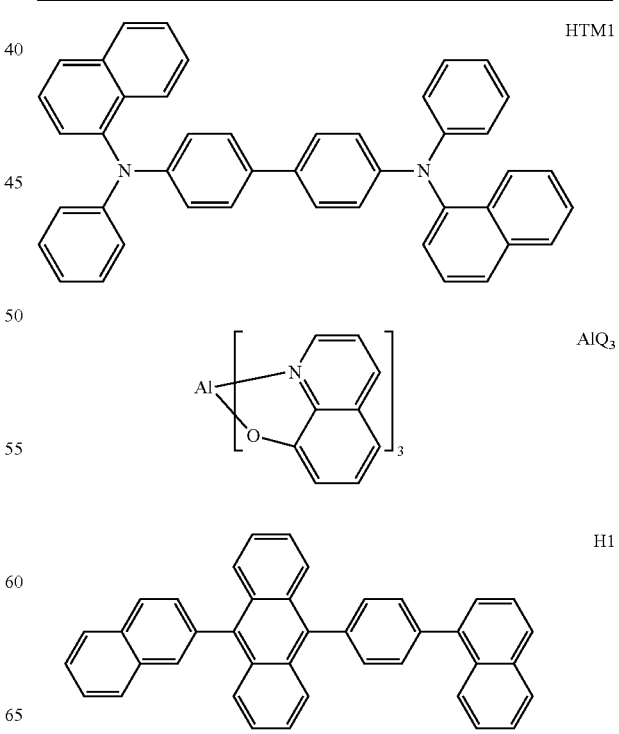

TABLE 1-continued

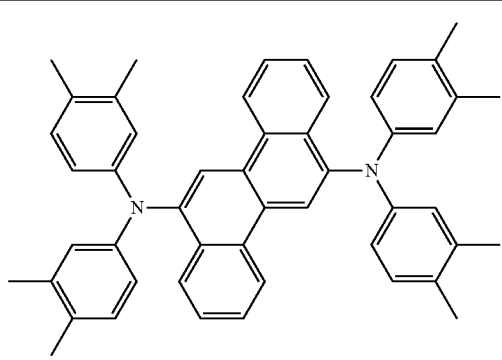
D1

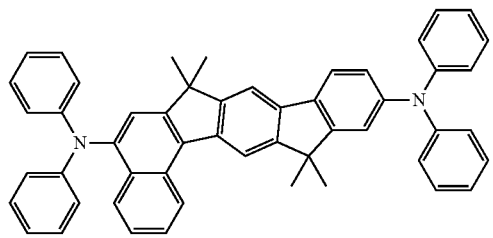 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
D2

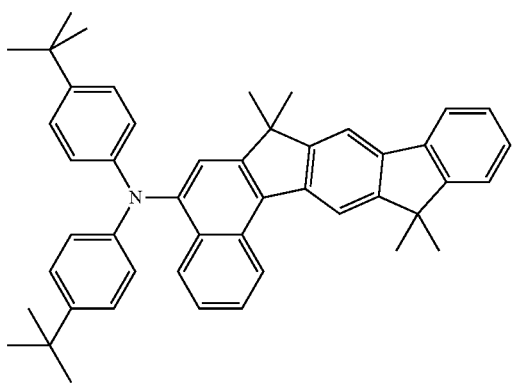 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
D3

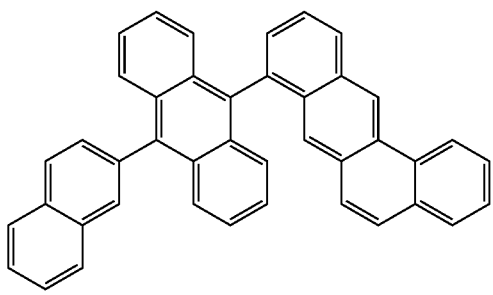 [SMILES: c1ccc2cc(-c3c4ccccc4c(-c4cccc5cc6c(ccc7ccccc76)cc45)c4ccccc34)ccc2c1]
Ex. 5

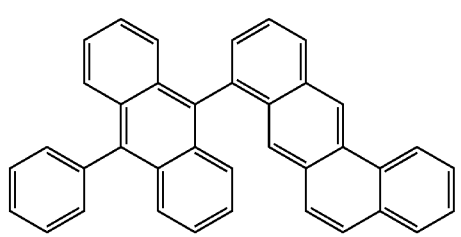 [SMILES: c1ccc(-c2c3ccccc3c(-c3cccc4cc5c(ccc6ccccc65)cc34)c3ccccc23)cc1]
Ex. 6

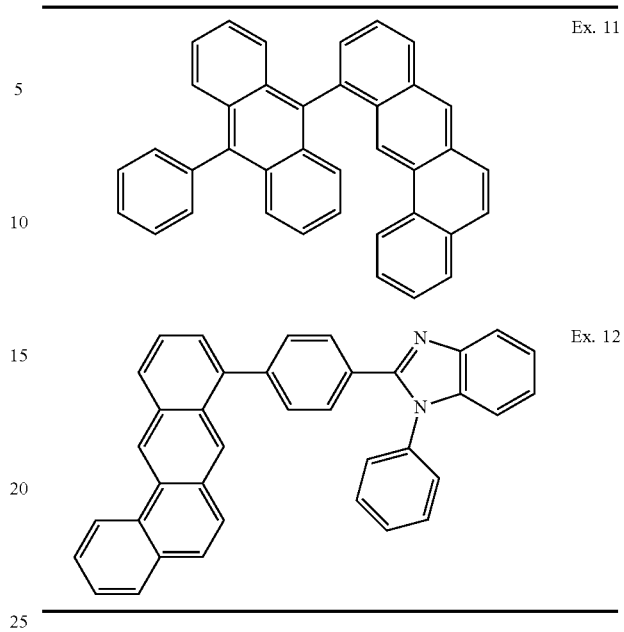
Ex. 11

Ex. 12

TABLE 2

| Example | EML | Max. efficiency (cd/A) | Voltage (V) at 1000 cd/m² | CIE | Lifetime (h) at 6000 cd/m² |
|---|---|---|---|---|---|
| 19 (comparison) | H1 + 5% of D1 | 6.8 | 5.8 | x = 0.14/ y = 0.19 | 210 |
| 20 (comparison) | H1 + 5% of D2 | 7.0 | 5.9 | x = 0.14/ y = 0.18 | 240 |
| 21 (comparison) | H1 + 5% of D3 | 6.9 | 5.7 | x = 0.14/ y = 0.21 | 280 |
| 22 | Ex. 5 + 5% of D1 | 7.0 | 5.8 | x = 0.14/ y = 0.19 | 260 |
| 23 | Ex. 5 + 5% of D2 | 7.2 | 5.7 | x = 0.14/ y = 0.17 | 270 |
| 24 | Ex. 5 + 5 of D3 | 7.5 | 5.9 | x = 0.14/ y = 0.21 | 350 |
| 25 | Ex. 11 + 5% of D1 | 7.2 | 5.9 | x = 0.14/ y = 0.19 | 250 |
| 26 | Ex. 11 + 5% of D2 | 7.4 | 5.6 | x = 0.14/ y = 0.17 | 290 |
| 27 | Ex. 11 + 5% of D3 | 7.8 | 5.7 | x = 0.14/ y = 0.22 | 440 |
| 28 | Ex. 6 + 5% of D1 | 6.9 | 5.8 | x = 0.14/ y = 0.19 | 240 |
| 29 | Ex. 6 + 5 of D2 | 7.2 | 5.5 | x = 0.14/ y = 0.17 | 310 |
| 30 | Ex. 6 + 5% of D3 | 7.3 | 5.4 | x = 0.14/ y = 0.20 | 460 |

TABLE 3

| Example | EML | ETM | Max. efficiency (cd/A) | Voltage (V) at 1000 cd/m² | CIE |
|---|---|---|---|---|---|
| 31 (comparison) | Ex. 5 + 5% of D2 | AlQ₃ | 7.2 | 5.7 | x = 0.14/y = 0.17 |
| 32 | Ex. 5 + 5% of D2 | Ex. 12 | 7.8 | 5.0 | x = 0.14/y = 0.17 |

As is evident from the examples given above, the organic electroluminescent devices according to the invention which comprise the compounds according to the invention as

The invention claimed is:
1. A compound of the formula (9) or (10),

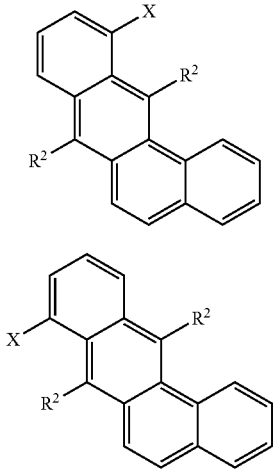

formula (9)

formula (10)

where the dashes drawn as nonspecific bonds are intended to denote that the group X is bonded, in each case independently of one another, via one of positions 8 or 11 of the respective benz[a]anthracene, where the following applies to the symbols and indices:

X is selected from the units of the following formulae (24) to (25):

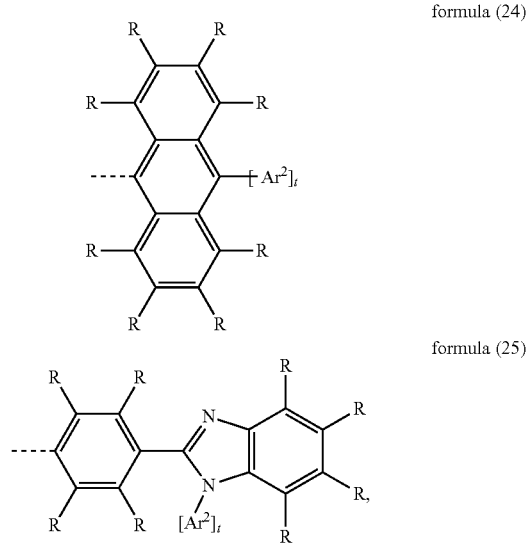

formula (24)

formula (25)

Ar² is an aryl or heteroaryl group having 5 to 16 aromatic ring atoms, which is optionally substituted by one or more radicals $R^1$;

t is 1;

R, $R^2$ are, identically or differently on each occurrence, H, D, F, Cl, Br, I, CHO, $N(R^1)_2$, $N(Ar^1)_2$, $C(=O)Ar^1$, $P(=O)(Ar^1)_2$, $S(=O)Ar^1$, $S(=O)_2Ar^1$, $CR^1=CR^1Ar^1$, CN, $NO_2$, $Si(R^1)_3$, $B(OAr^1)_2$, $B(OR^1)_2$, $OSO_2R^1$, OH, a straight-chain alkyl, alkoxy or thioalkyl group having 1 to 40 C atoms or a branched or cyclic alkyl, alkoxy or thioalkyl group having 3 to 40 C atoms or an alkenyl group having 2 to 40 C atoms, each of which is optionally substituted by one or more radicals $R^1$, where one or more non-adjacent $CH_2$ groups is optionally replaced by $R^1C=CR^1$, C≡C, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals R, or an aryloxy or heteroaryloxy group having 5 to 60 aromatic ring atoms, which may in each case be substituted by one or more non-aromatic radicals R, or a combination of these systems; two or more adjacent substituents R here may also be linked to one another and form a mono- or polycyclic aliphatic ring system, with the proviso that both $R^2$ in a benz[a]anthracene are either equal to H or not equal to H;

$Ar^1$ is on each occurrence, identically or differently, a mono-or poly-cyclic aromatic or heteroaromatic ring system having 5 to 30 aromatic ring atoms, which is optionally substituted by one or more non-aromatic radicals R; two radicals $Ar^1$ which are bonded to the same nitrogen or phosphorus atom may also be linked to one another here by a single bond or by a bridge selected from the group consisting of $B(R^1)$, $C(R^1)_2$, $Si(R^1)_2$, C=O, $C=NR^1$, $C=C(R^1)_2$, O, S, S=O, $SO_2$, $N(R^1)$, $P(R^1)$ and $P(=O)R^1$;

$R^1$ is on each occurrence, identically or differently, H, D or an aliphatic, aromatic and/or heteroaromatic hydrocarbon radical having 1 to 20 C atoms, in which, in addition, one or more H atoms is optionally replaced by F; two or more adjacent substituents $R^1$ here may also form a mono-or polycyclic aliphatic or aromatic ring system with one another.

2. The compound according to claim 1, wherein Ar² is phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benz-imidazole, 2-fluorenyl, 2-spirobifluorenyl, fluoranthenyl, 2-benz[a] anthracenyl, 3-benz[a]anthracenyl, 4-benz[a] anthracenyl, 5-benz[a]anthracenyl or 6-benz[a] anthracenyl, each of which is optionally substituted by one or more radicals $R^1$.

3. A process for the preparation of the compound according to claim 1, which comprises coupling a benz[a]anthracene which is substituted in position 8 or 11 by a reactive leaving group to a functionalised aromatic compound or to a mono- or disubstituted amine.

4. An oligomer, polymer or dendrimer comprising one or more compounds according to claim 1, where one or more radicals R or $R^2$ or X represent bonds from the compound according to claim 1 to the polymer, oligomer or dendrimer.

5. An electronic device comprising at least one compound according to claim 1.

6. The electronic device as claimed in claim 5, wherein the device is selected from organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

7. The electronic device as claimed in claim 5, wherein the device is an organic electroluminescent device wherein the compound of the formula (9) or (10) is employed as matrix material for fluorescent dopants, where the fluorescent dopants are selected from the class of monostyrylamines, distyrylamines, tristyrylamines, tetrastyrylamines, styrylphosphines, styryl ethers, and arylamines, containing condensed aromatic groups, and condensed aromatic hydrocarbons, or wherein the compound of the formula (9) or (10) is employed as emitting material, as hole-transport material, as hole-injection material or as electron-transport material.

8. A solution or formulation comprising at least one compound according to claim 1 and at least one solvent.

9. The electronic device as claimed in claim 7, wherein the compound of the formula (9) or (10) is employed as matrix material in an emitting layer comprising exactly one matrix material and one or more dopants.

10. The electronic device as claimed in claim 7, wherein the compound of the formula (9) or (10) is employed as electron-transport material.

* * * * *